US009012143B2

(12) United States Patent
Sadee et al.

(10) Patent No.: US 9,012,143 B2
(45) Date of Patent: Apr. 21, 2015

(54) POLYMORPHISMS IN GENES AFFECTING ACE-RELATED DISORDERS AND USES THEREOF

(75) Inventors: Wolfgang Sadee, Upper Arlington, OH (US); Andrew D. Johnson, Columbus, OH (US); Danxin Wang, Upper Arlington, OH (US); Audrey C. Papp, Columbus, OH (US)

(73) Assignee: The Ohio State University Research Foundation, Columbus, OH (US)

(*) Notice: Subject to any disclaimer, the term of this patent is extended or adjusted under 35 U.S.C. 154(b) by 730 days.

(21) Appl. No.: 12/598,265

(22) PCT Filed: Apr. 30, 2008

(86) PCT No.: PCT/US2008/005558
§ 371 (c)(1),
(2), (4) Date: Oct. 30, 2009

(87) PCT Pub. No.: WO2008/136996
PCT Pub. Date: Nov. 13, 2008

(65) Prior Publication Data
US 2010/0167947 A1  Jul. 1, 2010

Related U.S. Application Data

(60) Provisional application No. 60/926,932, filed on Apr. 30, 2007.

(51) Int. Cl.
*C12Q 1/68* (2006.01)

(52) U.S. Cl.
CPC ........ *C12Q 1/6883* (2013.01); *C12Q 2600/106* (2013.01); *C12Q 2600/154* (2013.01); *C12Q 2600/156* (2013.01); *C12Q 2600/158* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

| 5,882,944 | A | 3/1999 | Sadee |
| 6,007,986 | A | 12/1999 | Sadee |
| 6,197,505 | B1 * | 3/2001 | Norberg et al. ............ 435/6.18 |
| 6,228,840 | B1 | 5/2001 | Wei et al. |
| 6,270,979 | B1 | 8/2001 | Sadee |
| 6,582,908 | B2 * | 6/2003 | Fodor et al. ............... 506/9 |
| 6,713,488 | B2 | 3/2004 | Sadee et al. |
| 6,812,339 | B1 | 11/2004 | Venter et al. |
| 6,953,779 | B2 | 10/2005 | Wei et al. |
| 2001/0034023 | A1 | 10/2001 | Stanton, Jr. et al. |
| 2001/0049375 | A1 | 12/2001 | Sadee et al. |
| 2003/0059774 | A1 | 3/2003 | Risinger et al. |
| 2003/0148295 | A1 | 8/2003 | Wan et al. |
| 2004/0115701 | A1 | 6/2004 | Comings et al. |
| 2005/0026169 | A1 | 2/2005 | Cargill et al. |
| 2005/0208512 | A1 | 9/2005 | Sadee et al. |
| 2005/0272054 | A1 | 12/2005 | Cargill et al. |
| 2007/0065821 | A1 | 3/2007 | Kudaravalli et al. |
| 2007/0197573 | A1 | 8/2007 | Sadee et al. |
| 2009/0111844 | A1 | 4/2009 | Sadee et al. |
| 2010/0075308 | A1 | 3/2010 | Sadee et al. |
| 2010/0129818 | A1 | 5/2010 | Sadee et al. |

FOREIGN PATENT DOCUMENTS

| WO | 2004074513 A1 | 9/2004 |
| WO | 2008136988 A2 | 11/2008 |
| WO | 2008136989 A2 | 11/2008 |
| WO | 2008136995 A1 | 11/2008 |
| Wo | 2008136996 A2 | 11/2008 |

OTHER PUBLICATIONS

NCBI dbSNP database. Submitted SNP details: ss23448494, Submitted Aug. 20, 2004, including method details, obtained from www.ncbi.hlm.nih.gov on Mar. 21, 2012.*
Sayed-Tabatabaei et al. (Circ Res 2006; 98:1123-1133).*
Hegele (Arterioscler Thromb Vasc Biol 2002 vol. 22 pp. 1058-1061).*
Johnson, dissertation entitled "Search for Functional Alleles in the Human Genome With Focus on Cardiovascular Disease Candidate Genes," The Ohio State University, 2007, 260 pages.*
PCT International Search Report and the Written Opinion, PCT/US2008/05558 filed Apr. 30, 2008, dated Nov. 5, 2008.
PCT International Preliminary Report, PCT/US2008/005558 filed Apr. 30, 2008, dated Nov. 12, 2009.
PCT International Search Report and the Written Opinion, PCT/US2008/05540 filed Apr. 30, 2008, dated Dec. 24, 2008.
PCT International Preliminary Report, PCT/US2008/005540 filed Apr. 30, 2008, dated Nov. 12, 2009.
PCT International Search Report and the Written Opinion, PCT/US2008/05556 filed Apr. 30, 2008, dated Sep. 25, 2008.
PCT International Preliminary Report, PCT/US2008/005556 filed Apr. 30, 2008, dated Nov. 12, 2009.
PCT International Search Report and the Written Opinion, PCT/US2008/05539 filed Apr. 30, 2008, dated Nov. 18, 2008.
PCT International Preliminary Report, PCT/US/2008/005539 filed Apr. 30, 2008, dated Nov. 12, 2009.
European Patent Office, European Search Report, EP Application No. 08 754 150.4, dated Apr. 16, 2010.
European Patent Office, EPO cf Form 1507 and Supplementary European Search Report, EP Application No. 08 754 148.8, dated Apr. 8, 2010.
Adamzik, M. et al., "ACE I/D but not AGT (-6)A/G Polymorphism is a Risk Factor for Mortality in ARDS," European Respiratory Journal, 2007, pp. 482-488, vol. 29, No. 3, ERS Journals Ltd., XP-002576511.
Bannon, M.J., "The Dopamine Transporter: Role in Neurotoxicity and Human Disease," Toxicol. Appl. Pharmacology, May 1, 2005, pp. 355-360, vol. 204, No. 3, Elsevier, http://www.ncbi.nlm.nih.gov, Abstract.
Brown, N.J. et al., "Black Americans have an Increased Rate of Angiotensin Converting Enzyme Inhibitor-Associated Angioedema," Clinical Pharmacological Therapy, Jun. 1997, p. 700, vol. 61, No. 6, Nature Publishing Group, http://www.ncbi.nlm.nih.gov, Abstract.

(Continued)

*Primary Examiner* — Juliet Switzer
(74) *Attorney, Agent, or Firm* — MacMillan, Sobanski & Todd, LLC

(57) ABSTRACT

A method for predicting a subject's risk factors for ACE-related disorders includes detecting the allelic status of one or more polymorphisms in a nucleic acid sample of the subject.

4 Claims, 42 Drawing Sheets

(56) References Cited

OTHER PUBLICATIONS

Exner, D.V. et al., "Lesser Response to Angiotensin-Converting-Enzyme Inhibitor Therapy in Black as Compared with White Patients with Left Ventricular Dysfunction," New England Journal of Medicine, May 3, 2001, vol. 344, No. 18, Massachusetts Medical Society, www.nejm.org, Abstract.

Feng, Yu et al., "Sequence Variation in the 3'-Untranslated Region of the Dopamine Transporter Gene and Attention-Deficit Hyperactivity Disorder(ADHD)," American Journal of Medical Genetics Part B (Neuropsychiatric Genetics), 2005, pp. 1-6, vol. 139(B), Wiley-Liss, Inc.

Friedel, S. et al., "Association and Linkage of Allelic Variants of the Dopamine Transporter Gene in ADHD," Molecular Psychiatry, 2007, pp. 923-933, vol. 12, Nature Publishing Group, XP-002576434.

Hiroi, S. et al., "Polymorphisms in the SOD2 and HLA-DRB1 Genes are Associated with Nonfamilial Idiopathic Dilated Cardiomyopathy in Japanese," Biochem. Biophys. Res. Commun., Aug. 2, 1999, pp. 332-339, vol. 261, No. 2, Elsevier, http://www.ncbi.nlm.nih.gov, Abstract.

Johnson, A.D. et al., "Polymorphisms Affecting Gene Transcription and mRNA Processing in Pharmacogenetic Candidate Genes: Detection through Allelic Expression Imbalance in Human Target Issues," Pharmacogenetics and Genomics, 2008, pp. 781-791, vol. 18, No. 9, Lippincott, Williams & Wilkins.

Johnson, A.D. et al., "Promoter Polymorphisms in ACE(Angiotensin I-Converting Enzyme) Associated with Clinical Outcomes in Hypertension," Clinical and Pharmacological Therapy, Jan. 2009, pp. 36-44, vol. 85, No. 1, XP002576512.

Lei, H et al., "Exonization of AluYa5 in the Human ACE Gene Requires Mutations in both 3' and 5' Splice Sites and is Facilitated by a Conserved Splicing Enhancer," Nucleic Acids Research, 2005, pp. 3897-3906, vol. 33, No. 12, Oxford University Press, Abstract.

Liao, L.-H. et al., "The Association of CYP2C9 Gene Polymorphisms with Colorectal Carcinoma in Han Chinese," Clinica Chimica Acta, 2007, pp. 191-196, vol. 380, Elsevier.

Lightfoot, T.J. et al., "Polymorphisms in the Oxidative Stress Genes, Superoxide Dismutase, Glutathione Peroxidase and Catalase and Risk of Non-Hodgkin's Lymphoma," Haematologica, 2006, pp. 1222-1227, vol. 91, No. 9, Ferrata Storti Foundation.

Ling, D. et al., "Association between Polymorphism of the Dopamine Transporter Gene and Early Smoking Onset: An Interaction Risk on Nicotine Dependence," Journal of Human Genetics, 2004, pp. 35-39, vol. 49, XP-002576435.

Mollsten, A. et al., "A Functional Polymorphism in the Manganese Superoxide Dismutase Gene and Diabetic Nephropathy," Diabetes, Jan. 2007, pp. 265-269, vol. 56, American Diabetes Association.

Ouellet-Morin, I. et al., "Association of the Dopamine Transporter Gene and ADHD Symptoms in a Canadian Population-Based Sample of Same-Age Twins," American Journal of Medical Genetics Part B (Neuropsychiatric Genetics), 2008, pp. 1442-1449, vol. 147B, Wiley-Liss, Inc.

Rosatto, N. et al., "Intron 16 Insertion of the Angiotensin Converting Enzyme Gene and Transcriptional Regulation," Nephrology Dialysis Transplantation, 1999, pp. 868-871, vol. 14, European Renal Association—European Dialysis and Transplant Association, Abstract.

Sadee, W. et al., "Pharmacogenetics/Genomics and Personalized Medicine," Human Molecular Genetics, 2005, pp. R207-R214, vol. 14, Review Issue 2, Oxford University Press.

Solus, J.F. et al., "Genetic Variation in Eleven Phase I Drug Metabolism Genes in an Ethnically Diverse Population," Pharmacogenomics, 2004, pp. 895-931, vol. 5, No. 7, Future Medicine Ltd.

Sotnikova, TD., et al., "Molecular Biology, Pharmacology and Functional Role of the Plasma Membrane Dopamine Transporter," CNS Neurol Disord Drug Targets, Feb. 2006, pp. 45-56, vol. 5, No. 1, Bentham Direct, http://www.ncbi.nlm.nih.gov, Abstract.

Strat, Y.L. et al., "The 3' Part of the Dopamine Transporter Gene DAT1/SLC6A3 is Associated with Withdrawal Seizures in Patients with Alcohol Dependence," Alcoholism: Clinical and Experimental Research, Jan. 2008, pp. 27-35, vol. 32, No. 1, Research Society on Alcoholism, XP002576437.

Talkowski, M.E. et al., "A Network of Dopaminergic Gene Variations Implicated as Risk Factors for Schizophrenia," Human Molecular Genetics, 2008, pp. 747-758, vol. 17, No. 5, Oxford University Press, XP-002576438.

Wang, D. et al., "Searching for Polymorphisms that Affect Gene Expression and mRNA Processing: Example ABCB1 (MDR1)," The AAPS Journal, Aug. 2006, pp. E515-E520, vol. 8, No. 3, Article 61.

\* cited by examiner

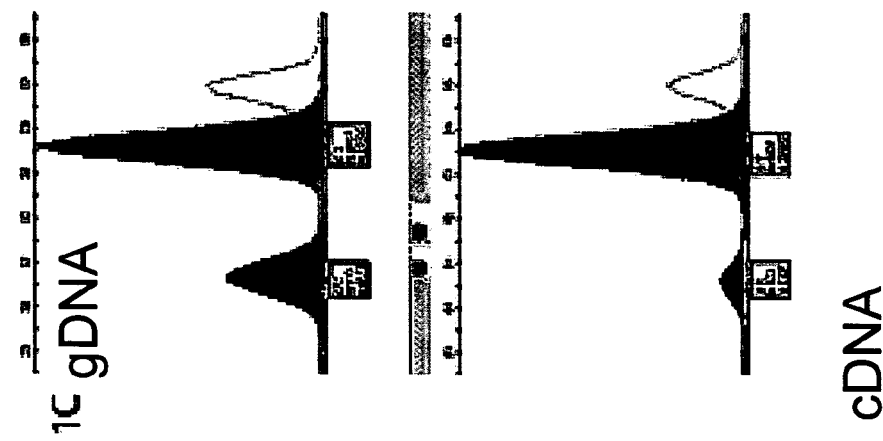
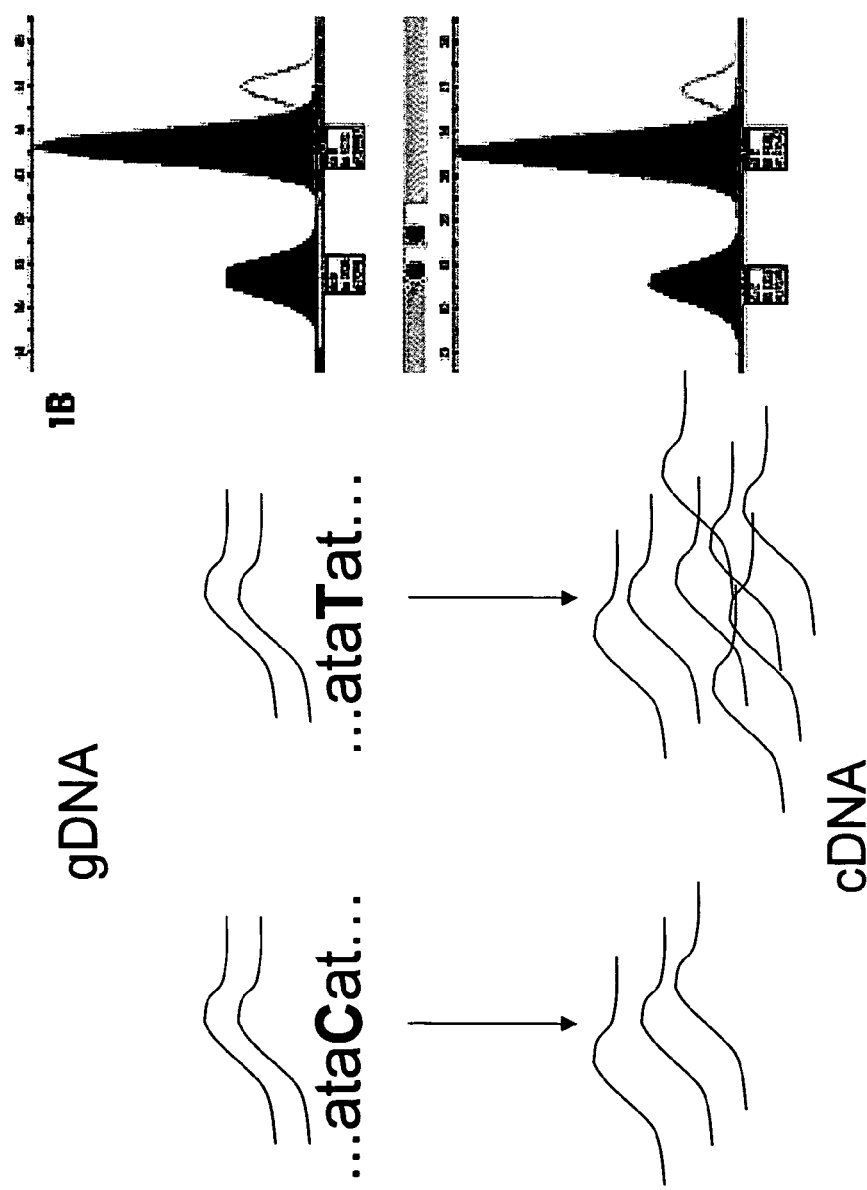
Figure 6b
Figure 6a

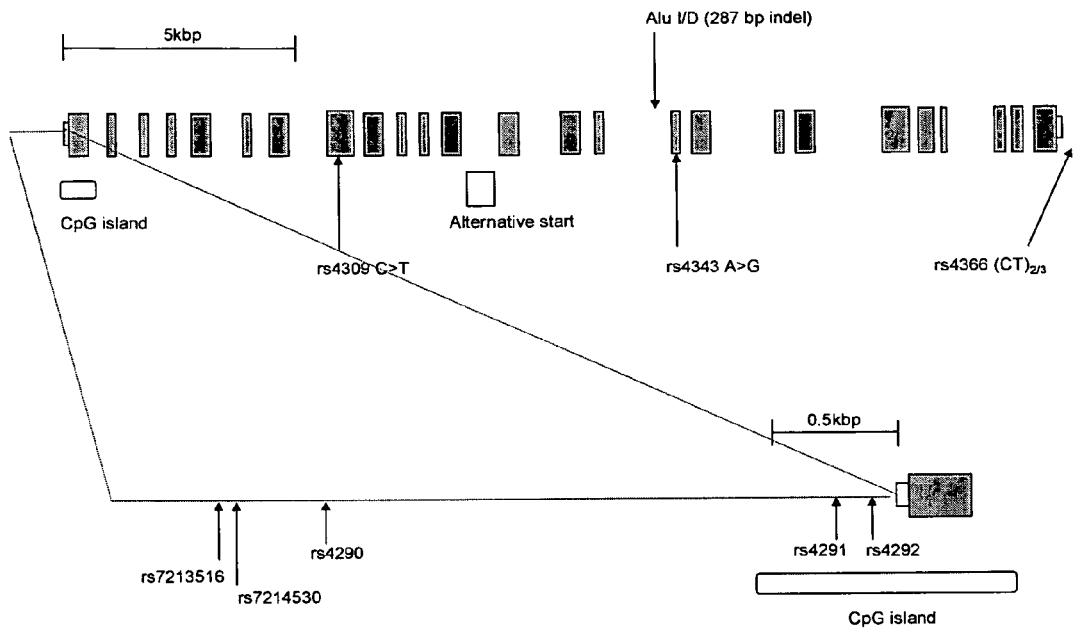

Figure 9

Table 1. Unadjusted and adjusted odds ratios and 95% confidence intervals for secondary outcomes by genotype

| | | Unadjusted OR (95% CI) | Adjusted OR† (95% CI) |
|---|---|---|---|
| All cause death (n = 90) | rs7213516 (A carriers vs. GG) | 1.04 (0.44-2.49) | 1.68 (0.62-4.54) |
| | rs4290 (T carriers vs. CC) | 1.41 (0.68-2.94) | 1.92 (0.83-4.46) |
| | rs13447447 (ID vs. DD) | 1.49 (0.87-2.55) | 1.45 (0.83-2.52) |
| | rs13447447 (II vs. DD) | 1.34 (0.65-2.77) | 1.34 (0.63-2.82) |
| Nonfatal MI (n = 75) | rs7213516 (A carriers vs. GG) | 2.81 (1.40-5.64)* | 6.16 (2.43-15.60)** |
| | rs4290 (T carriers vs. CC) | 1.78 (0.85-3.73) | 2.37 (0.99-5.69) |
| | rs13447447 (ID vs. DD) | 0.59 (0.34-1.02) | 0.61 (0.34-1.07) |
| | rs13447447 (II vs. DD) | 1.41 (0.76-2.65) | 1.44 (0.75-2.79) |
| Nonfatal stroke (n = 81) | rs7213516 (A carriers vs. GG) | 1.68 (0.77-3.65) | 1.72 (0.70-4.24) |
| | rs4290 (T carriers vs. CC) | 1.43 (0.66-3.09) | 1.27 (0.54-3.02) |
| | rs13447447 (ID vs. DD) | 0.69 (0.40-1.20) | 0.66 (0.37-1.16) |
| | rs13447447 (II vs. DD) | 1.34 (0.70-2.59) | 1.41 (0.72-2.76) |

†Adjusted for: age, sex, race/ethnicity, BMI, smoking, previous myocardial infarction, heart failure, diabetes and ancestry.
*P = 0.004; **P = 0.0001

Figure 10 - Table 1

| Table 2A | SNP location | Minor allele frequencies, human heart tissues | |
|---|---|---|---|
| | | Caucasians | African-Americans |
| rs7213516 (G>A) | -2883 from TSS | 0.0% | 27.3% (n=12) |
| rs7214530 (T>G) | -2828 from TSS | n.d. | 29.0% (n=12) |
| rs4290 (C>T) | -2305 from TSS | 0.0% | 25.0% (n=12) |
| rs4291 (A>T) | -240 from TSS | 34.2% | 31.3% (n=8) |
| rs4292 (T>C) | -93 from TSS | 31.6% | 6.3% (n=8) |
| rs4309 (C>T) AEI marker SNP | exon 8 (Pro>Pro) | 44.4% | 37.5% (n=12) |
| rs13447447 (I/D, insertion/deletion) | intron 15 | 49.1%† | 45.5% (n=11) |
| rs4343 (A>G) AEI marker SNP | exon 16 (Thr>Thr) | 48.1%† | 20.8% (n=12) |
| rs4357 (C>T) | intron 21 | 0.0% | 22.7% (n=11) |
| rs4363 (A>G) | intron 24 | 47.2% | 36.4% (n=11) |
| rs4366 (22/33) | 3' downstream | 49.1% | 27.3% (n=11)** |

Figure 11a - Table 2A

| Table 2B | | Minor Allele Frequencies INVEST-GENE | | | | |
|---|---|---|---|---|---|---|
| | Minor Allele | Overall | Caucasians | Hispanics | African Americans | P value* |
| rs7213516 (G>A) | A | 3.37% | 0.17% | 4.33% | 16.00% | <0.0001 |
| rs4290 (C>T) | T | 3.60% | 0.57% | 4.21% | 16.03% | <0.0001 |
| rs4291 (A>T) | T | 37.12% | 38.78% | 34.68% | 32.92% | 0.11 |
| rs13447447 (I/D) | I | 41.16% | 41.67% | 39.62% | 40.57% | 0.38 |
| rs4366 (22/33) | 22** | 47.91% | 55.89% | 49.79% | 40.16% | 0.0004 |

*: p-value for chi-squared tests or Fisher's exact test for the genotype frequencies by race/ethnicity, as appropriate.
**: 22 is the minor allele in Hispanics and African Americans; 33 is the minor allele in Caucasians
†: rs13447447 (I) and rs4343 (A) were the minor alleles in the Caucasian heart tissue samples

Figure 11b - Table 2B

| Characteristic (N, % unless otherwise noted) | Cases (N = 258) | Controls (N = 774) |
|---|---|---|
| Age, mean (SD), years | 71.5 (9.9) | 70.2 (9.3) |
| Women | 131 (50.8) | 393 (50.8) |
| BP, mean (SD), mmHg | | |
| Systolic | 150.6 (19.0) | 147.4 (19.0) |
| Diastolic | 83.6 (11.1) | 83.3 (11.1) |
| Race/ethnicity | | |
| White | 158 (61.2) | 472 (61.0) |
| Black | 36 (14.0) | 101 (13.1) |
| Hispanic | 63 (24.4) | 198 (25.6) |
| Other/multiracial | 1 (0.4) | 3 (0.4) |
| BMI, mean (SD), kg/m$^2$ | 27.4 (4.8) | 29.0 (5.5) |
| Medical History | | |
| Prior Myocardial infarction | 96 (37.2) | 230 (29.7) |
| Angina pectoris | 153 (59.3) | 483 (62.4) |
| Prior Stroke/TIA | 36 (14.0) | 71 (9.2) |
| Left ventricular hypertrophy | 46 (17.8) | 136 (17.6) |
| Heart failure (class I-III) | 28 (10.9) | 29 (3.8) |
| Peripheral vascular disease | 43 (16.7) | 88 (11.4) |
| Smoking | | |
| Past | 133 (51.6) | 355 (45.9) |
| Within 30 days | 34 (13.2) | 83 (10.7) |
| Diabetes‡ | 102 (39.5) | 224 (28.9) |
| Hypercholesterolemia‡ | 161 (62.4) | 485 (62.7) |
| Renal impairment† | 14 (5.4) | 18 (2.3) |
| Cancer | 20 (7.8) | 46 (5.9) |
| Medication at Enrollment | | |
| Aspirin/other antiplatelet agent | 162 (62.8) | 451 (58.3) |
| Antidiabetic medication | 86 (33.3) | 188 (24.3) |
| Any lipid-lowering agent | 106 (41.1) | 331 (42.8) |
| Nitrates | 92 (35.7) | 232 (30.0) |

Baseline characteristics for the INVEST-GENES case and control patients.

Abbreviations: BMI: body mass index;
Percentages may not equal 100 due to rounding.
‡ History of or currently taking antidiabetic or lipid-lowering medications.
† History of or currently have elevated serum creatinine level but less than 4 mg/dL (<354 µmol/L).

Figure 12 - Table 3

| Symbol | SNP(s) | Forward PCR primer | Reverse PCR primer | Extension primer |
|---|---|---|---|---|
| ACE | rs4309 | TGAGATGGGCCATATACAGTACTAC [SEQ ID NO: 1] | CCCGACGCAGGGAGAC [SEQ ID NO: 2] | CTGCAGTACAAGGATCTGCC [SEQ ID NO: 6] |
| ACE | rs4343 | CCCTTACACAAGCAGAGAGGTGAGCTAA (DNA) [SEQ ID NO: 3]; ACCACCTACAGCGTGGCC (cDNA) [SEQ ID NO: 4] | CATGCCCATAACACAGGTCTTCATA TT [SEQ ID NO: 5] | GACGAATGTGATGGCCAC [SEQ ID NO: 7] |
| ACE | rs4291, rs4292 | AGGCGCTCCAAAGCTCC [SEQ ID NO: 32] | GTGATGTTGGTGTCGTGCGCCC [SEQ ID NO: 33] | rs4291: TGGCTAGAAAGGGCCTCCTCTCTTT; [SEQ ID NO: 24] rs4292: TTGAGGCCGCCGCTGAGGACT [SEQ ID NO: 25] |
| ACE | rs4290 rs7214530 rs7213516 | TTGCCCCAGCACCATTTGTTAAAAA [SEQ ID NO: 265] | TTGTATGTTACTGGAGGGCAGG GATG [SEQ ID NO: 266] | rs4290: CCTAGCACAGGGCAAAACCTCATC [SEQ ID NO: 267] rs7214530 AGGTCACCAGTTACCACAGGAGAGAAAA [SEQ ID NO: 268] rs7213516 ACAATGGAATAGAATTGAGAGTCCAGAAAT GAA [SEQ ID NO: 269] |

Oligonucleotide sequences used in genotyping and allelic expression imbalance (AEI) assays for ACE that employed primer extension technology. Underlined nucleotides were intentionally mismatched against the reference sequence.

Figure 13 - Table 4

Figure 14 - Table 5

| SNP | | | |
|---|---|---|---|
| rs4290 | C allele:<br>CACAGGGCAAAACCTCAACG<br>[SEQ ID NO: 35] | T allele:<br>GGGCGCGCCGCGGGCCCACAGGGCAAAACCTCACCA<br>[SEQ ID NO: 36] | Forward oligo:<br>GTCATTTCCTCTTCCTCTGCAC<br>[SEQ ID NO: 37] |
| rs4343 | G allele:<br>GACGAATGTGATGGCCTCG<br>[SEQ ID NO: 38] | A allele:<br>GGGCCGGCCGCGACGAATGTGATGGCCGCA<br>[SEQ ID NO: 39] | Reverse oligo:<br>CATGCCCATAACAGGTCTTCATATT<br>[SEQ ID NO: 40] |
| rs4309 | C allele:<br>TGCAGTACAAGGATCTGACC<br>[SEQ ID NO: 41] | T allele:<br>CGCCGGGCCGGGCCGGTGCAGTACAAGGATCTGGCT<br>[SEQ ID NO: 42] | Reverse oligo:<br>TCCCCAATGGCCTCATG<br>[SEQ ID NO: 43] |

Figure 15 - Table 6

| | Forward biotinylated PCR oligo | Reverse PCR oligo | Reverse sequencing oligo |
|---|---|---|---|
| rs4290 | GAGTGTGGGTCATTTCCTCTTT<br>[SEQ ID NO: 16] | AGTTTAGCATGGTGCCTAGCA<br>[SEQ ID NO: 17] | GGGCAAAACCTCATC<br>[SEQ ID NO: 18] |

| | | | |
|---|---|---|---|
| -3040F | CAGCCCCAAATTTGTATATGG [SEQ ID NO: 45] | -2235R | GTTACTGGAGGGCAGGGATG [SEQ ID NO: 46] |
| -2677F | TTCTCCTTTGTTGTGACGGC [SEQ ID NO: 47] | -1718R | TCTGTGTGCAAATGAGCTGC [SEQ ID NO: 48] |
| -1546F | TGTCCTCTGGTATCCACTGGCT [SEQ ID NO: 49] | -542R | GACCTTAGGTGTCTTGCAGGC [SEQ ID NO: 50] |
| -3040F | *amplified with -3040F, sequenced from reverse | -1287R | TCCTGTGAGATGCACCTCCAG [SEQ ID NO: 51] |
| -661F | AGGGCGCTCCAAAGCTCC [SEQ ID NO: 52] | +251R | GTGATGTTGGTGTCGTGCG [SEQ ID NO: 53] |
| +122F | CTGCAGCCCGGCAACTT [SEQ ID NO: 54] | +832R | GTATCTGTCTCCGTATCGGGCG [SEQ ID NO: 55] |
| +624F | AACCGCTGTACGAGGATTTCAC [SEQ ID NO: 56] | +1373R | CGATTTGTGCAGATGTTCAGG [SEQ ID NO: 57] |
| +1230F | TGAGATGGGCCATATACAGTACTAC [SEQ ID NO: 58] | +1938R | CCCTCCGGGTAGTTGTCAGG [SEQ ID NO: 59] |
| +1775F | CTGAAGGACATGGTCGGCTTAG [SEQ ID NO: 60] | +2506R | CCACGAGTCCCCTGCATCTAC [SEQ ID NO: 61] |
| +2312F | TGGAAACCACTACAGCGTG [SEQ ID NO: 62] | +3044R | CCCTCAAGGCCACAGGTAAGT [SEQ ID NO: 63] |
| +3025F | CTTACCTGTGGCCTTGAGGG [SEQ ID NO: 64] | +3725R | CTTCTGAGCGAGCGGAGTTC [SEQ ID NO: 65] |
| +3258F | AAGCATCACCAAGGAGAGAACTATAACC [SEQ ID NO: 66] | +4174R | TGTATTCACAGAGAGACTTGGAGAGGT [SEQ ID NO: 67] |
| 3'UTRfwd | GAACACTTGCCATTTGAGCC [SEQ ID NO: 68] | 3'UTRrev | AGGATGGAGGAACAAACCTAGTAAC [SEQ ID NO: 69] |

Figure 16 - Table 7

| Polymorphism | FAM-labeled PCR primer | Matching PCR primer(s) | Post-PCR treatment |
|---|---|---|---|
| rs7213516 | FAM-GCCCCAGCACCATTTGTTAA [SEQ ID NO: 44] | CAGAGACCTGACCCACGTGAG [SEQ ID NO: 15] | *Hinf*I enzyme digest, Capillary electrophoresis |
| rs13447447 (287 bp ALU I/D) | FAM-GTGGCCATCACATTCGTCAG [SEQ ID NO: 19] | 2 primer multiplex: CCCATCCTTTCTCCCCATTTCT [SEQ ID NO: 20]; GACCTCGTGATCCGCCC [SEQ ID NO: 21] | Capillary electrophoresis |
| rs4366 | FAM-TGGCTCCTGCCTGTACCAG [SEQ ID NO: 22] | CCAAGGCTGTTCACCCGA [SEQ ID NO: 23] | Capillary electrophoresis |

Figure 17 - Table 8

| PCR primer | Exon spanning PCR primer |
|---|---|
| CCCCTTCCGCGCTACAACTT [SEQ ID NO: 8] | TCCCCTGATACTTGGTTCGAA [SEQ ID NO: 9] |

Figure 18 - Table 9

| Symbol | SNP(s) | Forward PCR primer | Reverse PCR primer | Extension primer |
|---|---|---|---|---|
| SOD2 | rs4880 | GGTTGTTCACGTAGGCCG [SEQ ID NO: 79] | CAGCAGGCAGCTGGCT [SEQ ID NO: 80] | GAGCCCAGATACCCCAAA [SEQ ID NO: 81] |
| | rs5746092 | TTGCGGGCGCAGCTGG [SEQ ID NO: 82] | CTGAAGCCGCTGCCGA A [SEQ ID NO: 83] | GGGCCTTAAGAAAGCGC [SEQ ID NO: 84] |

Figure 19 - Table 10

| Gene | rs# | Sequence |
|---|---|---|
| SLC6A3 (DAT) | rs27072 | AGTGCCCCTGGGGCAGCCTCAGAGC [C/T] GGGAGCAGGGAGCAGGGAGG [SEQ ID NO: 85] |
| SLC6A3 (DAT) | rs6347 | CCATCGCCAGCTCCCCTCTG TCCTC [A/G] GCCTGGGCCGTGGTCTTCTT [SEQ ID NO: 86] |

Figure 20 - Table 11

| Gene | rs# | Sequence |
|---|---|---|
| CYP2C9 | rs1057911 | CTTGACACCACTCCAGTTGTCAATGG[A/T]TTTGCCTCTGTGCCGCCCTTCTACC [SEQ ID NO: 90] |

Figure 21 - Table 12

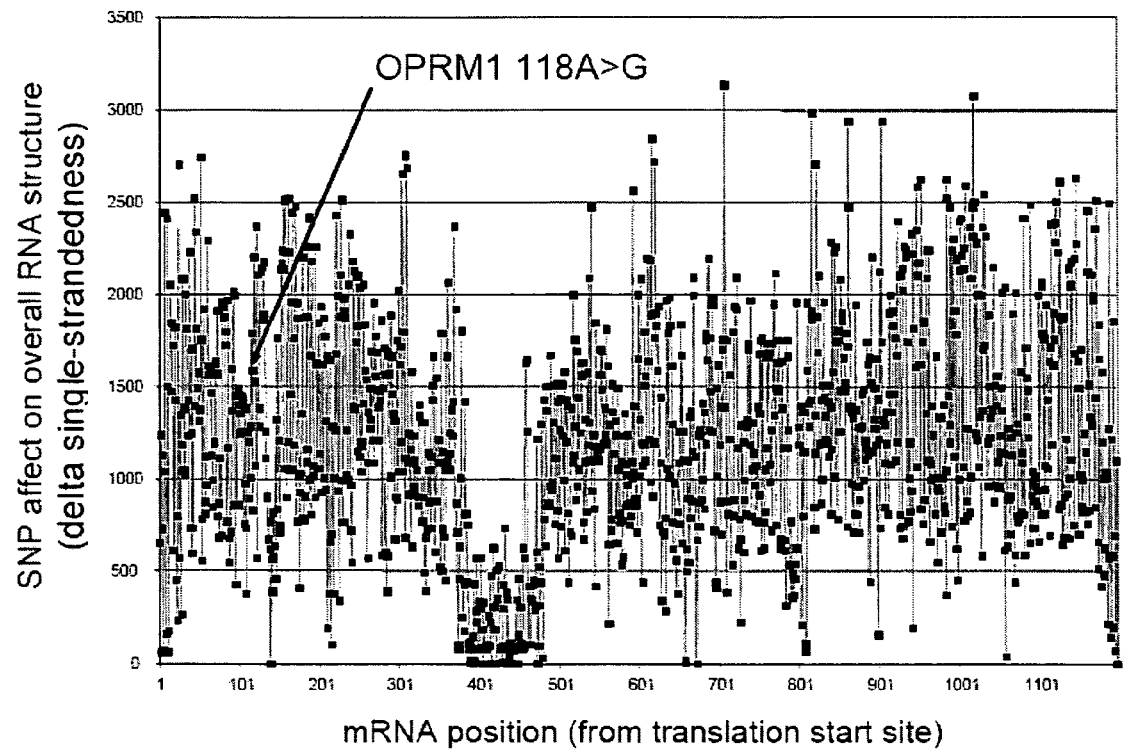

Figure 25

| Cardiovascular disease and pharmacogenetic candidate genes |
|---|
| ACE, CCL2, SOD2, NNMT, LPL, HMGCR, CSF1, PTGDS, HIF1A, NOS3, FLT1, CACNA1C, ADRB2, KCNMB1, VKORC1, GGCX, CETP, HMOX1 |
| |
| Drug metabolism and drug transporter candidate genes |
| ABCB1, CYP2D6, CYP2C9, SLC15A1, SLC15A2 |
| |
| CNS disorder and pharmacogenetics candidate genes |
| RD2, CHRNA4, OPRM1, HTR2A, BDNF, SLC6A4, TPH2, SLC6A2, DTNBP1, NRG1, HTR1B, MAOA, DRD3, ESR1, SLC6A3 (DAT), COMT, DAO, NR3C1, NQO2 |

Figure 26 - Table 13

| Symbol | Tissue | Marker SNP(s) | AEI ratio range | % samples with significant AEI (total number of samples) | Further publication |
|---|---|---|---|---|---|
| Cardiovascular disease candidate genes | | | | | |
| ACE | Heart, Liver, Small bowel | rs4309<br>rs4343 | 0.2-1.5 | 48% (n=73) | |
| MCP1/CCL2 | Heart, Monocytes | rs4586<br>rs13900 | 0.66-1.87 | 18% (n=55) | |
| SOD2 | Heart | rs4880<br>rs5746092 | 0.9-2.1 | 83% (n=41) | |
| NNMT | Liver, Small bowel | rs4646335 | 0.58-2.9 | 15% (n=39) | |
| CSF1 | Monocytes | rs333970 | 0.98-1.9 | 11% (n=18) | |
| PTGDS | Heart | rs6926 | 0.7-1.3 | 3% (n=30) | |
| NOS3 | Heart | rs1799983 | 0.65-1.11 | 18% (n=22) | |
| VKORC1 | Liver | rs7294 | 0.5-1 | 68% (n=29) | |
| CETP | Liver | rs5884 | 0.67-1.89 | 77% (n=29) | |
| Drug metabolism candidate genes | | | | | |
| ABCB1 | Liver | rs1045642<br>rs1128503<br>rs2032582 | 1.0-1.6 | 36% (n=22) | [9] |
| CYP2D6 | Liver | rs1065852<br>rs1058164<br>rs16947<br>rs1135840 | 0.1-10 | 88% (n=26) | |
| CYP2C9 | Liver | rs2017319 | 0.6-1.2 | 21% (n=19) | |
| SLC15A2 | Kidney | rs1143670<br>rs1143671 | 0.6-1.1 | 13% (n=8) | |

Figure 27 - Table 4

| | | CNS disorder candidate | | | |
|---|---|---|---|---|---|
| DRD2 | Brain | rs6277 | 0.5-2.0 | 25% (n=30) | [16] |
| | | rs6275 | | | |
| | | rs6279 | | | |
| CHRNA4 | Brain | rs1044393 | 0.6-2.0 | 85% (n=13) | |
| | | rs1044397 | | | |
| | | rs2229959 | | | |
| | | rs2236196 | | | |
| OPRM1 | Brain | rs1799971 | 1.0-3.0 | 100% (n=8) | [10] |
| BDNF | Brain | rs6265 | 0.9-1.6 | 11% (n=9) | |
| TPH2 | Brain | rs7305115 | 0.92-2.55 | 48% (n=27) | [13] |
| | | rs4290270 | | | |
| DTNBP1 | Brain | rs1047631 | 0.88-1.45 | 22% (n=9) | |
| MAOA | Brain | rs1137070 | 0.3-4.0 | 89% (n=19) | [12] |
| | | rs6232 | | | |
| DRD3 | Brain | rs6280 | 0.3-2.7 | 57% (n=21) | |
| ESR1 | Brain | rs3798577 | 0.5-1.7 | 24% (n=46) | |
| SLC6A3 (DAT) | Brain | rs6347 | 0.1-1.2 | 95% (n=21) | |
| COMT | Brain | rs4633 | 0.9-1.4 | 10% (n=10) | |
| DAO | Brain | rs2070588 | 0.3-4.5 | 57% (n=21) | |
| NR3C1 | Brain | rs6196 | 0.4-1.0 | 5% (n=20) | |
| NQO2 | Coriell sample | rs1143684 | 0.88-2.60 | 33% (n=9) | |

AEI ratios are defined by mRNA abundance of major over minor allele for a given marker SNP (normalized to genomic allele ratios measured with SNaPshot).
Frequency of AEI is given as % of total number of samples heterozygous for the marker SNP(s).
Direction of AEI ratios can be determined by the range of values observed (e.g., >1, <1, and <1>), indicating the minor allele is less or more abundant, respectively.
For several genes, references provide detailed AEI studies published separately.

Figure 27 - Table 4 (continued)

| Gene | Suspected functional polymorphism/ marker | Literature reference | Heterozygous with AEI | Heterozygous without AEI | Homozygous with AEI | Homozygous without AEI | Kappa correlation coefficient (0.5 cutoff) | Kappa correlation coefficient (0.2 cutoff) | p-value (AEI as continuous) |
|---|---|---|---|---|---|---|---|---|---|
| ACE | Intron 16 I/D | [39] | 2 | 21 | 3 | 6 | -0.15 | -0.43 | 0.04 |
| CCL2 | rs1024611 (macrophages) | [32] | 2 | 24 | 0 | 8 | 0.04 | 0.04 | 0.95 |
| CCL2 | rs1024611 (heart) | [32] | 1 | 26 | 1 | 5 | -0.05 | 0.19 | 0.82 |
| NOS3 | rs2070744 | [51] | 3 | 9 | 0 | 5 | 0.16 | -0.02 | 0.66 |
| PTGDS | rs6296 | n/a | 1 | 29 | n/a | n/a | n/a | n/a | n/a |
| SOD2 | rs4880 | [41] | 27 | 7 | 7 | 0 | -0.21 | -0.11 | 0.67 |
| SOD2 | rs5746092 | n/a | 21 | 8 | 13 | 4 | -0.04 | 0.20 | 0.71 |
| SOD2 | rs5746091 | [33] | 3 | 0 | 4 | 3 | n/a | n/a | n/a |

Association between heterozygosity of the suggested variants and AEI was done with AEI ratios as a categorical variable using the Kappa test with AEI cutoff (±log2 0.5).
The number of subjects heterozygous or homozygous with or without AEI at the 0.5 cutoff is given.
Alternatively we applied a relaxed cutoff (±log2 0.2) to address the possibility that lower, but detectable AEI may also be significant (counts not shown).
We also tested for association with AEI as a continuous measure using HelixTree (taking the absolute value of AEI for each sample).
Tests considered significant at p<0.05 are indicated in bold.
We did not test rs6296 or rs5746091 for association (listed as "n/a") given low numbers of heterozygous and/or homozygous samples.

Figure 28 - Table 15

| Name | Symbol | Indication | Tissue (number of heterozygous subjects) | Marker SNP | % het | Replicates (n) or assay validation |
|---|---|---|---|---|---|---|
| Cardiovascular disease candidate genes | | | | | | |
| Angiotensin I converting enzyme | ACE | Blood pressure, CAD | Heart (31) Small bowel (32) Liver (10) | rs4309 (exon 9) | 51 37 53 | 6 4 4 |
| | | | | rs4343 (exon 17) | 40 | 6 |
| Monocyte chemoattractant protein 1 | CCL2 | CAD, SLE, inflammation, infection | Heart (29) Monocytes (26) | rs4586 (exon 2) | 45 | 4 |
| | | | | rs13900 (3'UTR) | 46 | 4 |
| Superoxide dismutase, mitochondrial | SOD2 | Oxidative stress, cancer | Heart (34) | rs4880 (exon 2) | 52 | 4 |
| | | | | rs5746092 (5'UTR) | 38 | 4 |
| Nicotinamide N-methyltransferase | NNMT | Homocysteine levels | Liver (19) Small bowel (20) | rs4646335 (exon 1) | 33 | 2 |
| Lipoprotein lipase | LPL | Triglyceride, cholesterol metabolism | Heart (15) | rs1059611 (exon 10) | 23 | 3 |
| 3-hydroxy-3-methylglutaryl-CoA reductase | HMGCR | Cholesterol synthesis, direct target (statins) | Liver (8) B-lymph (18) | rs12916 (exon 19) | 23 20 | 1 1 |
| Colony-stimulating factor, macrophage-specific | CSF1 | Inflammation, endothelial function | Monocytes (18) | rs333970 (exon 6) | 43 | 4 |
| Prostaglandin D2 synthase | PTGDS | CAD | Heart (30) | rs6926 (exon 7) | 46 | 2 |
| Hypoxia-inducible factor 1, alpha subunit | HIF1A | Oxidative stress | Heart (18) | rs2057482 (exon 15) | 28 | 2 |
| Nitric oxide synthase, endothelial | NOS3 | Oxidative stress, vascular function | Heart (22) | rs1799983 (exon 8) | 34 | 4 |
| FMS-related tyrosine kinase | FLT1 | Endothelial function | Heart (19) | rs2296189 (exon 23) | 29 | 2 |
| L-type voltage-dependent calcium channel alpha subunit 1C | CACNA1C | Blood pressure | Heart (37) | rs1544514 (exon 4) | 27 | 6 |
| | | | | rs216008 (exon 30) | 40 | 6 |
| Adrenergic receptor beta2 | ADRB2 | Blood pressure | Heart (22) | rs1042719 (exon1) | 46 | 2 |
| BK channel beta1 subunit | KCNMB1 | Blood pressure | Heart (30) | rs11739136 (exon 3) | 12 | 6 |
| | | | | rs2656842 (exon 4) | 46 | 6 |
| | | | | rs2656841 (exon 4) | 47 | 6 |
| Vitamin K epoxide reductase | VKORC1 | Warfarin target | Liver (29) Heart (26) B-lymph (12) | rs7294 (exon 3, 3'UTR) | 40 | 6 |
| Gamma-glutamyl carboxylase | GGCX | Blood coagulation | Liver (23) | rs699664 (exon 8) | 40 | 2 |
| Cholesteryl ester transfer protein | CETP | HDL cholesterol remodeling | Liver (29) | rs5884 (exon 14) | 47 | 6 |
| Heme oxygenase 1 | HMOX1 | Heme catabolism | Heart (5) | rs11555832 (3'UTR) | 8 | 1 |

Figure 29 Table 16

| Name | Symbol | Indication | Tissue (number of heterozygous subjects) | Marker SNP | % het | Replicates (n) or assay validation |
|---|---|---|---|---|---|---|
| Drug metabolism candidate genes | | | | | | |
| Multidrug resistance polypeptide 1, MDR1 | ABCB1 | Drug transporter | Liver (22) | rs1045642 (exon 26) | 50 | 6 |
| | | | | rs1128503 (exon 12) | 44 | 6 |
| | | | | rs2032582 (exon 21) | 47 | 6 |
| Cytochrome P450, subfamily 2D, polypeptide 6 | CYP2D6 | Drug metabolism | Liver (26) | rs1065852 (exon 1) | 26 | 6 |
| | | | | rs1058164 (exon 3) | 32 | 6 |
| | | | | rs16947 (exon 6) | 37 | 6 |
| | | | | rs1135840 (exon 9) | 30 | 6 |
| Cytochrome P450, subfamily 2C, polypeptide 9 | CYP2C9 | Drug metabolism | Liver (19) | rs9332242 (exon 9) | 11 | 4 |
| | | | | rs1057911 (exon 9) | 9 | 4 |
| Human peptide transporter 1 | SLC15A1 | Transporter | Small bowel (21) | rs1339067 (exon 17) | 42 | 4 |
| Human peptide transporter 2 | SLC15A2 | Transporter | Kidney (8) | rs1143670 (exon 14) | 45 | 4 |
| | | | | rs1143671 (exon 15) | 45 | 4 |
| CNS disorder candidate genes | | | | | | |
| Dopamine D2 receptor | DRD2 | CNS | Prefrontal cortex, all lobes (30) | rs6277 (exon 7) | 44 | 6 |
| | | | | rs6275 (exon 7) | 33 | 4 |
| | | | | rs6279 (3' UTR) | 31 | 6 |
| Acetylcholine nicotinic receptor subunit a4 | CHRNA4 | CNS | Striatum (13) | rs1044393 (exon 5) | 20 | 4 |
| | | | | rs1044397 (exon 5) | 40 | 4 |
| | | | | rs2236196 (3' UTR) | 44 | 4 |
| mu Opioid receptor | OPRM1 | CNS | All lobes, Pons (8) | rs1799971 (exon 1) | 8 | 6 |
| Serotonin receptor 2A | HTR2A | CNS | Prefrontal cortex (16) | rs6313 (exon 1) | 15 | 2 |
| Brain-derived neurotrophic | BDNF | CNS | All lobes (9) | rs6265 (exon 2) | 35 | 4 |
| Serotonin transporter | SLC6A4 | CNS | Pons (29) | rs1042173 (3'UTR) | 60 | 3 |
| Tryptophan hydroxylase 2 | TPH2 | CNS | Pons (27) | rs7305115 (exon 7) | 38 | 4 |
| | | | | rs4290270 (exon 9) | 46 | 2 |
| Norepinephrine transporter | SLC6A2 | CNS | Pons (18) | rs5569 (exon 9) | 38 | 2 |
| Dysbindin 1 | DTNBP1 | CNS | Pons (9) | rs1047631(3'UTR) | 15 | 2 |
| Neuregulin 1 | NRG1 | CNS | Pons (8) | SNP8NRG433E1006 (exon 1) | 17 | 2 |
| Serotonin receptor 1B | HTR1B | CNS | Pons (16) | rs6296 (exon 1) | 33 | |
| Monoamine oxidase A | MAOA | CNS | Prefrontal cortex (19) | rs1137070 (exon 14) | 47 | 3 |
| | | | | rs6323 (exon 8) | 50 | 3 |
| Dopamine D3 receptor | DRD3 | CNS | Prefrontal cortex (21) | rs6280 (exon 2) | 38 | 3 |
| Estrogen receptor | ESR1 | CNS | Prefrontal cortex (46) | rs3798577 (3'UTR) | 44 | 3 |
| Dopamine transporter | SLC6A3 (DAT) | CNS | Striatum (21) | rs6347 (exon 9) | 54 | 3 |
| Catechol-O-methyltransferase | COMT | CNS | Prefrontal cortex (10) | rs4633 (exon 3) | 65 | 1 |
| Diamine oxidase | DAO | CNS | Prefrontal cortex (21) | rs2070588 (5'UTR) | 37 | 3 |
| Glucocorticoid receptor | NR3C1 | CNS/stress hormonal | Prefrontal cortex (20) | rs6196 (exon 8) | 19 | 3 |
| Nad(p)h:menadione oxidoreductase 1, dioxin-inducible 2 | NQO2 | CNS | B-lymph (9) | rs1143684 (exon 3) | 30 | 1 |

Figure 29 - Table 16 (continued)

| Symbol | Marker SNP(s) | Forward PCR primer | Reverse PCR primer | Extension primer |
|---|---|---|---|---|
| ACE | rs4309 | 5'TGAGATGGGCCATATACAGTAGTACTAC3' [SEQ ID NO: 1] | 5'CCCGACGCAGGGGAGAC3' [SEQ ID NO: 2] | 5'CTGCAGTACAAGGATCTGCC3' [SEQ ID NO: 6] |
| | rs4343 | 5'CCCTTACAAGCAGAGGTGAGCTA3' (DNA) [SEQ ID NO: 3]  5'ACCACCTACAGCGTGGCC3' (cDNA) [SEQ ID NO: 4] | 5'CATGCCCATAACAGGTCTTCATATT3' [SEQ ID NO: 5] | 5'GACGAATGTGATGGCCAC3' [SEQ ID NO: 7] |
| SOD2 | rs4880 | 5'GGTTGTTCACGTAGGCCG3' [SEQ ID NO: 79] | 5'CAGCAGGCAGCTGGCT3' [SEQ ID NO: 80] | 5'GAGCCCAGATACCCCAAA3' [SEQ ID NO: 81] |
| | rs5746092 | 5'TTGCGGCGCAGCTGG3' [SEQ ID NO: 82] | 5'CTGAAGCGCTGCCGAA3' [SEQ ID NO: 83] | 5'GGGCCTTAAGAAAGCGC3' [SEQ ID NO: 84] |
| SLC6A3 (DAT) | rs6347 | 5'TTCATCATCTACCCGGAAGCC3' [SEQ ID NO: 87] | 5'GAAGAAGACCACGGCCCAG3' [SEQ ID NO: 88] | 5'ACGCTCCCTCTGTCCTC3' [SEQ ID NO: 89] |
| CYP2C9 | rs9332242 | 5'GGATTTGTGTGGGAGAAGCC3' [SEQ ID NO: 91] | 5'TAGTGAAAGATGGATAATGCCCCA3' [SEQ ID NO: 92] | 5'AATGCCTTTTCTCACCTGTCATCT3' [SEQ ID NO: 93] |
| CYP2C9 | rs2017319 | 5'GGATTTGTGTGGGAGAAGCC3' [SEQ ID NO: 94] | 5'TAGTGAAAGATGGATAATGCCCCA3' [SEQ ID NO: 95] | 5'AGGAATAAAAACAGCTCCATGCC3' [SEQ ID NO: 96] |
| MCP1 (CCL2) | rs4586 | 5'ATGCAATCAATGCCCCAGTC3' [SEQ ID NO: 97] | 5'GCGAGCCTCTGCACTGAGAT3' [SEQ ID NO: 98] | 5'AGATCTTCCTATTGGTGAAGTTATA3' [SEQ ID NO: 99] |
| | rs13900 | 5'CAACCCAAGAATCTGCAGCTAA3' [SEQ ID NO: 100] | 5'GGCATAATGTTTCACATCAACAAAC3' [SEQ ID NO: 101] | 5'TAGCTTTCCCCAGACACC3' [SEQ ID NO: 102] |
| NNMT | rs4646335 | 5'GTCCTGTCTCTGAACTTTGGG3' [SEQ ID NO: 103] | 5'GAGCTGTATGCAATGCTTGCC3' [SEQ ID NO: 104] | 5'ATTGTAGACCAGAGGGAGCACT3' [SEQ ID NO: 105] |

Figure 30 - Table 17

| | | | |
|---|---|---|---|
| LPL | rs1059611 | 5'TAAAGCAGCAGCACATAGCACTGG3' [SEQ ID NO: 106] | 5'GCAGATAGCCACAATGACCTT3' [SEQ ID NO: 107] | 5'CCTTTCCAATATGTACAAGCTCC3' [SEQ ID NO: 108] |
| HMGCR | rs12916 | 5'GCAAATATAAGCTGGGAAAAAGTTT3' [SEQ ID NO: 109] | 5'AATTAACTACAAAATCAGGAGTTTCATCAG3' [SEQ ID NO: 110] | 5'AAATCCATTTTCAACTGGCAGG3' [SEQ ID NO: 111] |
| CSF1 | rs333970 | 5'TTCCTCTCAGCATCTTCTCCAC3' [SEQ ID NO: 112] | 5'GGGCAGAGATGGATGGTCTGTC3' [SEQ ID NO: 113] | 5'GCCGGCAGATGTAACTGGTAC3' [SEQ ID NO: 114] |
| PTGDS | rs6926 | 5'GGGCTGAAGCTGGGATC3' [SEQ ID NO: 115] | 5'CTGACTTGCTTCCGGAGTTT3' [SEQ ID NO: 116] | 5'CTCCCCGCCAAAGCA3' [SEQ ID NO: 117] |
| HIF1A | rs2057482 | 5'CATTCCTTTTTTGGACACTGGT3' [SEQ ID NO: 118] | 5'CAAGTTTGTGCAGTATTGTAGCCA3' [SEQ ID NO: 119] | 5'ATGTAGAAAATATAAATAGACTGCTTTAGGTA3' [SEQ ID NO: 120] |
| NOS3 | rs1799983 | 5'GAAACGGTCGCTTCGACGT3' [SEQ ID NO: 121] | 5'GGCAGAAGGAAGAGTTCTGGG3' [SEQ ID NO: 122] | 5'AGTAACCTTGGAACCTTGGTGCAGGCCCCAGATGA3' [SEQ ID NO: 123] |
| FLT1 | rs2296189 | 5'AATACTCCGTAAGACCACACGTC3' [SEQ ID NO: 124] | 5'ACTCGACTTCCTCTGAAATGGA3' [SEQ ID NO: 125] | 5'GCTGTGTAGATTTTGTCAAAGATAGATTC3' [SEQ ID NO: 126] |
| CACNA1C | rs1544514 | 5'GAACGAGTGGAATATCTCTTTCTCATAA3' [SEQ ID NO: 127] | 5'GCGGAGGTAGGCATTGGG3' [SEQ ID NO: 128] | 5'CATAATTTTACGGTGGAAGC3' [SEQ ID NO: 129] |
| | rs216008 | 5'CCAGAGCTGCCCTGTTCAAAAT3' [SEQ ID NO: 130] | 5'ATGAGCTTCAGGATCATCTCCAC3' [SEQ ID NO: 131] | 5'TGCTCTTCACTGGCCTCTT3' [SEQ ID NO: 132] |
| ADRB2 | rs1042719 | 5'TTCCAGGAGCTTCTGTGCCT3' [SEQ ID NO: 133] | 5'GCCGTTGCTGGAGTAGCC3' [SEQ ID NO: 134] | 5'TCTTCTTTGAAGGCCTATGG3' [SEQ ID NO: 135] |
| KCNMB1 | rs11739136 | 5'CAGGAATCCAAGTGCCACC3' [SEQ ID NO: 136] | 5'CCACAGGCATGGTACTGG3' [SEQ ID NO: 137] | 5'CCAAACATCAGGGACCAGGAG3' [SEQ ID NO: 138] |
| | rs2656842 | 5'AAGTAGAGCCATCCATCCATGC3' [SEQ ID NO: 139] | 5'GATTGGACTGGAAGAGTGGG3' [SEQ ID NO: 140] | 5'CTGCTCCCCACTTGCAG3' [SEQ ID NO: 141] |
| VKORC1 | rs7294 | 5'TTTTCCTAACTCGCCCGCT3' [SEQ ID NO: 142] | 5'TGGGTGTAAAAAGAGCGAGC3' [SEQ ID NO: 143] | 5'CCTCCTCCTGCCATACCC3' [SEQ ID NO: 144] |

Figure 30 - Table 17 (continued)

| Gene | rs ID | Sequence 1 | Sequence 2 |
|---|---|---|---|
| GGCX | rs699664 | 5'GAGTGGCCTCGGAAGCTG3' [SEQ ID NO: 145] | 5'GGAAACACTGGGCTGAGGG3' [SEQ ID NO: 146] | 5'GGTGTCCTACTGCCCCC3' [SEQ ID NO: 147] |
| CETP | rs5884 | 5'TCACCATGGGCATTTGATT3' [SEQ ID NO: 148] | 5'CCACAGCGGT GATCATTGAC3' [SEQ ID NO: 149] | 5'TGAGAGCAGCTCCGAGTCC3' [SEQ ID NO: 150] |
| HMOX1 | Rs1155583 2 | 5'GGAGGTTTGAGACAGCTGCC3' [SEQ ID NO: 151] | 5'CTGCAGCAGAGCCTGGAAG3' [SEQ ID NO: 152] | 5'CTGCAGCAGAGCCTGGAAG3' [SEQ ID NO: 153] |
| ABCB1 | rs1045642 | 5'CCTATGGAGACAACAGCCGG3' [SEQ ID NO: 154] | 5'GGCATGTATGTTGGCCTCCT3' [SEQ ID NO: 155] | 5'CTCCTTTGCTGCCCTCAC3' [SEQ ID NO: 156] |
| | rs1128503 | 5'TTTCTCACTCGTCCTGGTAGATCT 3' [SEQ ID NO: 157] | 5'ACTGTTTCCAACCAGGGCC3' [SEQ ID NO: 158] | 5'CTCTGCACCTTCAGGTTCAG3' [SEQ ID NO: 159] |
| | rs2032582 | 5'TGTTGAAATGAAAATGTGTCTG G3' [SEQ ID NO: 160] | 5'CAATCATATTTAGTTTGACTCACCTTCC 3' [SEQ ID NO: 161] | 5'TGAAAGATAAGAAAGAAACTAGAA GGT3' [SEQ ID NO: 162] |
| | rs2656841 | 5'AAGTAGAGCCATCCATCCATGC3' [SEQ ID NO: 163] | 5'GATTGGACTGGAAGAGTGGG3' [SEQ ID NO: 164] | 5'GCAGGTGGAGAAGGCATTG3' [SEQ ID NO: 165] |
| CYP2D6 | rs769258 | 5'TGTGTCCAGAGGAGCCCAT3' [SEQ ID NO: 166] | 5'GGCTCACCAGCAGGAAAAGCAAA3' [SEQ ID NO: 167] | 5'ACCGCCCGCCCTGTGCCCATCA3' [SEQ ID NO: 168] |
| | rs1058164 | 5'TGTGTCCAGAGGAGCCCAT3' [SEQ ID NO: 169] | 5'GGCTCACCAGCAGGAAAAGCAAA3' [SEQ ID NO: 170] | 5'CGAGCAGAGGCGCTTCTCCGT3' [SEQ ID NO: 171] |
| | rs16947 | 5'TGTGTCCAGAGGAGCCCAT3' [SEQ ID NO: 172] | 5'GGCTCACCAGCAGGAAAAGCAAA3' [SEQ ID NO: 173] | 5'AGCTTCAATGATGAGAACCTG3 [SEQ ID NO: 174] |
| | rs1135840 | 5'GGCCCCAGCCACCATG3' [SEQ ID NO: 175] | 5'GCACAGCACAAAGCTCATAGGG3' [SEQ ID NO: 176] | 5'GTGTCTTTGCTTTCCTGGTGA3' [SEQ ID NO: 177] |
| SLC15A1 | rs1339067 | 5'ACATTTCTTCTCCTGGATCACCA3' [SEQ ID NO: 178] | 5'ACACTAGAAGCGTGTGGCGTT3' [SEQ ID NO: 179] | F: 5'CTGGATCACCAGTCACTGC3' [SEQ ID NO: 180] R: 5'CTGCTTGAAGTCGTCAGTTAC3' [SEQ ID NO: 181] |
| SLC15A2 | rs1143670 | 5'AGGAAAATGGCTGTTGGTATGATC 3' [SEQ ID NO: 182] | 5'CGCAACTGCAAATGCCAG3' [SEQ ID NO: 183] | 5'GCTGTTGGTATGATCCTAGC3' [SEQ ID NO: 184] |

Figure 30 - Table 17 (continued)

| Gene | SNP | | | |
|---|---|---|---|---|
| DRD2 | rs1143671 | 5'GAAATGGCCCCAGCCC3' [SEQ ID NO: 185] | 5'CATCTGCCAGATTCAAGACTTGTAG3' [SEQ ID NO: 186] | 5'AACCTCCTGGGGACCTG3' [SEQ ID NO: 187] |
| | rs6277 | 5'CCAGCTGACTCTCCCCGAC3' [SEQ ID NO: 188] | 5'GCATGCCCATTCTTCTCTGG3' [SEQ ID NO: 189] | 5'CGATCACATGTCGTGAACTGAC TGACTGGTTTGGCGGGGCTGTC3' [SEQ ID NO: 190] |
| | rs6275 | 5'CCAGCTGACTCTCCCCGAC3' [SEQ ID NO: 191] | 5'GCATGCCCATTCTTCTCTGG3' [SEQ ID NO: 192] | 5'GGAGTGCTGTGGAGACC3' [SEQ ID NO: 193] |
| | rs6279 | 5'AGCCTGAGTCAGGGCCC3' [SEQ ID NO: 194] | 5'ACCGCCTGCTCCACG3' [SEQ ID NO: 195] | 5'CCCAGAGGCTGAGTTTTCT3' [SEQ ID NO: 196] |
| CHRNA4 | rs1044393 | 5' TGAACATGCACAGCCGC3' [SEQ ID NO: 197] | 5' CGAAGGCATAGGTGATGTCC3' [SEQ ID NO: 198] | 5'TTGTAGGTGCCCACGGC3' [SEQ ID NO: 199] |
| | rs1044397 | 5'CACATGCAAGAAGGAGCCCT3' [SEQ ID NO: 200] | 5' GGTGGTCTGCAATGTACTGGA3' SEQ ID NO: 201] | 5'CCGCAGCACCAAAGC3' SEQ ID NO: 202] |
| | rs2236196 | 5' CCCTCTCCTAGCGAAGCAGAT3' SEQ ID NO: 203] | 5' GGTCCTTGAGCCTCTCGGG3' SEQ ID NO: 204] | 5'CTAGCGAAGCAGATTGGAGC3' SEQ ID NO: 205] |
| OPRM1 | rs1799971 | 5'CCGTCAGTACCATGGACAGC3' SEQ ID NO: 206] | 5'GAGTACGCCAAGGCATCAGT3' SEQ ID NO: 207] | F: 5'ACTGATGACTGACTTGTCCCACTTAG ATGGC3' SEQ ID NO: 208] R: 5'ACTGACTGACTGACCATGGGTC GGACAGGT3' SEQ ID NO: 209] |
| HTR2A | rs6313 | 5'GACACCAGGCTCTACAGTAATGA CTTT3' SEQ ID NO: 210] | 5'TGTCCAGTTAAATGCATCAGAAGTG3' SEQ ID NO: 211] | 5'ACTGACTGACTGGAACCTTGAC TCATCAGAAGTGTTAGCTTCTCC3' SEQ ID NO: 212] |
| BDNF | rs6265 | 5'GCTTGACATCATTGGCTGACA3' SEQ ID NO: 213] | 5'CTGGTCCTCATCCAACAGCTC3' SEQ ID NO: 214] | 5'AACCTTGGAACCTTGGGGCTGA CACT3' SEQ ID NO: 215] |
| SLC6A4 | rs1042173 | 5'TATCTGTTTGCTTCTAAAGGTTTC3' SEQ ID NO: 216] | 5'TGGACACACTATTTTCATTTTAG SEQ ID NO: 217] | 5'GGTTCTAGTAGATTCCAGCAATA AAATT3' SEQ ID NO: 218] |

Figure 30 - Table 17 (continued)

| Gene | SNP | Sequence 1 | Sequence 2 | Sequence 3 |
|---|---|---|---|---|
| TPH2 | rs7305115 | 5'ACGAGACTTTCTGGCAGGACTG3' [SEQ ID NO: 219] | 5'TTAATTCTCCAATGGAGGAAAGGA3' [SEQ ID NO: 220] | 5'GATCCCCTCTACACCCC3' [SEQ ID NO: 221] |
|  | rs4290270 | 5'ACGAGACTTTCTGGCAGGACTG3' [SEQ ID NO: 222] | 5'TTAATTCTCCAATGGAGGAAAGGA3' [SEQ ID NO: 223] | 5'AAAGGAGTCCTGCTCCATA3' [SEQ ID NO: 224] |
| SLC6A2 | rs5569 | 5'ATGGGAGGCATGGAGGCTGTC3' [SEQ ID NO: 225] | 5'CGAGAAGGAAAGTGCTGAAGGTGAC3' [SEQ ID NO: 226] | 5'GGCATGGAGGCTGTCATCAC3' [SEQ ID NO: 227] |
| DTNBP1 | rs1047631 | 5'ATCCAGTTTTGGCTGTATGC3' [SEQ ID NO: 228] | 5'CTGTTCTTTAAGTTTCTCACACATT3' [SEQ ID NO: 229] | 5'TGTTTTATAGAGGTTCTTGATTTTAC3' [SEQ ID NO: 230] |
| NRG1 | SNP8NRG433 E1006 | 5'CTGCTGCCACTACTGCTGCTGCT3' [SEQ ID NO: 231] | 5'CACCTTTCCCTCGATCACCA3' [SEQ ID NO: 232] | 5'AGCACACCGAGGCCC3' [SEQ ID NO: 233] |
| HTR1B | rs6296 | 5'CCACGTCCTCGGTCACCTCTATTAAC3' [SEQ ID NO: 234] | 5'CACAATAAAGGCTCCCAAAATGATCC3' [SEQ ID NO: 235] | 5'TCGAAATCCGGATCTCCTGTGTATGT3' [SEQ ID NO: 236] |
| MAOA | rs1137070 | 5'AAATGGTCTCGGGAAAGGTGA3' [SEQ ID NO: 237] | 5'TTTGATTCAGGTTCTTGTACCCAG3' [SEQ ID NO: 238] | 5'GGAAGGTGACCGAGAAAGA3' [SEQ ID NO: 239] |
|  | rs6323 | 5'ACTTCAGACCAGAGCTTCCAGC3' [SEQ ID NO: 240] | 5'ATGCACTTAATGACAGCTCCCA3' [SEQ ID NO: 241] | 5'GAGAAACCAGTTAATTCAGCG3' [SEQ ID NO: 242] |
| DRD3 | rs6280 | 5'TCTGCCCCACAGGTGTAGTTC3' [SEQ ID NO: 243] | 5'GGCATCTCTGAGCCAGTTC3' [SEQ ID NO: 244] | 5'ATCTCTGAGCCAGCTGAGT3' [SEQ ID NO: 245] |
| ESR1 | rs3798577 | 5'TGGTGTTGCATTTAGCCCCTGG3' [SEQ ID NO: 246] | 5'AGCCACAACAATCCTGCACA3' [SEQ ID NO: 247] | 5'GGCATGGAGCTGAACAGTAC3' [SEQ ID NO: 248] |
| COMT | rs4633 | 5'GTGACACCAAGGAGCAGCG3' [SEQ ID NO: 249] | 5'TGTCAATGGCCTCCAGCAC3' [SEQ ID NO: 250] | 5'AGCGCATCCTGAACCA3' [SEQ ID NO: 251] |
| DAO | rs2070588 | 5'GACGGGACTGATAACAGCAGC3' [SEQ ID NO: 252] | 5'CACAAGCATCCATTCATCCAA3' [SEQ ID NO: 253] | 5'CATCCAAGTCTCCCAACACT3' [SEQ ID NO: 254] |
| NR3C1 | rs6196 | 5'GGCAGTCACTTTTGATGAAACAGA3' [SEQ ID NO: 255] | 5'GAGTATTGAATTCCCCGAGATGTTAG3' [SEQ ID NO: 256] | 5'CAATCAGATACCAAAATATTCAAA3' [SEQ ID NO: 257] |
| NQO2 | rs1143684 | 5'GCTGCACCGTCACAGTGTCT3' [SEQ ID NO: 258] | 5'TGATATCTTTGTCTGTGGCCCTC3' [SEQ ID NO: 259] | 5'GTCTGATTTGTATGCCATGAAC3' [SEQ ID NO: 260] |

Figure 30 - Table 17 (continued)

ACE Human angiotensin...[gi:178285]

```
LOCUS       HUMAICEB                4020 bp    mRNA     linear   PRI 30-OCT-1994
DEFINITION  Human angiotensin I-converting enzyme mRNA, complete cds.
ACCESSION   J04144
VERSION     J04144.1  GI:178285
KEYWORDS    angiotensin converting enzyme; dipeptidyl carboxypeptidase.
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
COMMENT     Original source text: Human endothelial cell, cDNA to mRNA, clones
            lambda-HEC1922, lambda-HEC2111, and lambda-CHDT32.
            Draft entry and computer-readable sequence [1] kindly submitted by
            F.Soubrier 04-JAN-1989.
FEATURES             Location/Qualifiers
     source          1..4020
                     /organism="Homo sapiens"
                     /mol_type="mRNA"
                     /db_xref="taxon:9606"
                     /map="17q23"
     gene            1..4020
                     /gene="DCP1"
     sig_peptide     1..109
                     /gene="DCP1"
                     /note="angiotensin I-converting enzyme signal peptide"
     CDS             23..3943
                     /gene="DCP1"
                     /note="angiotensin I-converting enzyme precursor (EC
                     3.4.15.1)"
                     /codon_start=1
                     /protein_id="AAA51684.1"
                     /db_xref="GI:178286"
                     /db_xref="GDB:G00-119-840"
```

/translation="MGAASGRRGPGLLLPLPLLLLLPPQPALALDPGLQPGNFSADEA

GAQLFAQSYNSSAEQVLFQSVAASWAHDTNITAENARRQEEAALLSQEFAEAWGQKAK

ELYEPIWQNFTDPQLRRIIGAVRTLGSANLPLAKRQQYNALLSNMSRIYSTAKVCLPN

KTATCWSLDPDLTNILASSRSYAMLLFAWEGWHNAAGIPLKPLYEDFTALSNEAYKQD

GFTDTGAYWRSWYNSPTFEDDLEHLYQQLEPLYLNLHAFVRRALHRRYGDRYINLRGP

IPAHLLGDMWAQSWENIYDMVVPFPDKPNLDVTSTMLQQGWNATHMFRVAEEFFTSLE

LSPMPPEFWEGSMLEKPADGREVVCHASAWDFYNRKDFRIKQCTRVTMDQLSTVHHEM

GHIQYYLQYKDLPVSLRRGANPGFHEAIGDVLALSVSTPEHLHKIGLLDRVTNDTESD

INYLLKMALEKIAFLPFGYLVDQWRWGVFSGRTPPSRYNFDWWYLRTKYQGICPPVTR

Figure 31 - ACE mRNA

NETHFDAGAKFHVPNVTPYIRYFVSFVLQFQFHEALCKEAGYEGPLHQCDIYRSTKAG

AKLRKVLQAGSSRPWQEVLKDMVGLDALDAQPLLKYFQPVTQWLQEQNQQNGEVLGWP

EYQWHPPLPDNYPEGIDLVTDEAEASKFVEEYDRTSQVVWNEYAEANWNYNTNITTET

SKILLQKNMQIANHTLKYGTQARKFDVNQLQNTTIKRIIKKVQDLERAALPAQELEEY

NKILLDMETTYSVATVCHPNGSCLQLEPDLTNVMATSRKYEDLLWAWEGWRDKAGRAI

LQFYPKYVELINQAARLNGYVDAGDSWRSMYETPSLEQDLERLFQELQPLYLNLHAYV

RRALHRHYGAQHINLEGPIPAHLLGNMWAQTWSNIYDLVVPFPSAPSMDTTEAMLKQG

WTPRRMFKEADDFFTSLGLLPVPPEFWNKSMLEKPTDGREVVCHASAWDFYNGKDFRI

KQCTTVNLEDLVVAHHEMGHIQYFMQYKDLPVALREGANPGFHEAIGDVLALSVSTPK

HLHSLNLLSSEGGSDEHDINFLMKMALDKIAFIPFSYLVDQWRWRVFDGSITKENYNQ

EWWSLRLKYQGLCPPVPRTQGDFDPGAKFHIPSSVPYIRYFVSFIIQFQFHEALCQAA

GHTGPLHKCDIYQSKEAGQRLATAMKLGFSRPWPEAMQLITGQPNMSASAMLSYFKPL

LDWLRTENELHGEKLGWPQYNWTPNSARSEGPLPDSGRVSFLGLDLDAQQARVGQWLL
                LFLGIALLVATLGLSQRLFSIRHRSLHRHSHGPQFGSEVELRHS"
    mat peptide      110..3940
                        /gene="DCP1"
                        /product="angiotensin I-converting enzyme"
ORIGIN
```
        1 gccgagcacc gcgcaccgcg tcatgggcgc cgcctcgggc cgcggggggc cggggctgct
       61 gctgccgctg ccgctgctgt tgctgctgcc gccgcagccc gccctggcgt tggaccccgg
      121 gctgcagccc ggcaactttt ctgctgacga ggccggggcg cagctcttcg cgcagagcta
      181 caactccagc gccgaacagg tgctgttcca gagcgtggcc gccagctggg cgcacgacac
      241 caacatcacc gcggagaatg caaggcgcca ggaggaagca gccctgctca gccaggagtt
      301 tgcggaggcc tggggccaga aggccaagga gctgtatgaa ccgatctggc agaacttcac
      361 ggaccccgcag ctgcgcagga tcatcggagc tgtgcgaacc ctgggctctg ccaacctgcc
      421 cctggctaag cggcagcagt acaacgccct gctaagcaac atgagcagga tctactccac
      481 cgccaaggtc tgcctcccca acaagactgc cacctgctgg tccctggacc agatctcac
      541 caacatcctg gcttcctcgc gaagctacgc catgctcctg tttgcctggg agggctggca
      601 caacgctgcg gcatcccgc tgaaaccgct gtacgaggat tcactgccc tcagcaatga
      661 agcctacaag caggacggct tcacagacac ggggcctac tggcgctcct ggtacaactc
      721 ccccaccttc gaggacgatc tggaacacct taccccacag ctagaccccc tctacctgaa
      781 cctccatgcc ttcgtccgcc gcgcactgca tcgccagtca ggagacagat acatcaacct
      841 cagggggaccc atccctgctc atctgctggg agacatgtgg gcccagagct gggaaaacat
      901 ctacgacatg gtggtgcctt cccagacaa gcccaacctc gatgtcacca gtactatgct
      961 gcagcagggc tggaacgcca cgcacatgtt ccgggtggca gaggagttct tcacctccct
     1021 ggagctctcc ccatgcctc ccgagttctg gaagggtcg atgctggaga agccggccga
     1081 cgggcgggaa gtggtgtgcc acgcctcgg ttgggacttc tacaacagga aagacttcag
     1141 gatcaagcag tgcacgggg tcacgatgga ccagctctcc acagtgcacc atgagatggg
     1201 ccatatacag tactacctgc agtacaagga tctgcccgtc tccctgcgtc ggggggccaa
     1261 ccccggcttc catgaggcca ttggggacgt gctggcgctc tcggtctcca ctcctgaaca
```

Figure 31 - ACE mRNA (continued)

```
1321 tctgcacaaa atcggcctgc tggaccgtgt caccaatgac acggaaagtg acatcaatta
1381 cttgctaaaa atggcactgg aaaaaattgc cttcctgccc tttggctact tggtggacca
1441 gtggcgctgg ggggtcttta gtgggcgtac cccccttcc cgctacaact tcgactggtg
1501 gtatcttcga accaagtatc aggggatctg tcctcctgtt acccgaaacg aaacccactt
1561 tgatgctgga gctaagtttc atgttccaaa tgtgacacca tacatcaggt actttgtgag
1621 ttttgtcctg cagttccagt tccatgaagc cctgtgcaag gaggcaggct atgagggccc
1681 actgcaccag tgtgacatct accggtccac caaggcaggg gccaagctcc ggaaggtgct
1741 gcaggctggc tcctccaggc cctggcagga ggtgctgaag gacatggtcg gcttagatgc
1801 cctggatgcc cagccgctgc tcaagtactt ccagccagtc acccagtggc tgcaggagca
1861 gaaccagcag aacggcgagg tcctgggctg cccgagtac cagtggcacc cgccgttgcc
1921 tgacaactac ccggagggca tagacctggt gactgatgag gctgaggcca gcaagtttgt
1981 ggaggaatat gaccggacat cccaggtggt gtggaacgag tatgccgagg ccaactggaa
2041 ctacaacacc aacatcacca cagagaccag caagattctg ctgcagaaga acatgcaaat
2101 agccaaccac accctgaagt acggcaccca ggccaggaag tttgatgtga accagttgca
2161 gaacaccact atcaagcgga tcataaagaa ggttcaggac ctagaacggg cagcgctgcc
2221 tgcccaggag ctggaggagt acaacaagat cctgttggat atggaaacca cctacagcgt
2281 ggccactgtg tgccacccga atggcagctg cctgcagctc gagccagatc tgacgaatgt
2341 gatggccaca tcccggaaat atgaagacct gttatgggca tgggagggct ggcgagacaa
2401 ggcggggaga gccatcctcc agtttaccc gaaatacgtg gaactcatca accaggctgc
2461 ccggctcaat ggctatgtag atgcagggga ctcgtggagg tctatgtacg agacaccatc
2521 cctggagcaa gacctggagc ggctcttcca ggagctgcag ccactctacc tcaacctgca
2581 tgcctacgtg cgccgggccc tgcaccgtca ctacggggcc agcacatca acctggaggc
2641 gcccattcct gctcacctgc tggggaacat gtgggcgcag acctggtcca acatctatga
2701 cttggtggtg ccttccctt cagccccctc gatggacacc acagaggcta tgctaaagca
2761 gggctggacg cccaggagga tgtttaagga ggctgatgat ttcttcacct ccctgggct
2821 gctgcccgtg cctcctgagt tctggaacaa gtcgatgctg gagaagccaa ccgacgggcg
2881 ggaggtggtc tgccacgcct cggcctggga cttctacaac ggcaaggact tccggatcaa
2941 gcagtgcacc accgtgaact tggaggacct ggtggtggcc caccacgaaa tgggccacat
3001 ccagtatttc atgcagtaca aagacttacc tgtggccttg agggagggtg ccaaccccgg
3061 cttccatgag gccattgggg acgtgctagc cctctcagtg tctacgccca agcacctgca
3121 cagtctcaac ctgctgagca gtgagggtgg cagcgacgag catgacatca actttctgat
3181 gaagatggcc cttgacaaga tcgcctttat ccccttcagc tacctcgtcg atcagtggcg
3241 ctggagggta tttgatggaa gcatcaccaa ggagaactat aaccaggagt ggtggagcct
3301 caggctgaag taccagggcc tctgccccc agtgccagg actcaaggtg actttgaccc
3361 agggccaag tccacattc cttctagcgt gccttacatc aggtactttg tcagcttcat
3421 catccagttc cagttccacg aggcactgtg ccaggcagct ggccacacgg ccccctgca
3481 caagtgtgac atctaccagt ccaaggaggc cgggcagcgc ctgcgaccg ccatgaagct
3541 gggcttcagt aggccgtggc cggaagccat gcagctgatc acgggccagc caacatgag
3601 cgcctcggcc atgttgagct acttcaagcc gctgctggac tggctccgca ggagaacga
3661 gctgcatggg gagaagctgg gctggccgca gtacaactgg acgccgaact ccgctcgctc
3721 agaagggccc ctcccagaca gcggccgcgt cagcttcctg gcctggacc tggatgcgca
3781 gcaggccgc gtgggccagt ggctgctgct cttcctgggc atcgccctgc tggtagccac
3841 cctggccctc agccagcggc tcttcagcat ccgccaccgc agcctccacc ggcactccca
3901 cgggcccag ttcggctccg aggtggagct gagacactcc tgaggtgacc cggctgggtc
3961 ggccctgccc aagggcctcc caccagagac tgggatggga acactggtgg gcagctgagg
```

Figure 31 - ACE mRNA (continued)

SOD2

```
LOCUS           NM_000636               1593 bp    mRNA    linear   PRI 06-APR-2008
DEFINITION      Homo sapiens superoxide dismutase 2, mitochondrial (SOD2), nuclear
                gene encoding mitochondrial protein, transcript variant 1, mRNA.
ACCESSION       NM_000636
VERSION         NM_000636.2  GI:67782304
KEYWORDS        .
SOURCE          Homo sapiens (human)
  ORGANISM      Homo sapiens
                Eukaryota; Metazoa; Chordata; Craniata; Vertebrata; Euteleostomi;
                Mammalia; Eutheria; Euarchontoglires; Primates; Haplorrhini;
                Catarrhini; Hominidae; Homo.
REFERENCE       1  (bases 1 to 1593)
  AUTHORS       Singh,M., Khan,A.J., Shah,P.P., Shukla,R., Khanna,V.K. and
                Parmar,D.
  TITLE         Polymorphism in environment responsive genes and association with
                Parkinson disease
  JOURNAL       (er) Mol. Cell. Biochem. (2008) In press
   PUBMED       18327668
  REMARK        GeneRIF: Observational study of gene-disease association and
                gene-gene interaction. (HuGE Navigator)
REFERENCE       2  (bases 1 to 1593)
COMMENT         REVIEWED REFSEQ: This record has been curated by NCBI staff. The
                reference sequence was derived from BG699596.1, Y00985.1, Y00472.1
                and AL691784.1.
                On Jun 15, 2005 this sequence version replaced gi:10835186.

Summary: This gene is a member of the iron/manganese superoxide
                dismutase family. It encodes a mitochondrial protein that forms a
                homotetramer and binds one manganese ion per subunit. This protein
                binds to the superoxide byproducts of oxidative phosphorylation and
                converts them to hydrogen peroxide and diatomic oxygen. Mutations
                in this gene have been associated with idiopathic cardiomyopathy
                (IDC), premature aging, sporadic motor neuron disease, and cancer.
                Alternate transcriptional splice variants, encoding different
                isoforms, have been characterized.

Transcript Variant: This variant (1) represents the longest
                transcript and encodes the longer isoform (A). Variants 1 and 2
                encode the same isoform (A).

Publication Note:  This RefSeq record includes a subset of the
                publications that are available for this gene. Please see the
                Entrez Gene record to access additional publications.
                COMPLETENESS: complete on the 3' end.
PRIMARY         REFSEQ_SPAN         PRIMARY_IDENTIFIER PRIMARY_SPAN        COMP
                1-201               BG699596.1         8-208
                202-398             Y00985.1           142-338
                399-400             Y00472.1           311-312
                401-1036            Y00985.1           341-976
                1037-1593           AL691784.1         46-602
FEATURES             Location/Qualifiers
     source          1..1593
                     /organism="Homo sapiens"
```

Figure 32 - SOD2 mRNA

```
                    /mol_type="mRNA"
                    /db_xref="taxon:9606"
                    /chromosome="6"
                    /map="6q25.3"
    gene            1..1593
                    /gene="SOD2"
                    /synonym="IPO-B, MNSOD, Mn-SOD"
                    /note="superoxide dismutase 2, mitochondrial"
                    /db_xref="GeneID:6648"
                    /db_xref="HGNC:11180"
                    /db_xref="HPRD:00938"
                    /db_xref="MIM:147460"
    exon            1..177
                    /gene="SOD2"
                    /inference="alignment:Splign"
                    /number=1
    CDS             155..823
                    /gene="SOD2"
                    /EC_number="1.15.1.1"
                    /note="isoform A precursor is encoded by transcript
                    variant 1; mangano-superoxide dismutase; Mn superoxide
                    dismutase; indophenoloxidase B; manganese-containing
                    superoxide dismutase; manganese superoxide dismutase"
                    /codon_start=1
                    /product="manganese superoxide dismutase isoform A
                    precursor"
                    /protein_id="NP_000627.2"
                    /db_xref="GI:67782305"
                    /db_xref="CCDS:CCDS5265.1"
                    /db_xref="GeneID:6648"
                    /db_xref="HGNC:11180"
                    /db_xref="HPRD:00938"
                    /db_xref="MIM:147460"
                    /translation="MLSRAVCGTSRQLAPVLGYLGSRQKHSLPDLPYDYGALEPHINA
                    QIMQLHHSKHHAAYVNNLNVTEEKYQEALAKGDVTAQIALQPALKFNGGGHINHSIFW
                    TNLSPNGGGEPKGELLEAIKRDFGSFDKFKEKLTAASVGVQGSGWGWLGFNKERGHLQ
                    IAACPNQDPLQGTTGLIPLLGIDVWEHAYYLQYKNVRPDYLKAIWNVINWENVTERYM
                    ACKK"
    sig_peptide     155..226
                    /gene="SOD2"
    mat_peptide     227..820
                    /gene="SOD2"
                    /product="manganese superoxide dismutase isoform A"
    exon            178..380
                    /gene="SOD2"
                    /inference="alignment:Splign"
                    /number=2
    exon            381..497
                    /gene="SOD2"
                    /inference="alignment:Splign"
                    /number=3
    exon            498..677
                    /gene="SOD2"
                    /inference="alignment:Splign"
                    /number=4
```

Figure 32 - SOD2 mRNA (continued)

```
     exon            678..1593
                     /gene="SOD2"
                     /inference="alignment:Splign"
                     /number=5b
     STS             713..1338
                     /gene="SOD2"
                     /standard_name="SOD2_3060"
                     /db_xref="UniSTS:462564"
     STS             760..936
                     /gene="SOD2"
                     /standard_name="D6S1335"
                     /db_xref="UniSTS:13774"
     STS             824..1148
                     /gene="SOD2"
                     /standard_name="D6S1419"
                     /db_xref="UniSTS:8761"
     polyA_site      845
                     /gene="SOD2"
                     /experiment="experimental evidence, no additional details
                     recorded"
     polyA_site      1038
                     /gene="SOD2"
                     /experiment="experimental evidence, no additional details
                     recorded"
                     /note="polyA site"
ORIGIN
        1 gcggtgccct tgcggcgcag ctggggtcgc ggccctgctc ccgcgctttc cttaaggccc
       61 gcgggcggcg caggagcggc actcgtggct gtggtggctt cggcagcggc ttcagcagat
      121 cggcggcatc agcggtagca ccagcactag cagcatgttg agccgggcag tgtgcggcac
      181 cagcaggcag ctggctccgg ttttggggta tctgggctcc aggcagaagc acagcctccc
      241 cgacctgccc tacgactacg gcgccctgga acctcacatc aacgcgcaga tcatgcagct
      301 gcaccacagc aagcaccacg cggcctacgt gaacaacctg aacgtcaccg aggagaagta
      361 ccaggaggcg ttggccaagg gagatgttac agcccagata gctcttcagc ctgcactgaa
      421 gttcaatggt ggtggtcata tcaatcatag cattttctgg acaaacctca gccctaacgg
      481 tggtggagaa cccaaagggg agttgctgga agccatcaaa cgtgactttg gttcctttga
      541 caagttaag gagaagctga cggctgcatc tgttggtgtc caaggctcag gttggggttg
      601 gcttggtttc aataaggaac ggggacactt acaaattgct gcttgtccaa atcaggatcc
      661 actgcaagga acaacaggcc ttattccact gctggggatt gatgtgtggg agcacgctta
      721 ctaccttcag tataaaaatg tcaggcctga ttatctaaaa gctatttgga atgtaatcaa
      781 ctgggagaat gtaactgaaa gatacatggc ttgcaaaaag taaaccacga tcgttatgct
      841 gagtatgtta agctctttat gactgttttt gtagtggtat agagtactgc agaatacagt
      901 aagctgctct attgtagcat ttcttgatgt tgcttagtca cttatttcat aaacaactta
      961 atgttctgaa taatttctta ctaaacattt tgttattggg caagtgattg aaaatagtaa
     1021 atgctttgtg tgattgaatc tgattggaca ttttcttcag agagctaaat tacaattgtc
     1081 atttataaaa ccatcaaaaa tattccatcc atatactttg gggacttgta gggatgcctt
     1141 tctagtccta ttctattgca gttatagaaa atctagtctt tgccccagt tacttaaaaa
     1201 taaatatta acactttccc aagggaaaca ctcggctttc tatagaaaat tgcactttt
     1261 gtcgagtaat cctctgcagt gatacttctg gtagatgtca cccagtggtt tttgttaggt
     1321 caaatgttcc tgtatagttt ttgcaaatag agctgtatac tgtttaaatg tagcaggtga
     1381 actgaactgg ggtttgctca cctgcacagt aaaggcaaac ttcaacagca aaactgcaaa
     1441 aaggtggttt ttgcagtagg agaaaggagg atgtttatt gcagggcgcc aagcaaggag
     1501 aattgggcag ctcatgcttg agcccaatc tccatgatga cctacaagct agagtattta
     1561 aaggcagtgg taaatttcag gaaagcagaa gtt
```

Figure 32 - SOD2 mRNA (continued)

SLC6A3

```
LOCUS       NM_001044               3925 bp    mRNA    linear   PRI 20-APR-2008
DEFINITION  Homo sapiens solute carrier family 6 (neurotransmitter
            transporter, dopamine), member 3 (SLC6A3), mRNA.
CCESSION    NM_001044
VERSION     NM_001044.3  GI:133908627
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
COMMENT     VALIDATED REFSEQ: This record has undergone validation or
            preliminary review. The reference sequence was derived from
            M95167.1 and AC026748.7.
            On Mar 21, 2007 this sequence version replaced gi:38194225.

Summary: The dopamine transporter (DAT1) mediates the active
            reuptake of dopamine from the synapse and is a principal regulator
            of dopaminergic neurotransmission. The DAT1 gene has been
            implicated in human disorders such as parkinsonism, Tourette
            syndrome, and substance abuse (Vandenbergh et al., 1992 [PubMed
            1359373]).[supplied by OMIM].

Publication Note:  This RefSeq record includes a subset of the
            publications that are available for this gene. Please see the
            Entrez Gene record to access additional publications.
            COMPLETENESS: complete on the 3' end.
PRIMARY     REFSEQ_SPAN         PRIMARY_IDENTIFIER PRIMARY_SPAN        COMP
            1-2712              M95167.1           8-2719
            2713-3925           AC026748.7         115767-116979
FEATURES             Location/Qualifiers
     source          1..3925
                     /organism="Homo sapiens"
                     /mol_type="mRNA"
                     /db_xref="taxon:9606"
                     /chromosome="5"
                     /map="5p15.3"
     gene            1..3925
                     /gene="SLC6A3"
                     /synonym="DAT, DAT1"
                     /note="solute carrier family 6 (neurotransmitter
                     transporter, dopamine), member 3"
                     /db_xref="GeneID:6531"
                     /db_xref="HGNC:11049"
                     /db_xref="HPRD:00543"
                     /db_xref="MIM:126455"
     exon            1..76
                     /gene="SLC6A3"
                     /inference="alignment:Splign"
                     /number=1
     exon            77..407
                     /gene="SLC6A3"
                     /inference="alignment:Splign"
```

Figure 33 - SLC6A3 mRNA

```
             CDS             /number=2
                             122..1984
                             /gene="SLC6A3"
                             /note="dopamine transporter; variable number tandem
repeat
                             (VNTR)"
                             /codon_start=1
                             /product="solute carrier family 6 (neurotransmitter
                             transporter, dopamine), member 3"
                             /protein_id="NP_001035.1"
                             /db_xref="GI:4507041"
                             /db_xref="CCDS:CCDS3863.1"
                             /db_xref="GeneID:6531"
                             /db_xref="HGNC:11049"
                             /db_xref="HPRD:00543"
                             /db_xref="MIM:126455"

/translation="MSKSKCSVGLMSSVVAPAKEPNAVGPKEVELILVKEQNGVQLTS

STLTNPRQSPVEAQDRETWGKKIDFLLSVIGFAVDLANVWRFPYLCYKNGGGAFLVPY

LLFMVIAGMPLFYMELALGQFNREGAAGVWKICPILKGVGFTVILISLYVGFFYNVII

AWALHYLFSSFTTELPWIHCNNSWNSPNCSDAHPGDSSGDSSGLNDTFGTTPAAEYFE

RGVLHLHQSHGIDDLGPPRWQLTACLVLVIVLLYFSLWKGVKTSGKVVWITATMPYVV

LTALLLRGVTLPGAIDGIRAYLSVDFYRLCEASVWIDAATQVCFSLGVGFGVLIAFSS

YNKFTNNCYRDAIVTTSINSLTSFSSGFVVFSFLGYMAQKHSVPIGDVAKDGPGLIFI

IYPEAIATLPLSSAWAVVFFIMLLTLGIDSAMGGMESVITGLIDEFQLLHRHRELFTL

FIVLATFLLSLFCVTNGGIYVFTLLDHFAAGTSILFGVLIEAIGVAWFYGVGQFSDDI

QQMTGQRPSLYWRLCWKLVSPCFLLFVVVVSIVTFRPPHYGAYIFPDWANALGWVIAT
                             SSMAMVPIYAAYKFCSLPGSFREKLAYAIAPEKDRELVDRGEVRQFTLRHWLKV"
             exon            408..539
                             /gene="SLC6A3"
                             /inference="alignment:Splign"
                             /number=3
             exon            540..774
                             /gene="SLC6A3"
                             /inference="alignment:Splign"
                             /number=4
             exon            775..913
                             /gene="SLC6A3"
                             /inference="alignment:Splign"
                             /number=5
             exon            914..1048
                             /gene="SLC6A3"
                             /inference="alignment:Splign"
                             /number=6
             exon            1049..1152
                             /gene="SLC6A3"
                             /inference="alignment:Splign"
```

Figure 33 - SLC6A3 mRNA (continued)

```
                        /number=7
        exon            1153..1277
                        /gene="SLC6A3"
                        /inference="alignment:Splign"
                        /number=8
        exon            1278..1390
                        /gene="SLC6A3"
                        /inference="alignment:Splign"
                        /number=9
        exon            1391..1519
                        /gene="SLC6A3"
                        /inference="alignment:Splign"
                        /number=10
        exon            1520..1619
                        /gene="SLC6A3"
                        /inference="alignment:Splign"
                        /number=11
        exon            1620..1720
                        /gene="SLC6A3"
                        /inference="alignment:Splign"
                        /number=12
        exon            1721..1888
                        /gene="SLC6A3"
                        /inference="alignment:Splign"
                        /number=13
        exon            1889..1960
                        /gene="SLC6A3"
                        /inference="alignment:Splign"
                        /number=14
        exon            1961..3925
                        /gene="SLC6A3"
                        /inference="alignment:Splign"
                        /number=15
        STS             2711..3193
                        /gene="SLC6A3"
                        /standard_name="GDB:194281"
                        /db_xref="UniSTS:155786"
        STS             2711..3160
                        /gene="SLC6A3"
                        /standard_name="GDB:392133"
                        /db_xref="UniSTS:157184"
ORIGIN
        1 cggagcggga ggggaggctt cgcggaacgc tctcggcgcc aggactcgcg tgcaaagccc
       61 aggcccgggc ggccagacca agagggaaga agcacagaat tcctcaactc ccagtgtgcc
      121 catgagtaag agcaaatgct ccgtgggact catgtcttcc gtggtggccc ggctaagga
      181 gcccaatgcc gtgggcccga aggaggtgga gctcatcctt gtcaaggagc agaacggagt
      241 gcagctcacc agctccaccc tcaccaaccc gcggcagagc ccgtggagg cccaggatcg
      301 ggagacctgg ggcaagaaga tcgacttct cctgtccgtc attggctttg ctgtggacct
      361 ggccaacgtc tggcggttcc cctacctgtg ctacaaaaat ggtggcggtg ccttcctggt
      421 cccctacctg ctcttcatgg tcattgctgg gatgccactt ttctacatgg agctggccct
      481 cggccagttc aacaggcaag gggccgctgg tgtctggaag atctgcccca tactgaaagg
      541 tgtgggcttc acggtcatcc tcatctcact gtatgtcggc ttcttctaca acgtcatcat
      601 cgcctgggcg ctgcactatc tcttctcctc cttcaccacg gagctcccct ggatccactg
      661 caacaactcc tggaacagcc ccaactgctc ggatgcccat cctggtgact ccagtggaga
      721 cagctcgggc ctcaacgaca cttttgggac cacacctgct gccgagtact tgaacgtgg
      781 cgtgctgcac ctccaccaga gccatggcat cgacgacctg gggcctccgc ggtggcagct
```

Figure 33 - SLC6A3 mRNA (continued)

```
 841 cacagcctgc ctggtgctgg tcatcgtgct gctctacttc agcctctgga agggcgtgaa
 901 gacctcaggg aaggtggtat ggatcacagc caccatgcca tacgtggtcc tcactgccct
 961 gctcctgcgt ggggtcaccc tccctggagc catagacggc atcagagcat acctgagcgt
1021 tgacttctac cggctctgcg aggcgtctgt ttggattgac gcggccaccc aggtgtgctt
1081 ctccctgggc gtggggttcg gggtgctgat cgccttctcc agctacaaca agttcaccaa
1141 caactgctac agggacgcga ttgtcaccac ctccatcaac tccctgacga gcttctcctc
1201 cggcttcgtc gtcttctcct tcctggggta catggcacag aagcacagtg tgcccatcgg
1261 ggacgtggcc aaggacgggc agggctgat cttcatcatc tacccggaag ccatcgccac
1321 gctccctctg tcctcagcct gggccgtggt cttcttcatc atgctgctca ccctgggtat
1381 cgacagcgcc atgggtggta tggagtcagt gatcaccggg ctcatcgatg agttccagct
1441 gctgcacaga caccgtgagc tcttcacgct cttcatcgtc ctggcgacct tcctcctgtc
1501 cctgttctgc gtcaccaacg tggcatcta cgtcttcacg ctcctggacc attttgcagc
1561 cggcacgtcc atcctctttg gagtgctcat cgaagccatc ggagtggcct ggttctatgg
1621 tgttgggcag ttcagcgacg acatccagca gatgaccggg cagcggccca gcctgtactg
1681 gcggctgtgc tggaagctgg tcagcccctg ctttctcctg ttcgtggtcg tggtcagcat
1741 tgtgaccttc agacccccc actacggagc ctacatcttc cccgactggg ccaacgcgct
1801 gggctgggtc atcgccacat cctccatggc catggtgccc atctatgcgg cctacaagtt
1861 ctgcagcctg cctgggtcct tcgagagaa actggcctac gccattgcac ccgagaagga
1921 ccgtgagctg gtggacagag gggaggtgcg ccagttcacg ctccgccact ggctcaaggt
1981 gtagagggag cagagacgaa gaccccagga agtcatcctg caatgggaga gacacgaaca
2041 aaccaaggaa atctaagttt cgagagaaag gagggcaact tctactcttc aacctctact
2101 gaaaacacaa acaacaaagc agaagactcc tctcttctga ctgtttacac ctttccgtgc
2161 cgggagcgca cctcgccgtg tcttgtgttg ctgtaataac gacgtagatc tgtgcagcga
2221 ggtccacccc gttgttgtcc ctgcagggca gaaaaacgtc taacttcatg ctgtctgtgt
2281 gaggctccct ccctccctgc tcctgctcc cggctctgag gctgcccag gggcactgtg
2341 ttctcaggcg gggatcacga tccttgtaga cgcacctgct gagaatcccc gtgctcacag
2401 tagcttccta gaccatttac tttgcccata ttaaaaagcc aagtgtcctg ctggttttag
2461 ctgtgcagaa ggtgaaatgg aggaaaccac aaattcatgc aaagtccttt cccgatgcgt
2521 ggctcccagc agaggccgta aattgagcgt tcagttgaca cattgcacac acagtctgtt
2581 cagaggcatt ggaggatggg ggtcctggta tgtctcacca ggaaattctg tttatgttct
2641 tgcagcagag agaaataaaa ctccttgaaa ccagctcagg ctactgccac tcaggcagcc
2701 tgtgggtcct tgcggtgtag gaacggcct gagaggagcg tgtcctatcc ccggacgcat
2761 gcagggcccc cacaggagcg tgtcctatcc ccggacgcat gcagggcccc cacaggagca
2821 tgtcctatcc ctggacgcat gcagggcccc cacaggagcg tgtactaccc agaacgcat
2881 gcagggcccc cacaggagcg tgtactaccc caggacgcat gcagggcccc cactggagcg
2941 tgtactaccc caggacgcat gcagggcccc cacaggagcg tgtcctatcc ccggaccgga
3001 cgcatgcagg gcccccacag gagcgtgtac tacccagga cgcatgcagg gcccccacag
3061 gagcgtgtac tacccagga tgcatgcagg gcccccacag gagcgtgtac tacccagga
3121 cgcatgcagg gcccccatgc aggcagcctg cagaccacac tctgcctggc cttgagccgt
3181 gacctccagg aagggacccc actggaattt tattctctc aggtgcgtgc cacatcaata
3241 acaacagttt ttatgtttgc gaatggcttt ttaaaatcat atttacctgt gaatcaaaac
3301 aaattcaaga atgcagtatc cgcgagcctg cttgctgata ttgcagtttt tgtttacaag
3361 aataattagc aatactgagt gaaggatgtt ggccaaaagc tgctttccat ggcacactgc
3421 cctctgccac tgacaggaaa gtggatgcca tagtttgaat tcatgcctca agtcggtggg
3481 cctgcctacg tgctgcccga gggcaggggc cgtgcagggc cagtcatggc tgtcccctgc
3541 aagtggacgt gggctccagg gactggagtg taatgctcgg tgggagccgt cagcctgtga
3601 actgccaggc agctgcagtt agcacagagg atggcttccc cattgccttc tggggaggga
3661 cacagaggac ggcttcccca tcgccttctg gccgctgcag tcagcacaga gagcggcttc
3721 cccattgcct tctggggagg gacacagagg acagcttccc catcgccttc tggctgctgc
3781 agtcagcaca gagagcggct tcccatcgc ctttctggga ggggctccgt gtagcaaccc
3841 aggtgttgtc cgtgtctgtt gaccaatctc tattcagcat cgtgtgggtc cctaagcaca
3901 ataaaagaca tccacaatgg aaaaa
```

Figure 33 - SLC6A3 mRNA (continued)

CYP2C9

```
LOCUS       NM_000771               1835 bp    mRNA    linear   PRI 20-APR-2008
DEFINITION  Homo sapiens cytochrome P450, family 2, subfamily C, polypeptide 9
            (CYP2C9), mRNA.
ACCESSION   NM_000771
VERSION     NM_000771.2  GI:13699817
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Haplorrhini;
            Catarrhini; Hominidae; Homo.
REFERENCE   1  (bases 1 to 1835)
COMMENT     REVIEWED REFSEQ: This record has been curated by NCBI staff. The
            reference sequence was derived from D00173.1 and M61857.1.
            On Apr 20, 2001 this sequence version replaced gi:10140850.

Summary: This gene encodes a member of the cytochrome P450
            superfamily of enzymes. The cytochrome P450 proteins are
            monooxygenases which catalyze many reactions involved in drug
            metabolism and synthesis of cholesterol, steroids and other lipids.
            This protein localizes to the endoplasmic reticulum and its
            expression is induced by rifampin. The enzyme is known to
            metabolize many xenobiotics, including phenytoin, tolbutamide,
            ibuprofen and S-warfarin. Studies identifying individuals who are
            poor metabolizers of phenytoin and tolbutamide suggest that this
            gene is polymorphic. The gene is located within a cluster of
            cytochrome P450 genes on chromosome 10q24.

Publication Note:  This RefSeq record includes a subset of the
            publications that are available for this gene. Please see the
            Entrez Gene record to access additional publications.
            COMPLETENESS: complete on the 3' end.
FEATURES             Location/Qualifiers
     source          1..1835
                     /organism="Homo sapiens"
                     /mol_type="mRNA"
                     /db_xref="taxon:9606"
                     /chromosome="10"
                     /map="10q24"
     gene            1..1835
                     /gene="CYP2C9"
                     /synonym="CPC9, CYP2C, CYP2C10, MGC88320, P450IIC9,
                     MGC149605, P450 MP-4, P450 PB-1"
                     /note="cytochrome P450, family 2, subfamily C, polypeptide
                     9"
                     /db_xref="GeneID:1559"
                     /db_xref="HGNC:2623"
                     /db_xref="HPRD:03084"
                     /db_xref="MIM:601130"
     CDS             1..1473
                     /gene="CYP2C9"
                     /EC_number="1.14.14.1"
                     /note="mephenytoin 4-hydroxylase; microsomal
                     monooxygenase; xenobiotic monooxygenase;
                     flavoprotein-linked monooxygenase; cytochrome P450,
                     subfamily IIC (mephenytoin 4-hydroxylase), polypeptide 10;
```

Figure 34 - CYP2C9 mRNA

```
                    cytochrome P450, subfamily IIC (mephenytoin
                    4-hydroxylase), polypeptide 9; cytochrome P-450
                    S-mephenytoin 4-hydroxylase; cytochrome p4502C9"
                    /codon_start=1
                    /product="cytochrome P450, family 2, subfamily C,
                    polypeptide 9"
                    /protein_id="NP_000762.2"
                    /db_xref="GI:13699818"
                    /db_xref="CCDS:CCDS7437.1"
                    /db_xref="GeneID:1559"
                    /db_xref="HGNC:2623"
                    /db_xref="HPRD:03084"
                    /db_xref="MIM:601130"
```

/translation="MDSLVVLVLCLSCLLLLSLWRQSSGRGKLPPGPTPLPVIGNILQ

IGIKDISKSLTNLSKVYGPVFTLYFGLKPIVVLHGYEAVKEALIDLGEEFSGRGIFPL

AERANRGFGIVFSNGKKWKEIRRFSLMTLRNFGMGKRSIEDRVQEEARCLVEELRKTK

ASPCDPTFILGCAPCNVICSIIFHKRFDYKDQQFLNLMEKLNENIKILSSPWIQICNN

FSPIIDYFPGTHNKLLKNVAFMKSYILEKVKEHQESMDMNNPQDFIDCFLMKMEKEKH

NQPSEFTIESLENTAVDLFGAGTETTSTTLRYALLLLLKHPEVTAKVQEEIERVIGRN

RSPCMQDRSHMPYTDAVVHEVQRYIDLLPTSLPHAVTCDIKFRNYLIPKGTTILISLT

SVLHDNKEFPNPEMFDPHHFLDEGGNFKKSKYFMPFSAGKRICVGEALAGMELFLFLT

```
                    SILQNFNLKSLVDPKNLDTTPVVNGFASVPPFYQLCFIPV"
    misc_feature    1303..1305
                    /gene="CYP2C9"
                    /note="heme binding site"
    exon            1..168
                    /gene="CYP2C9"
                    /inference="alignment:Splign"
                    /number=1
    STS             30..166
                    /gene="CYP2C9"
                    /standard_name="GDB:193845"
                    /db_xref="UniSTS:155761"
    exon            169..331
                    /gene="CYP2C9"
                    /inference="alignment:Splign"
                    /number=2
    exon            332..481
                    /gene="CYP2C9"
                    /inference="alignment:Splign"
                    /number=3
    exon            482..642
                    /gene="CYP2C9"
                    /inference="alignment:Splign"
                    /number=4
    exon            643..819
                    /gene="CYP2C9"
                    /inference="alignment:Splign"
                    /number=5
    exon            820..961
                    /gene="CYP2C9"
                    /inference="alignment:Splign"
```

Figure 34 - CYP2C9 mRNA (continued)

```
     exon            /number=6
                     962..1149
                     /gene="CYP2C9"
                     /inference="alignment:Splign"
                     /number=7
     exon            1150..1291
                     /gene="CYP2C9"
                     /inference="alignment:Splign"
                     /number=8
     exon            1292..1835
                     /gene="CYP2C9"
                     /inference="alignment:Splign"
                     /number=9
     STS             1528..1812
                     /gene="CYP2C9"
                     /standard_name="SGC35305"
                     /db_xref="UniSTS:73844"
     STS             1620..1808
                     /gene="CYP2C9"
                     /standard_name="RH45236"
                     /db_xref="UniSTS:2795"
     polyA_signal    1812..1817
                     /gene="CYP2C9"
     polyA_site      1835
                     /gene="CYP2C9"
                     /experiment="experimental evidence, no additional details
                     recorded"
ORIGIN
        1 atggattctc ttgtggtcct tgtgctctgt ctctcatgtt tgcttctcct ttcactctgg
       61 agacagagct ctgggagagg aaaactccct cctggcccca ctcctctccc agtgattgga
      121 aatatcctac agataggtat taaggacatc agcaaatcct taaccaatct ctcaaaggtc
      181 tatggcccgg tgttcactct gtattttggc ctgaaaccca tagtggtgct gcatggatat
      241 gaagcagtga aggaagccct gattgatctt ggagaggagt tttctggaag aggcattttc
      301 ccactggctg aaagagctaa cagaggattt ggaattgttt tcagcaatgg aaagaaatgg
      361 aaggagatcc ggcgtttctc cctcatgacg ctgcggaatt tgggatggg gaagaggagc
      421 attgaggacc gtgttcaaga ggaagcccgc tgccttgtgg aggagttgag aaaaaccaag
      481 gcctcaccct gtgatcccac tttcatcctg gctgtgctc cctgcaatgt gatctgctcc
      541 attattttcc ataaacgttt tgattataaa gatcagcaat tcttaacttt aatggaaaag
      601 ttgaatgaaa acatcaagat tttgagcagc cctggatcc agatctgcaa taatttttct
      661 cctatcattg attacttccc gggaactcac aacaaattac ttaaaaacgt tgcttttatg
      721 aaaagttata tttggaaaa agtaaagaa caccaagaat caatggacat gaacaaccct
      781 caggacttta ttgattgctt cctgatgaaa atggagaagg aaaagcacaa ccaaccatct
      841 gaatttacta ttgaaagctt ggaaaacact gcagttgact tgtttggagc tgggacagag
      901 acgacaagca caacccctga gatgctctc cttctcctgc tgaagcaccc agaggtcaca
      961 gctaaagtcc aggaagagat tgaacgtgtg attggcagaa accggagccc ctgcatgcaa
     1021 gacaggagcc acatgcccta cacagatgct gtggtgcacg aggtccagag atacattgac
     1081 cttctcccca ccagcctgcc ccatgcagtg acctgtgaca ttaaattcag aaactatctc
     1141 attcccaagg gcacaaccat attaatttcc ctgacttctg tgctacatga acaaaagaa
     1201 tttcccaacc cagagatgtt tgaccctcat cactttctgg atgaaggtgg aaatttaag
     1261 aaaagtaaat acttcatgcc tttctcagca ggaaaacgga tttgtgtggg agaagccctg
     1321 gccggcatgg agctgttttt attcctgacc tccattttac agaactttaa cctgaaatct
     1381 ctggttgacc caaagaacct tgacaccact ccagttgtca atggatttgc tctgtgccg
     1441 cccttctacc agctgtgctt cattcctgtc tgaagaagag cagatggcct ggctgctgct
     1501 gtgcagtccc tgcagctctc tttcctctgg ggcattatcc atctttgcac tatctgtaat
     1561 gccttttctc acctgtcatc tcacatttc ccttccctga agatctagta acattcgac
     1621 ctccattacg gagagtttcc tatgtttcac tgtgcaaata tatctgctat tctccatact
     1681 ctgtaacagt tgcattgact gtcacataat gctcatactt atctaatgta gagtattaat
     1741 atgttattat taaatagaga aaatatgattt gtgtattata attcaaaggc atttcttttc
     1801 tgcatgatct aaataaaaag cattattatt tgctg
```

Figure 34 - CYP2C9 mRNA   (continued)

POLYMORPHISMS IN GENES AFFECTING ACE-RELATED DISORDERS AND USES THEREOF

RELATED APPLICATIONS

This application claims the benefit of the PCT/US2008/005558 filed Apr. 30, 2008, which claims priority to U.S. Provisional Patent Application 60/926,932 filed Apr. 30, 2007, the disclosure of which is incorporated herein by reference, in its entirety.

GOVERNMENT SUPPORT

The invention was made with government support from the National Institutes of Health research grants HL 74730, HL 69758 and RR017568. The government may have certain rights in the invention.

BACKGROUND

Single nucleotide polymorphisms (SNPs) are useful as biomarkers for predicting disease susceptibility or progression, or as a guide for individualized therapy, including drug therapy.

ACE—

Angiotensin I-converting enzyme (ACE) plays a key role in cardiovascular biology. Its functions include formation of angiotensin II and inactivation of bradykinin, resulting in vasoconstriction and increased blood pressure. ACE inhibitors are recommended as first-line treatment of hypertension and heart failure. Expressed in many tissues, ACE further affects a broad spectrum of physiological processes. As a result, the ACE gene has been implicated in susceptibility to hypertension, myocardial infarction, renal pathophysiology, diabetes, and Alzheimer's disease.

In particular, angiotensin I-converting enzyme (ACE1) is expressed with a wide tissue distribution including plasma, endothelial cells, kidney, heart and lungs. This enzyme hydrolyzes a number of substrates, including conversion of angiotensin I to angiotensin II (as part of the renin-angiotensin system). Angiotensin II (AngII) is a potent vasoconstrictor and pro-hypertrophic factor. Ang II induces production of superoxide free radicals ($O_2^-$) that scavenge available nitric oxide and reduce endothelial vasodilatation. ACE1 has even greater affinity for bradykinin, thus hydrolyzing and inactivating a potent vasodilator. Through these pathways, ACE1 exerts potent physiological influence over salt balance, blood volume and blood pressure levels with significant implications for cardiovascular disease in particular.

Targeted reduction of ACE1 via the blockbuster drug class of ACE inhibitors that directly bind the active site of the ACE protein is a first line anti-hypertensive treatment for heart disease. ACE inhibitors decrease the release of aldosterone and retention of salt and water, significantly lowering blood pressure. Drugs in this class have been shown to reduce mortality in many large clinical trials. These drugs are often administered immediately following myocardial infarction. They currently represent a major pharmaceutical class with millions of prescriptions worldwide, with additional indications in hypertension or renal crisis in relation to scleroderma, and prevention of kidney damage in some diabetics. Furthermore, recent literature indicates that ACE1 may play a role in the degradation of Alzheimer's plaques making it a possible disease factor (26,39).

It has been determined that there is variability in patient responses to ACE inhibitor treatment. Family-based studies over the last two decades indicate that ACE1 levels as a quantitative phenotype are strongly influenced by a genetic component that maps to the ACE1 locus; however, well-supported functional variants remain to be identified (40, 1, 11). Nonetheless, this has been considered one of the most compelling examples in human genetics of a single gene contributing to variability in a complex human trait. Intolerance for ACE inhibitors is as high as 20%, with the most common side effect being a severe cough, especially in Asian patients (41).

Moreover, studies in African-American patients on ACE inhibitors indicated they received less benefit (16) and increased risk of side effects (4-5 fold) (18) and mortality from angioedema (42-45), suggesting a possible pharmacogenetic influence on drug response. An intron 16 ALU insertion-deletion polymorphism of 287 bp has been extensively studied, because it revealed significant associations in a number of studies. However, several research groups have shown that this polymorphism is unlikely to have any direct functional role (5,4) and, instead, is likely in linkage to one or more true, and as yet undetermined, functional variants. Studies employing diverse populations and public data from the HapMap project indicate the ALU polymorphism alone is an inadequate proxy for the genetic diversity at this gene locus. However, there are thousands of studies genotyping solely the ALU polymorphism in a variety of clinical populations. These demonstrate both positive and negative associations, as reflected in metanalyses of this variant (3). Since these previous studies rely on the assumption that the ALU polymorphism is completely or highly linked to true functional variants, they may be missing critical information if this assumption is incorrect or only partially correct. For example, one study of outcomes in 38,000 individuals receiving ACE inhibitor treatment genotyped only the ALU polymorphism and found no significant association (2).

The suggestion of a heritable component to serum ACE activity (1) led to extensive phenotype-genotype studies with ACE-related pathophysiology and response to ACE inhibitors (2). Numerous studies have focused on an insertion/deletion (I/D) polymorphism in intron 15. However, metaanalyses of phenotypic associations largely failed to confirm a role for I/D (3), and in vitro experiments did not reveal any effect on transcription (4) or splicing (5). Therefore, genetic factors contributing to differential ACE expression remain uncertain.

What are lacking are tools for predicting the likelihood that a particular patient will be responsive to a therapeutic ACE, and in particular, identifying agents to which the ACE will be sensitive or resistant. Also lacking are tools for profiling genetic factors influencing sensitivity and resistance of patients to ACE therapeutic agents. Such tools, and the resulting gene expression profiles, would be predictive of treatment response of a patient to a particular drug, and would allow for increased predictability regarding chemosensitivity or chemoresistance of such patients to enable the design of optimal treatment regimens for patients.

SOD2—

Oxidative stress and damage play a role in the pathogenesis of a number of diseases. In particular, mitochondrial-derived oxidants play an important role in the pathogenesis of many human disorders.

SOD2 is an antioxidant, the mitochondrial form of SOD and an important defense against oxidative damage. The SOD2 gene is a member of the iron/manganese superoxide dismutase family. The mitochondrial superoxide dismutase protein (SOD2) serves a critical cellular role in protecting from harmful reactive species by reducing these species to hydrogen peroxide ($H_2O_2$) which is then processed to hydroxide (OH) and then water ($H_2O$). This is a normal cellular process that is critical to life and protects the integrity of cellular genomes. Under conditions of stress including disease and environmental conditions (e.g., toxins) reactive species can accumulate to a degree that overwhelms the capacity of endogenous protectors including SOD2. Thus, if common alleles exist that affect SOD2 production these alleles may contribute to many diseases, but may only be important under conditions of accumulated oxidative stress.

What are lacking are tools for predicting the likelihood that a particular patient will be responsive to a therapeutic SOD2 agent, and in particular, identifying agents to which the SOD2 agent will be sensitive or resistant.

Also lacking are tools for profiling genetic factors influencing sensitivity and resistance of patients to SOD2-caused oxidative damage.

SLC6A3—

Dopamine active transporter (SLC6A3, formerly) is a membrane-spanning protein that binds the neurotransmitter dopamine. SLC6A3 provides the primary mechanism through which dopamine is cleared from synapses. SLC6A3 works by transporting dopamine from the synapse into a neuron. SLC6A3 is present in the peri-synaptic area of dopaminergic neurons in areas of the brain where dopamine signaling is common. SLC6A3 terminates the dopamine signal and is implicated in a number of dopamine-related disorders, including alcoholism, attention deficit hyperactivity disorder, bipolar disorder, clinical depression, drug abuse, Parkinson disease, Tourette syndrome and Schizophrenia. Stimulant medications, such as those used to treat ADHD, and drugs of abuse such as amphetamine bind to SLC6A3 and inhibit reuptake of dopamine. Genetic variants of SLC6A3 may influence levels of gene expression and/or ability of drugs to bind to SLC6A3 protein. The gene that encodes the SLC6A3 protein is located on human chromosome 5, consists of 15 coding exons, and is roughly 64 kpb long. It is believed that the associations between SLC6A3 and dopamine related disorders has come from a genetic polymorphism in the SLC6A3 gene, which influences the amount of protein expressed.

What are lacking are tools for predicting the likelihood that a particular patient will be responsive to a therapeutic SLC6A3 agent, and in particular, identifying agents to which the SLC6A3 therapeutic agent will be sensitive or resistant.

CYP2C9—

CYP2C9 (encoding cytochrome P450 2C9) is a liver drug metabolizing enzyme, involved in metabolism of ~20% of pharmaceuticals. CYP2C9 is a member of the cytochrome P450 mixed-function oxidase system and is involved in the metabolism of xenobiotics in the body. CYP2C9 is involved in the metabolism of several groups of drugs, such as, for example, non-steroidal anti-inflammatory drugs (NSAIDs). Genetic polymorphism exists for CYP2C9 expression and there is a belief that approximately 1-3% of Caucasian populations are poor metabolizers with no CYP2C9 function.

What are lacking are tools for predicting the likelihood that a particular patient will be responsive to a therapeutic CYP2C9 agent, and in particular, identifying agents to which the CYP2C9 agent will be sensitive or resistant.

Such tools would likewise enable the identification of new drugs that modulate expression of genes that affect chemosensitivity, particularly new agents that alter expression of these genes to overcome drug resistance or enhance chemosensitivity.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

SUMMARY

In a very broad aspect, the disclosure provides for a method for predicting a subject's risk factors for an ACE-related disorder, such as, but not limited to cardiovascular diseases and/or a subject's responsiveness to a therapeutic agent targeting the subject's renin-angiotension system (for example, ACE inhibitors angiotension receptor blockers (ARBS) and the like). The method includes detecting the allelic status of one or more polymorphisms in a nucleic acid sample of the subject, wherein the polymorphism is selected from the group of (i) ACE-associated SNPs rs4290, rs7214530, rs7213516, rs4309, rs4343 or combinations thereof; or, (ii) a SNP in linkage disequilibrium with one or more SNPs listed in (i). In such a method, the allelic status of the polymorphism in the subject is predictive of the subject's risk factors for an ACE-related disorder.

In one embodiment, the method further includes the step of correlating the allelic status of the polymorphism in the subject with the allelic status of the polymorphism in a reference population to predict the subject's risk factors for an ACE-related disorder.

In another embodiment, the method further includes the step of correlating the allelic status of the polymorphism in the subject with the allelic status of the polymorphism in a reference population to predict whether the subject has risk factors for an ACE-related disorder.

In a particular embodiment, the disclosure provides for a method of screening a subject for a prognostic biomarker, comprising detecting the allelic status of one or more polymorphisms in a nucleic acid sample of the subject, wherein the polymorphism is one or more of:
  (i) ACE-associated SNPs rs4290, rs7214530, rs7213516 or combinations thereof; or,
  (ii) a SNP in linkage disequilibrium with one or more SNPs listed in (i).
In this method, the allelic status of the polymorphism in the subject is predictive of the prognostic outcome of the subject.

In a particular embodiment, the disclosure provides for a method of screening a subject for a prognostic biomarker, comprising detecting the allelic status of one or more polymorphisms in a nucleic acid sample of the subject, wherein the polymorphism is one or more of:
  (i) SOD2-associated SNPs rs4880, rs5746092 or combinations thereof; or,
  (ii) a SNP in linkage disequilibrium with one or more SNPs listed in (i), wherein the allelic status of the polymorphism in the subject is predictive of the subject's risk for having or developing the SOD2-related disorder.

In a particular embodiment, the disclosure provides for a method of screening a subject for a prognostic biomarker, comprising detecting the allelic status of one or more polymorphisms in a nucleic acid sample of the subject wherein the polymorphism is one or more of:
  (i) SLC6A3-associated rs27072, rs6347 or combinations thereof; or,
  (ii) a SNP in linkage disequilibrium with one or more SNPs listed in (i), wherein the allelic status of the polymorphism in the subject is predictive of the subject's risk for having or developing the SLC6A3-related disorder.

In a particular embodiment, the disclosure provides for a method of screening a subject for a prognostic biomarker, comprising detecting the allelic status of one or more polymorphisms in a nucleic acid sample of the subject, wherein the polymorphism is one or more of:

(i) CYP2C9-associated rs1057911, rs9332242, rs2017319 or combinations thereof; or, (ii) a SNP in linkage disequilibrium with one or more SNPs listed in (i), wherein the allelic status of the polymorphism in the subject is predictive of the subject's risk for having or developing the CYP2C9-related disorder.

In one embodiment, the method further includes the step of correlating the allelic status of the polymorphism in the subject with the allelic status of the polymorphism in a reference population to predict the prognostic outcome of the subject.

In another embodiment, the method further includes the step of correlating the allelic status of the polymorphism in the subject with the allelic status of the polymorphism in a reference population to predict whether the subject has a greater or lesser risk factors for an ACE-related disorder.

In another embodiment, the method further includes the step of correlating the allelic status of the polymorphism in the subject with the allelic status of the polymorphism in a reference population to predict the subject's response to treatment.

In one embodiment, the disorders for which a therapeutic ACE inhibitor may be indicated includes, but is not limited to, one or more of the following: hypertensive treatment for heart disease, lowering blood pressure, myocardial infarction, hypertension or renal crisis in relation to scleroderma, prevention of kidney damage in diabetics, and Alzheimer's disease.

The SNPs identified herein can be used in combination with additional predictive tests including, but not limited to, additional SNPs, mutations, and clinical tests.

The disclosure also provides for a method for finding a functional polymorphism in a target gene implicated a in subject's risk factors for an ACE-related disorder, comprising: (i) providing a sample of a target tissue expressing the target gene; (ii) measuring the target gene's allelic mRNA expression imbalance (AEI) by quantitatively measuring the relative amounts of mRNA generated from each of two alleles in a transcribed region of the target gene and comparing the mRNA expression of one allele against the other allele to obtain an AEI ratio; and (iii) using the AEI ratio as a phenotype to scan the target gene for regions containing polymorphisms. Accordingly, a significant association between the AEI ratio and the polymorphism indicates that the polymorphism is a functional polymorphism that can serve as a biomarker for assessing a subject's risk factors for an ACE-related disorder.

The present disclosure also relates to a kit comprising useful components for practicing the present method. A useful kit can contain oligonucleotide probes specific for ACE alleles. The kit can also include instructions for correlating the assay results with the subject's responsiveness to a therapeutic agent, the subject's prognostic outcome, or the probability of success or failure of a particular drug treatment in the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention can be more fully understood from the following detailed description, the drawings and the Sequence Descriptions that form a part of this application. The sequence descriptions and Sequence Listing attached hereto comply with the rules governing nucleotide and/or amino acid sequence disclosures in patent applications as set forth in 37 CFR §§1.821-1.825. The Sequence Descriptions contain the three letter codes for amino acids as defined in 37 CFR §§1.821-1.825, which are incorporated herein by reference.

The reference haplotype is G-T-C, while the variant constructs contain 1-3 minor alleles (G-T-T, G-G-C, G-G-T, A-G-C, A-G-T). In BAEC, 0.8 µg plasmids were co-transfected with 40 ng Renilla luciferase plasmid using either Lipofectamine or Fugen reagent, and activity was measured by Dual-Glo luciferase assay kit (Promega). Luciferase activities from fused-pGL3 vector were normalized using Renilla luciferase activity as an internal control. *P<0.05; **P<0.001 compared to reference haplotype G-T-C. In HEK293 cells, various amounts of plasmid were transfected using Lipofectamine, with no differences observed between all conditions.

Figure 4:
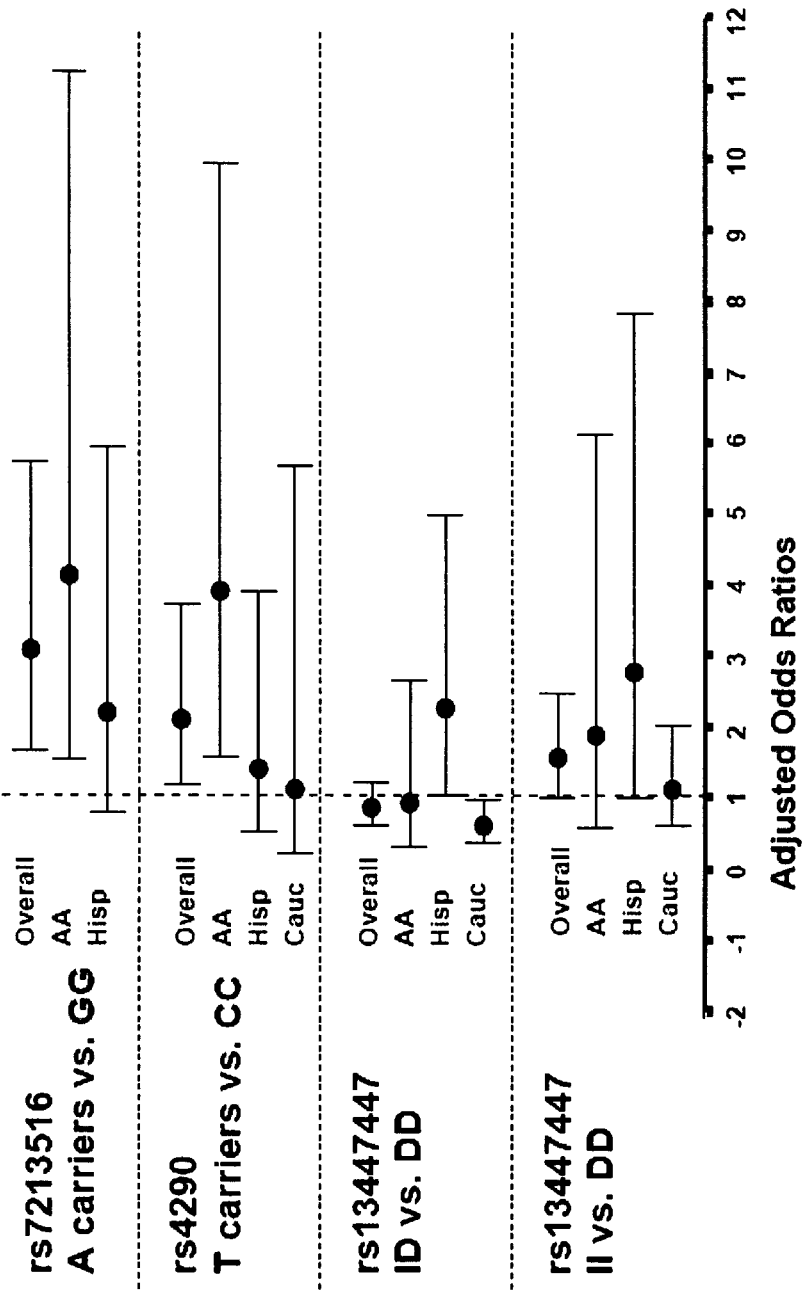

FIG. 4. Odds ratios of three polymorphisms for primary outcome in the overall population and within each race/ethnicity group. The three polymorphisms are promoter SNPs rs7213516 and rs4290, and intron 15 SNP rs13447447 (I/D). Odds ratios were adjusted for age, sex, race/ethnicity, BMI, smoking, INVEST treatment strategy, previous myocardial infarction, previous stroke, heart failure, diabetes, renal insufficiency, baseline SBP, diuretic use, and ACE inhibitor use.

Figure 5:
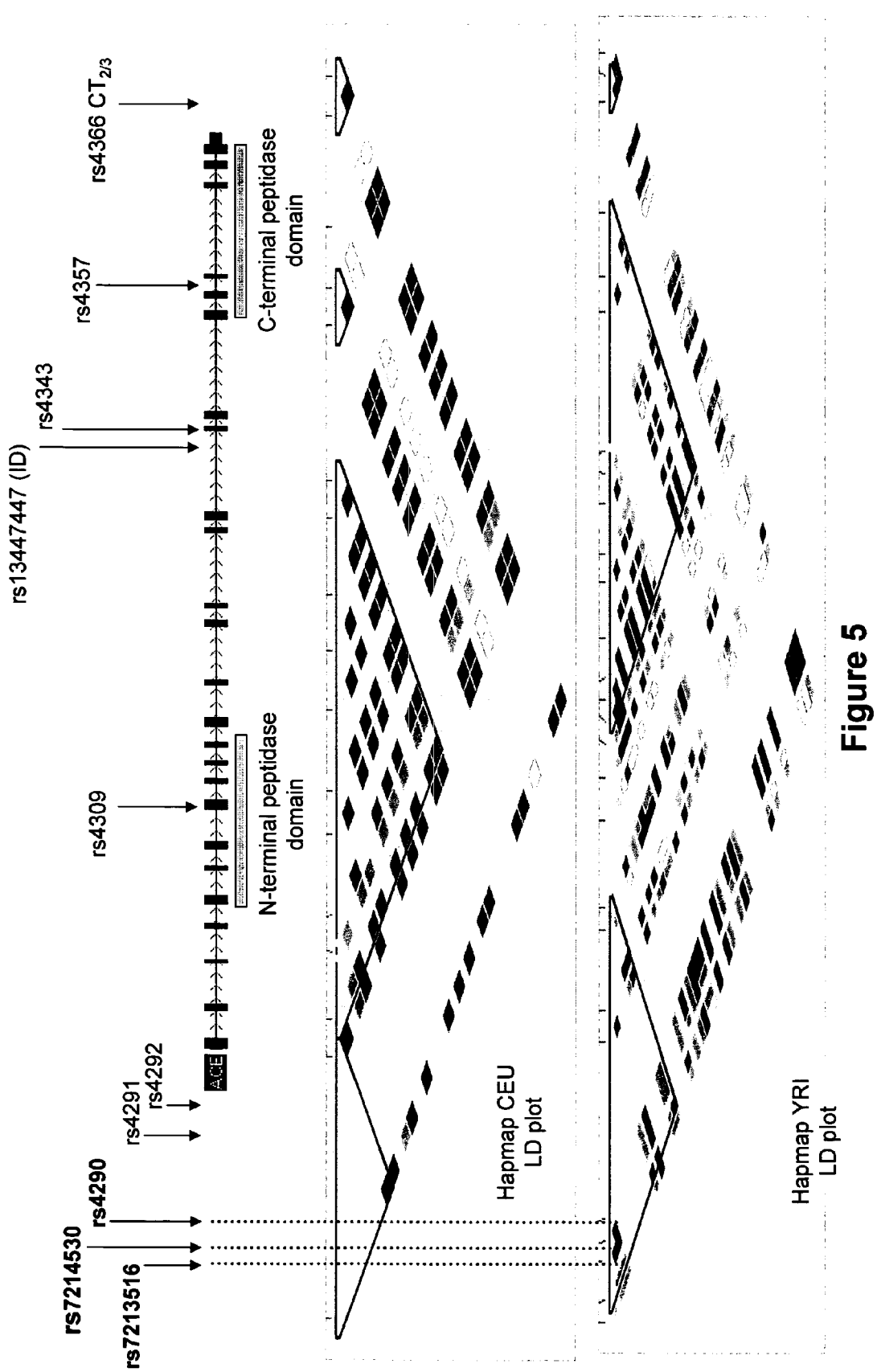

FIG. 5. ACE gene structure (UCSC genome browser) and location of polymorphisms tested in this study. The boxes indicate the exons coding for the two peptidase domains in the full length ACE isoform. Overviews of HapMap LD in the gene region for individuals from Utah of Northern-European ancestry (CEU) and from Yoruba, Nigeria (YRI) are shown at bottom (Haploview).

FIGS. 6a and 6b. Schematics of the allelic expression imbalance (AEI) assay used to uncover cis-acting functional alleles. Shown here, marker SNP rs4309 (C/T) is used in the SNaPshot reaction for both gDNA and mRNA. Peak area ratios represent allelic ratios in gDNA and mRNA (after conversion to cDNA).

Figure 7:
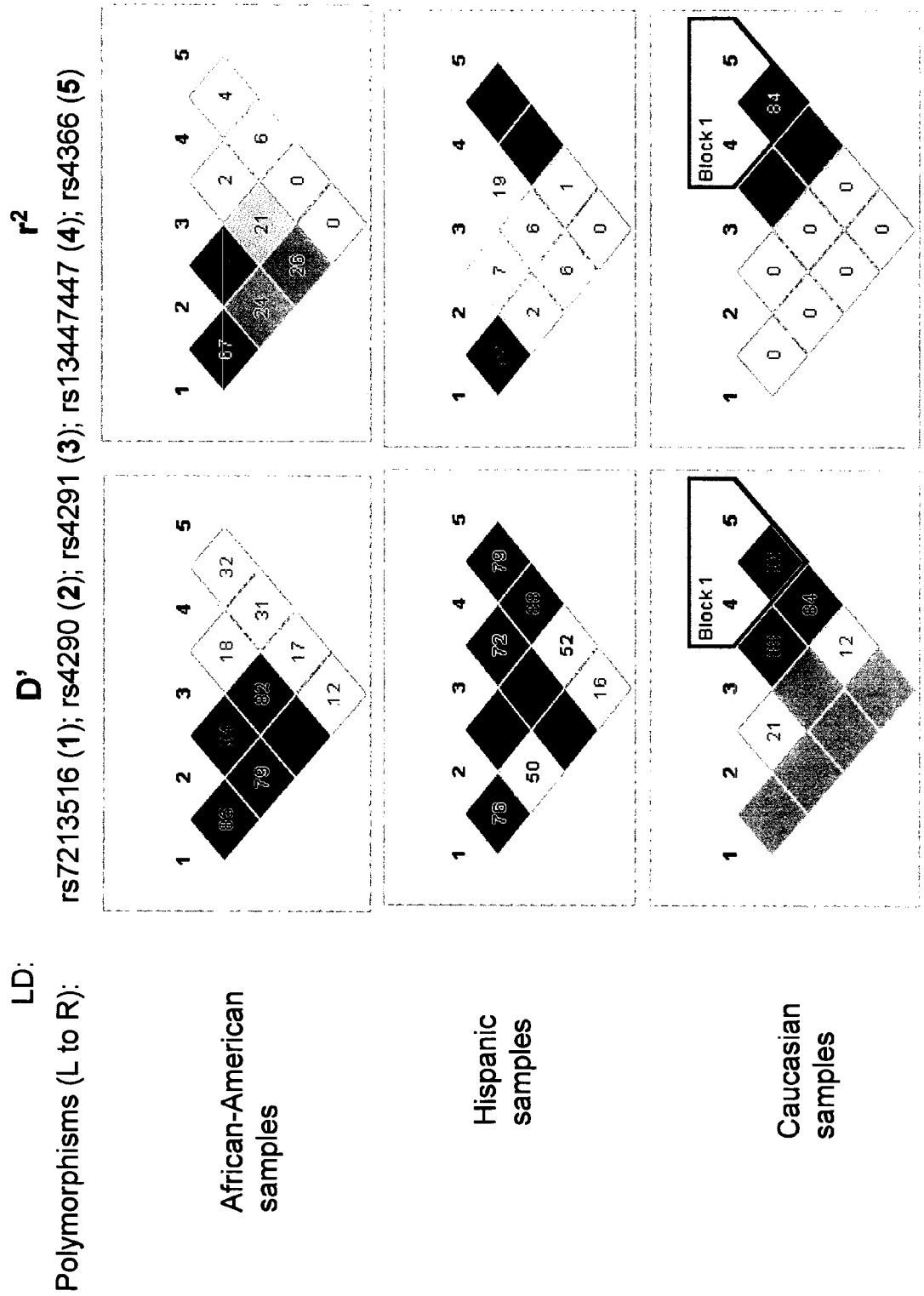

FIG. 7. LD structure of polymorphisms in the INVEST-GENES clinical genetic association study. Values for D' and r² are provided and color coded; the light blue boxes indicate very low allele abundance preventing calculation of D'.

Figure 8:
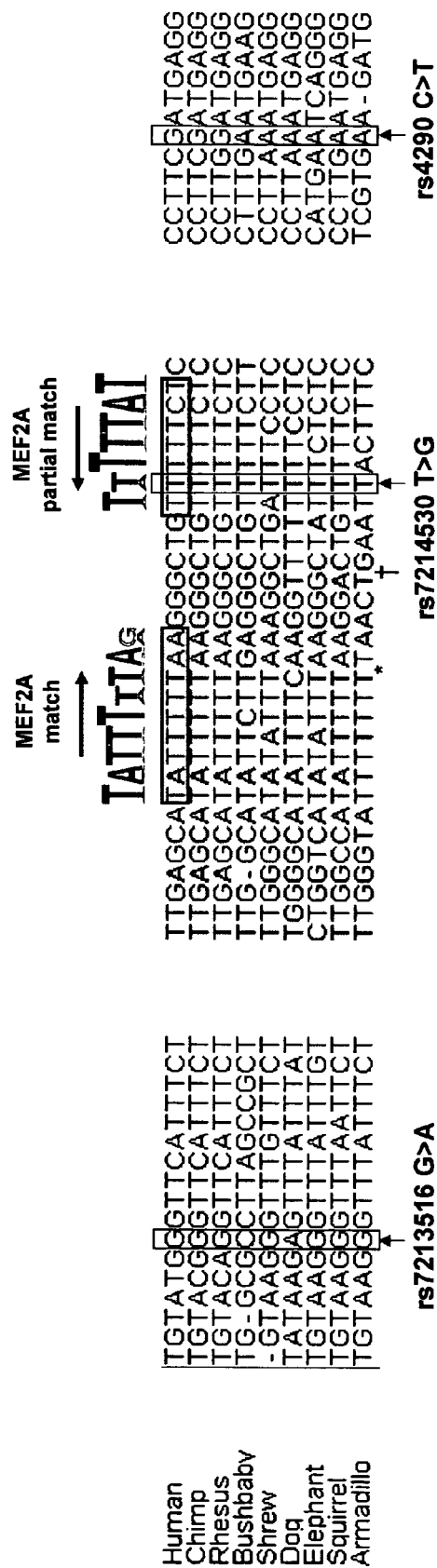

FIG. 8. Promoter sequence alignments and TF binding sites. The three promoter SNPs rs7213516 (G/A), rs7214530 (T/G) and rs4290 (C/T) are located −2883, −2828 and −2306 bp upstream of the transcription start site (+1). The predicted MEF2A transcription factor binding sites based on the JASPAR database position-weight matrices are shown in detail. Sequence alignments (CLUSTALW) are based on genomic matches identified by BLAST of the human promoter region (* indicates a 1 bp insert in rhesus, dog, elephant, and armadillo sequences; \ indicates a 9 bp insert in dog and armadillo sequences). Human [SEQ ID NOS 70, 34 and 278, respectively, in order of appearance], Chimp [SEQ ID NOS 71, 270 and 279, respectively, in order of appearance], Rhesus [SEQ ID NOS 72, 271 and 280, respectively, in order of appearance], Bushbaby [SEQ ID NOS 76, 272 and 281, respectively, in order of appearance], Shrew [SEQ ID NOS 73, 273 and 282, respectively, in order of appearance], Dog [SEQ ID NOS 74, 274 and 283, respectively, in order of appearance], Elephant [SEQ ID NOS 75, 275 and 284, respectively, in order of appearance], Squirrel [SEQ ID NOS 77, 276 and 285, respectively, in order of appearance], Armadillo [SEQ ID NOS 78, 277 and 286, respectively, in order of appearance].

FIG. 9. Schematic illustration of ACE gene structure and relevant genetic polyporphism (chromosome 17q.23.3) (not to scale).

FIG. 10. Table 1. Unadjusted and adjusted odds ratios and 95% confidence intervals for secondary outcomes by genotype FIGS. 11a and 11b. Tables 2A and 2B. Polymorphisms analyzed in this study, and minor allele frequencies observed in the 65 heart tissues (Table 2A, FIG. 11a) and in the INVEST-GENES cohort (Table 2B, FIG. 11b), sorted by race/ethnicity. The P values indicate the level of significance for interethnic differences in minor allele frequencies.

FIG. 12. Table 3. Baseline characteristics for the INVEST-GENES case and control patients.

FIG. 13. Table 4. Oligonucleotide sequences used in genotyping and allelic expression imbalance (AEI) assays for ACE that employed primer extension technology. Underlined nucleotides were intentionally mismatched against the reference sequence.

FIG. 14. Table 5. Oligonucleotide sequences employed in genotyping ACE SNPs by the GC-clamp method described in Papp et al.

FIG. 15. Table 6. Oligonucleotides sequences employed in ACE Pyrosequencing genotyping.

FIG. 16. Table 7. Oligonucleotide primers used in the amplification and direct sequencing of the ACE upstream gene region and cDNA.

FIG. 17. Table 8. FAM-labeled oligos and related oligos used in genotyping ACE polymorphisms.

FIG. 18. Table 9. Oligonucleotides used in the measurement of ACE expression by RT-PCR, including one that spans cDNA exons.

FIG. 19. Table 10. Oligonucleotide sequences used in genotyping and allelic expression imbalance (AEI) assays for SOD2 that employed primer extension technology.

FIG. 20. Table 11. A list of SNPs used in the SLC6A3 example herein.

FIG. 21. Table 12. A list of SNPs used in the CYP2C9 example herein.

Figure 22:
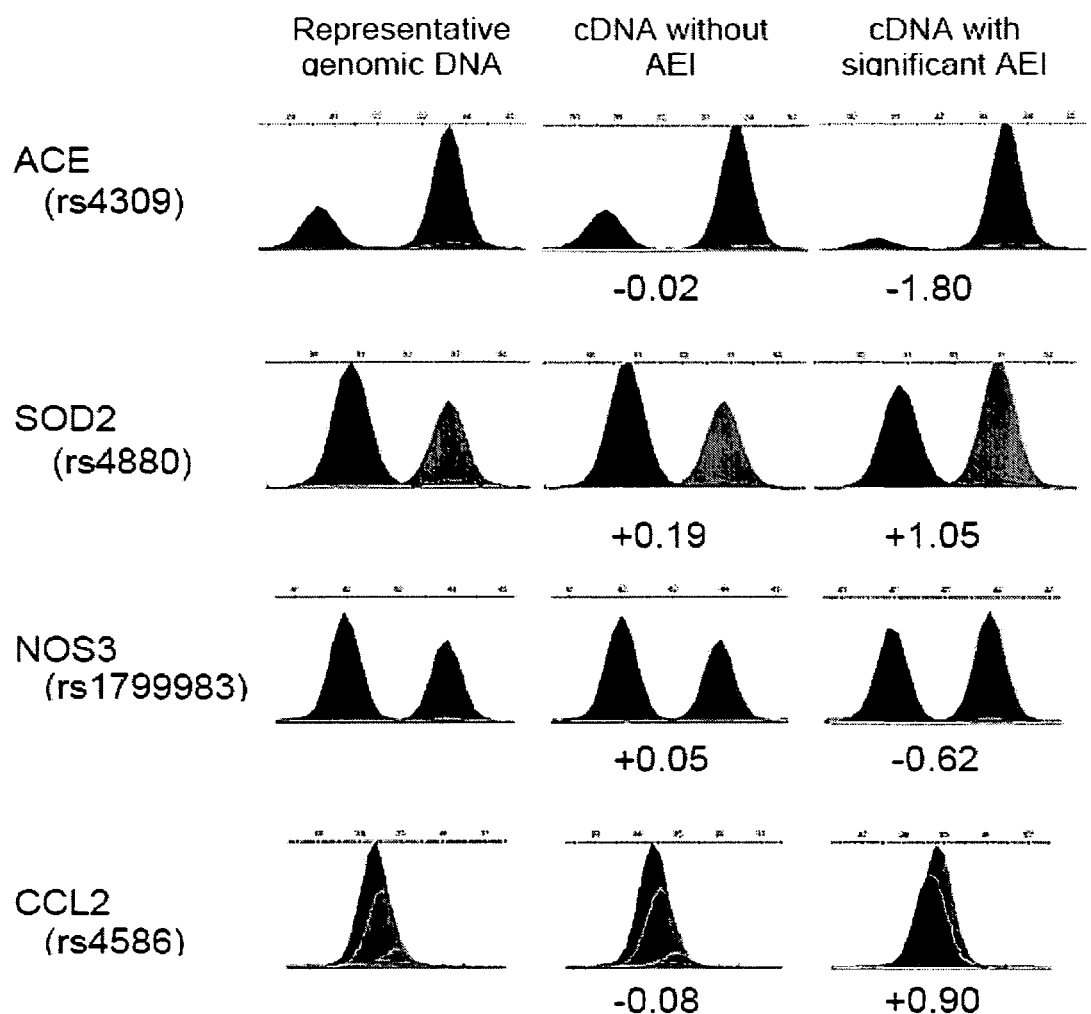

FIG. 22—Results of AEI analysis for ACE, SOD2, NOS3 and CCL2, in heart left ventricular tissues. Each peak represents a distinct allele measured in genomic DNA or cDNA from a single heterozygous individual. The selected samples (columns, left to right) represent the typical genomic DNA ratio observed, a cDNA showing insignificant deviation from the expected ratio and a cDNA sample showing highly significant deviation from unity. Normalization to the average genomic DNA is used in the calculation of AEI values (cDNA values listed as major:minor allele on a log 2 scale) and accounts for differences in fluorescent dideoxynucleotide incorporation efficiencies and fluorescent yields. See FIG. 26—Table 13, for a list of genes reported here and FIG. 27—Table 14 for marker SNPs and genes showing significant AEI results.

Figure 23:
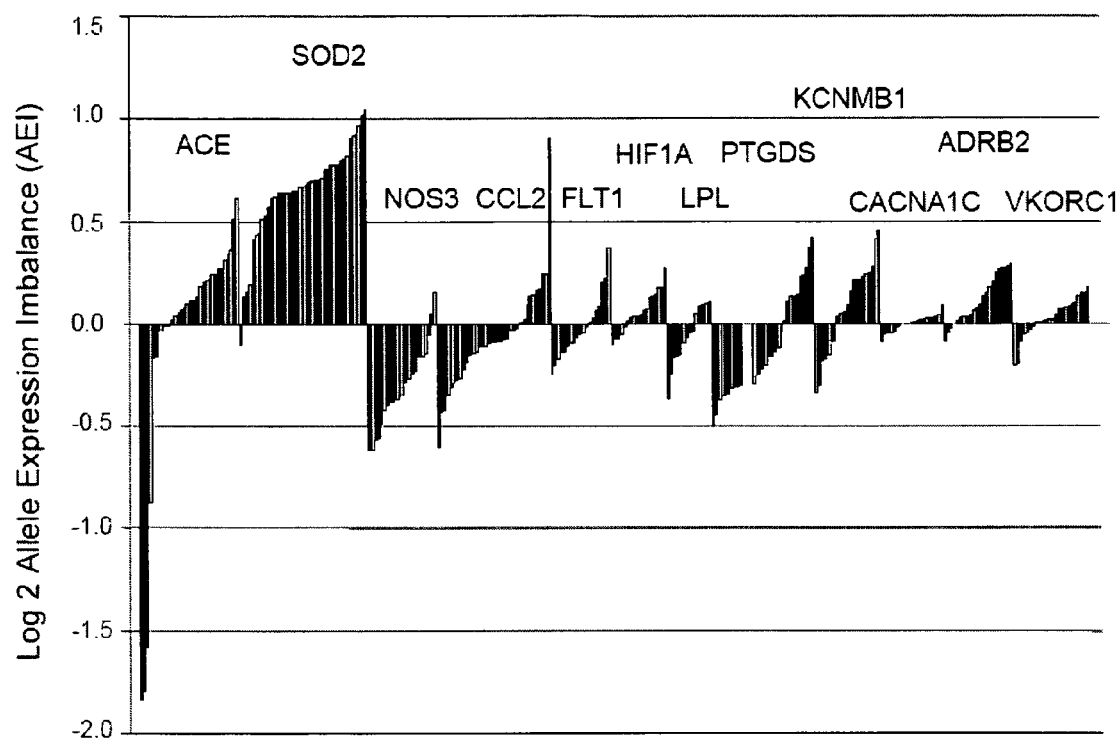

FIG. 23. Allelic mRNA expression ratios (major allele over minor allele, normalized to the mean allelic ratio in genomic DNA) measured in heart failure samples for 12 cardiovascular candidate genes. Results for individual samples are displayed with the magnitude and direction of AEI indicated on a log 2 scale (y-axis). Potential AEI in individual samples is indicated by ratios >(+0.3) log 2 or <(−0.3) log 2, a cutoff arrived at by analysis of the extent of variation in genomic DNA ratios. For the present survey study we considered ratios >(+0.5) log 2 or <(−0.5) log 2 to represent significant AEI.

Figure 24:
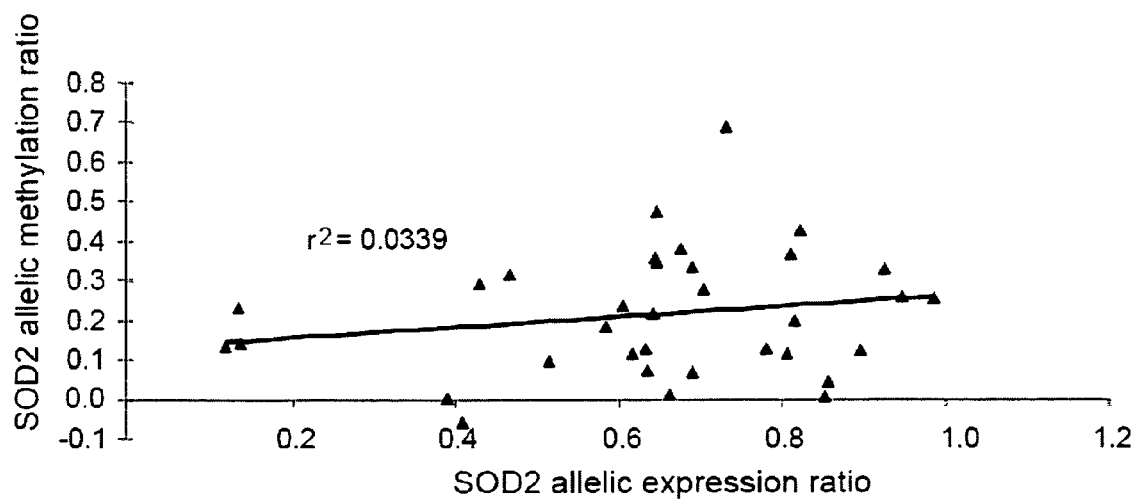

FIG. 24. Lack of correlation between SOD2 allelic mRNA expression ratios and allelic CpG methylation ratios in 34 heart tissue samples. Allelic methylation ratios were determined from triplicate assays using Hpa II digestion of the genomic DNA region containing rs4880 (only non-methylated DNA is cut), followed by SNaPshot analysis of the allelic ratios for uncut genomic DNA.

FIG. 25. Computed changes of mRNA folding (minimum free energy conformations) induced by all transitions (SNP generated by C<>T and G<>A substitutions) in the transcribed exonic domains of OPRM1 mRNA. The arrow indicates the location of the functional SNP A118G, affecting mRNA levels in human brain (18). The x-axis denotes the nucleotide position in the mature OPRM1 mRNA (cDNA), while the y-axis represent a scale of the extent by which predicted mRNA folding is affected by any given transition. Conformations were calculated for wild-type and mutant sequences using Mfold, and then the sum of the differences in the Mfold single-strandedness count measure at each nucleotide was computed both globally (across the full mRNA structure, each point shown here) and in more regional sliding windows of different sizes. Sliding windows and analysis of both types of transversions at each position (pyrimidine<>Opurine), as well as A>G transitions alone all gave very similar results (data not shown).

FIG. 26. Table 13. A list of candidate genes tested for the presence of AEI in Example II herein.

FIG. 27. Table 14. Gene showing significant allelic mRNA expression ratios (at least one sample showing minimally ±0.2$^{0.5}$, or ~40% AEI in either direction.

FIG. 28. Table 15. Genotyping of suspected functional polymorphisms compared with AEI data.

FIG. 29. Table 16. List of candidate genes analyzed in Example II, grouped by indication (disease or pharmacology). List of candidate genes analyzed in this study, grouped by indication (disease or pharmacology). Marker SNPs are all located in transcribed regions of the mature mRNA, or a splice variant. For some genes more than one marker SNP and tissue were used.

FIG. 30. Table 17. List of oligonucleotide primers used for PCT amplification and SNaPshot primer extension reactions.

FIG. 31. mRNA sequence of the ACE gene [SEQ ID NO: 261 (DNA) and SEQ ID NO: 287 (protein)].

FIG. 32. mRNA sequence of the SOD2 gene[SEQ ID NO: 262 (DNA) and SEQ ID NO: 288 (protein)].

FIG. 33. mRNA sequence of the SLC6A3 gene[SEQ ID NO: 263 (DNA) and SEQ ID NO: 289 (protein)].

FIG. 34. mRNA sequence of the CYP2C9 gene [SEQ ID NO: 264 (DNA) and SEQ ID NO: 290 (protein)].

DETAILED DESCRIPTION OF THE INVENTION

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

All publications, patent applications, patents, and other references mentioned herein are incorporated by reference in their entirety. The disclosure of all patents, patent applications (and any patents that issue thereon, as well as any corresponding published foreign patent applications), GenBank and other accession numbers and associated data, and publications mentioned throughout this description are hereby incorporated by reference herein. It is expressly not admitted, however, that any of the documents incorporated by reference herein teach or disclose the present invention.

The present invention may be understood more readily by reference to the following detailed description of the embodiments of the invention and the Examples included herein. However, before the present methods, compounds and compositions are disclosed and described, it is to be understood that this invention is not limited to specific methods, specific cell types, specific host cells or specific conditions, etc., as such may, of course, vary, and the numerous modifications and variations therein will be apparent to those skilled in the art. It is also to be understood that the terminology used herein is for the purpose of describing specific embodiments only and is not intended to be limiting.

Accordingly, the disclosure provides diagnostic and prognostic methods, compositions, assays, and kits useful for predicting the phenotype of a subject's risk factors for cardiovascular diseases and/or a subject's responsiveness to therapeutic ACE inhibitors. The methods also include predicting the prognostic outcome of the subject, as well as the subject's responsiveness to drug treatments. The methods and kits include determining the allelic status of polymorphisms in the ACE genes.

The disclosure also provides methods for identifying functional polymorphisms using an allele-specific mRNA expression imbalance (AEI) assay combined with SNP scanning of a target gene locus with allelic mRNA ratios as a quantitative phenotype, together with in vitro molecular genetic analysis to identify the functional polymorphisms. Also provided are a number of functional single nucleotide polymorphisms (SNPs) in the ACE gene.

AEI Assay

The question of how genetic processes interact to regulate gene expression can be addressed by measuring allelic expression imbalance (AEI). Measuring allelic mRNA expression compares one allele against the other in a relevant target tissue of the same individual. The assay quantitatively measures the relative amounts of mRNA generated from each of two alleles in physiologically relevant target tissues (e.g., specific cardiac regions) from subjects that are heterozygous for a marker SNP in the transcribed region of the gene in question. AEI indicates the presence of cis-acting factors in gene regulation and/or mRNA processing. AEI results provide a quantitative measure of the allelic differences in each individual, one allele serving as the control for the other, while canceling out any trans-acting factors. The allelic expression ratios are then used as the phenotype to scan a gene locus for regions containing functional polymorphisms. If cis-acting polymorphisms contribute to the measured AEI ratios, significant correlations should be detectable. For this analysis it is helpful to know the phasing of each SNP with the marker SNPs. As disclosed in the Examples, the inventors conducted a single locus association test between SNP genotype and allelic expression phenotype. The AEI phenotype can be represented either as present/absent; or absent/present low/present high, or as a continuous quantitative trait. Significant associations indicate that a SNP, or one closely linked, contributes to AEI, by affecting mRNA expression levels. These candidate polymorphisms, or haplotypes, are then cloned into expression vectors to determine the molecular mechanisms underlying the genetic changes where this is possible. A goal of this assay is to identify the polymorphisms that most closely account for any genetically based phenotypic differences between individuals.

Polymorphisms Linked to Function (AEI)

Using the above method, we were able to designate specific polymorphisms as biological biomarkers, used either alone or in combination with each other or with already established biomarkers. For each polymorphism in the candidate genes, we have established a link with allelic expression in human biopsy cardiac tissues as the phenotype. Obtained by scanning the entire gene in a number of individuals for polymorphisms that correlate with AEI, these polymorphisms are either directly responsible for altering mRNA expression, or they are in linkage disequilibrium or strong linkage disequilibrium with a functional SNP or SNPs. The listed polymorphisms are frequent (>5%), and have already shown statistically significant associations with clinical phenotypes. These polymorphisms therefore represent biallelic biomarkers associated with functional variants of key genes conveying susceptibility to CNS disorders and treatment outcome.

We disclose the use of AEI analysis to screen the ACE gene for functional polymorphisms. We have discovered several AEI across a number of individuals, indicating the presence of previously unknown and yet frequent functional polymorphisms.

By scanning each gene in a number of individuals we have identified polymorphisms (SNPs) most closely related to the functional variation. Because these SNPs are linked to functional defects, and occur frequently in key candidate genes implicated in cardiovascular disorders, they represent strong biomarkers for predicting individual risk and response to ACE inhibitor therapy. Because their functional significance is established, one can also analyze combinations of gene variants as risk factors, without greatly increasing the required statistical stringency for multiple comparisons.

DEFINITIONS

Unless defined otherwise, all technical and scientific terms used herein have the same meaning as commonly understood to one of ordinary skill in the art to which this disclosure belongs.

As used herein and in the appended claims, the singular forms "a," "and," and "the" include plural referents unless the context clearly dictates otherwise. Thus, for example, reference to "a polynucleotide" includes a plurality of such polynucleotides and reference to "the SNP" includes reference to one or more SNPs known to those skilled in the art, and so forth.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The term "allele" is used herein to refer to variants of a nucleotide sequence. Alleles are identified with respect to one or more polymorphic positions, with the rest of the gene sequence unspecified. For example, an allele may be defined by the nucleotide present at a single SNP; or by the nucleotides present at a plurality of SNPs, also termed haplotypes. A biallelic polymorphism has two forms. Diploid organisms may be homozygous or heterozygous for an allelic form.

For convenience, the allele present at the higher or highest frequency in the population will be referred to as the "main" or "wild-type" allele; less frequent allele(s) will be referred to as "minor" or "variant" allele(s).

Assessing the "allelic status" of a polymorphism refers to determining whether a subject is heterozygous (has one minor allele and one main allele), homozygous for the minor allele or homozygous for the main allele.

A "gene" refers to a segment of genomic DNA that contains the coding sequence for a protein, wherein the segment may include promoters, exons, introns, and other untranslated regions that control expression.

A "genotype" is an unphased 5' to 3' sequence of nucleotide pair(s) found at a set of one or more polymorphic sites in a locus on a pair of homologous chromosomes in a subject.

The term "genotyping" a sample or a subject for a polymorphism involves determining the specific allele or the specific nucleotide(s) carried by an individual at a biallelic marker.

The term "haplotype" refers to a combination of alleles present in an individual or a sample on a single chromosome. In the context of the present disclosure, a haplotype refers to a combination of biallelic marker alleles found in a given individual and which may be associated with a phenotype.

"Haplotyping" is the process for determining one or more haplotypes in a subject and includes use of family pedigrees, molecular techniques and/or statistical inference.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A polymorphism may comprise a substitution, deletion or insertion of one or more nucleotides. A single nucleotide polymorphism (SNP) is a single base pair change. Typically, a single nucleotide polymorphism is the replacement of one nucleotide by another nucleotide at the polymorphic site. Deletion of a single nucleotide or insertion of a single nucleotide, also give rise to single nucleotide polymorphisms. In the context of the present disclosure, "single nucleotide polymorphism" refers to a single nucleotide substitution. Typically, between different genomes or between different individuals, the polymorphic site may be occupied by two different nucleotides.

The term "biallelic polymorphism," "bialleleic marker," or "biomarker" are used interchangeably and refer to a polymorphism having two alleles at a fairly high frequency in the population, sometimes a single nucleotide polymorphism. Typically, the frequency of the less common allele of the biallelic polymorphism of the present disclosure has been validated to be greater than 1%, sometimes the frequency is greater than 10%, 20% (i.e. heterozygosity rate of at least 0.32), or 30% (i.e. heterozygosity rate of at least 0.42).

The term "mutation" refers to a difference in DNA sequence between or among different genomes or individuals that causes a functional change and which can have a frequency below 1%. Sequence variants describe any alteration in DNA sequence regardless of function or frequency.

"Linkage Disequilibrium" ("LD") refers to alleles at different loci that are not associated at random, i.e., not associated in proportion to their frequencies. If the alleles are in positive linkage disequilibrium, then the alleles occur together more often than expected assuming statistical independence. Conversely, if the alleles are in negative linkage disequilibrium, then the alleles occur together less often than expected assuming statistical independence. As used herein, "strong linkage disequilibrium" is defined by D' of >0.8.

As used interchangeably herein, the terms "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide.

The term "purified" is used herein to describe a polynucleotide or polynucleotide vector of the disclosure which has been separated from other compounds including, but not limited to other nucleic acids, carbohydrates, lipids and proteins (such as the enzymes used in the synthesis of the polynucleotide), or the separation of covalently closed polynucleotides from linear polynucleotides.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

The term "heterozygosity rate" is used herein to refer to the incidence of individuals in a population, which are heterozygous at a particular allele. In a biallelic system, the heterozygosity rate is on average equal to 2 Pa(1-Pa), where Pa is the frequency of the least common allele. In order to be useful in genetic studies, a genetic biomarker should have an adequate level of heterozygosity to allow a reasonable probability that a randomly selected person will be heterozygous.

The term "upstream" refers to a location which, is toward the 5' end of the polynucleotide from a specific reference point. The term "downstream" refers to a location which is toward the 3' end of the polynucleotide from a specific reference point.

The terms "base paired" and "Watson & Crick base paired" are used interchangeably herein to refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds (See Stryer, L., Biochemistry, 4th edition, 1995; incorporated herein by reference).

The terms "complementary" or "complement thereof" are used herein to refer to the sequences of polynucleotides which are capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase, or in a single nucleotide extension reaction for the measurement of AEI.

The term "probe" denotes a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified.

The primers and probes can be prepared by any suitable method, including, for example, cloning and restriction of appropriate sequences and direct chemical synthesis. The probes and primers can comprise nucleic acid analogs such as, for example, peptide nucleic acids, locked nucleic acid (LNA) analogs, and morpholino analogs. The 3' end of the probe can be functionalized with a capture or detectable label to assist in detection of a polymorphism.

Any of the oligonucleotides or nucleic acid of the disclosure can be labeled by incorporating a detectable label measurable by spectroscopic, photochemical, biochemical, immunochemical, or chemical means. For example, such labels can comprise radioactive substances ($^{32}P$, $^{35}S$, $^{3}H$, $^{125}I$) fluorescent dyes (5-bromodesoxyuridin, fluorescein, acetylaminofluorene, digoxigenin), biotin, nanoparticles, and the like. Such oligonucleotides are typically labeled at their 3' and 5' ends.

Probes can be used to detectably distinguish between target molecules differing in structure. Detection can be accomplished in a variety of different ways depending on the type of probe used and the type of target molecule. Thus, for example, detection may be based on discrimination of activity levels of the target molecule, but typically is based on detection of specific binding. Examples of such specific binding include antibody binding and nucleic acid probe hybridization. Thus, for example, probes can include enzyme substrates, antibodies and antibody fragments, and nucleic acid hybridization probes. Thus, in one embodiment, the detection of the presence or absence of the at least one variance involves contacting a target polymorphic site with a probe, typically an oligonucleotide probe, where the probe hybridizes with a form of the target nucleic acid containing a complementary base at the variance site as compared to hybridization to a form of the target nucleic acid having a non-complementary base at the variance site, where the hybridization is carried out under selective hybridization conditions. Such an oligonucleotide probe may span two or more variance sites. Unless otherwise specified, an oligonucleotide probe can include one or more nucleic acid analogs, labels or other substituents or moieties so long as the base-pairing function is retained.

A "control population" refers to a group of subjects or individuals who are predicted to be representative of the genetic variation found in the general population.

A "subject" comprises an individual (e.g., a mammalian subject or human) whose genotypes or haplotypes or response to treatment or disease state are to be determined.

A "nucleic acid sample" includes blood, serum, plasma, cerebrospinal fluid, urine, saliva, and tissue samples.

The term "phenotype" refers to any biochemically, anatomically, and clinically distinguishable, detectable or otherwise measurable property of an organism such as symptoms of, or susceptibility to a disease for example. Typically, the term "phenotype" is used herein to refer to symptoms of, or susceptibility to a cardiovascular disorder; or to refer to an individual's response to a therapeutic agent; or to refer to symptoms of, or susceptibility to side effects to a therapeutic agent. A "less severe phenotype" is defined as a less severe form of a cardiovascular disorder, or a form of the cardiovascular disorder that is more responsive to treatment, displays less side effects with treatment, has better prognosis, is not recurrent, or has a combination of these characteristics. A "more severe phenotype" is defined as a more severe form of a cardiovascular disorder, or a form of the disorder that is less responsive to treatment, displays more side effects with treatment, has worse prognosis, is recurrent, or has a combination of these characteristics. In general, the more severe phenotype is a disease state with profound consequences to the patient's life quality and requires more aggressive therapy.

A subject who is at risk for "having or developing a cardiovascular disorder" includes a subject with no clinical signs or symptoms of a cardiovascular disorder but with a strong family history of such disorders, a subject who exhibits clinical signs or symptoms associated with a cardiovascular disorder, or a subject who has been clinically diagnosed as having a cardiovascular disorder.

The term "prognosis" as used herein refers to predicting the course or outcome of a condition in a subject. This does not refer to the ability to predict the course or outcome of a condition with 100% accuracy, or even that a given course or outcome is predictably more or less likely to occur based on the pattern of biomarkers. Instead, the skilled artisan will understand that the term "prognosis" refers to an increased probability that a certain course or outcome will occur.

A "diagnostic" biomarker is a biallelic polymorphism, the allelic status of which is indicative of whether or not a subject has, or is at risk for developing, a cardiovascular disorder.

A "prognostic" biomarker is a biallelic polymorphism, the allelic status of which is predictive of the severity or prognosis of a cardiovascular disorder.

When one or more prognostic biomarkers exhibit a certain pattern in samples obtained from a subject, the pattern may signal that the subject is at an increased probability for experiencing a future event in comparison to a similar subject exhibiting a different pattern. For example, a certain pattern of prognostic biomarkers can predict an increased predisposition to an adverse outcome, or the chance of a person responding or not responding to a certain drug.

In some embodiments, a "prognostic biomarker" can predict the presence of a "prognostic indicator." For example, the presence of a minor allele of a SNP (prognostic biomarker) is indicative of a lower mRNA expression (prognostic indicator) in a target tissue.

The term "ACE-related disorder" as used herein refers to any ACE-related disorder comprising one or more of the following: cardiovascular diseases, hypertension, myocardial infarction, angioedema, altered kidney function, Alzheimer's, and/or responsiveness to a therapeutic targeting the subject's renin-angiotensin system, including, but not limited to ACE inhibitors, beta blockers, angiotensin receptor blockers (ARBs).

The term "cardiovascular disorder" as used herein refers to any disorder in which an increase or decrease in ACE levels, which can lead to hypertension, heart disease, heart failure, myocardial infarction, renal pathophysiology, diabetes, and related pathologies.

All the above disorders have their usual meaning in the art, or are defined according to "The Merck Manual of Diagnosis and Therapy" Seventeenth Edition, 1999, Ed. Keryn A. G. Lane, pp. 1503-1598, incorporated herein by reference.

"Treatment" as used herein means the medical management of a subject, e.g., a human patient, with the intent to cure, ameliorate, stabilize, or prevent a disease, pathological condition, or disorder. This term includes active treatment, that is, treatment directed specifically toward the improvement or associated with the cure of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. "Treatment" also includes symptomatic treatment, that is, treatment directed toward constitutional symptoms of the associated disease, pathological condition, or disorder. "Treatment" also includes the act of not giving a subject a contra-indicated therapeutic agent.

The terms "correlating" as used herein refers to comparing the allelic status of a polymorphism in a subject to the allelic status of the polymorphism in a reference population. The reference population may be persons known to be free of a given condition, i.e., "normal individuals," or may be persons known to suffer from, or to be at risk of developing, a given mental disorder, persons known to have a form of the mental disorder with better or worse outcome, or persons known to respond to or be resistant to a certain treatment. For example, a SNP pattern in a patient sample can be compared to a SNP pattern known to be associated with response to a certain depression medication. By correlating the sample's biomarker pattern with the reference pattern, the skilled artisan can predict whether the patient will respond to a certain medication, and prescribe accordingly.

In this method, the allelic status of the polymorphism in the subject is predictive of the prognostic outcome.

In one embodiment, the method further includes the step of correlating the allelic status of the polymorphism in the subject with the allelic status of the polymorphism in a reference population to predict the prognostic outcome of the subject.

In another embodiment, the method further includes the step of correlating the allelic status of the polymorphism in the subject with the allelic status of the polymorphism in a reference population to predict whether the subject has a greater or less severe risk factors for cardiovascular diseases and/or responsiveness to therapeutic agents.

In another embodiment, the method further includes the step of correlating the allelic status of the polymorphism in the subject with the allelic status of the polymorphism in a reference population to predict the subject's response to treatment.

The SNPs identified herein can be used in combination with additional predictive tests including, but not limited to, additional SNPs, mutations, and clinical tests. The SNPs can be those provided herein, and discussed in detail in the Examples. The SNPs can also be SNPs in positive linkage disequilibrium with any of the SNPs provided herein.

The present invention is further defined in the following Examples, in which parts and percentages are by weight and degrees are Celsius, unless otherwise stated. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; 2ed.; Cold Spring Harbor Laboratory Press: Cold Spring Harbor, N.Y., 1989). It should be understood that these Examples, while indicating preferred embodiments of the invention, are given by way of illustration only.

From the discussion and the Examples herein, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein, will be apparent to those skilled in the art from the foregoing description. Such modifications are also intended to fall within the scope of the appended claims. All publications, including patents and non-patent literature, referred to in this specification are expressly incorporated by reference herein.

EXAMPLE I

ACE

Accordingly, the disclosure provides for a method for predicting a subject's risk factors for cardiovascular diseases and/or a subject's responsiveness to therapeutic ACE inhibitors.

The method includes detecting the allelic status of one or more polymorphisms in a nucleic acid sample of the subject, wherein the polymorphism is selected from the group: (i) ACE-associated SNPs rs4290, rs7214530, rs7213516 or combinations thereof; or, (ii) a SNP in linkage disequilibrium with one or more SNPs listed in (i). In this method, the allelic status of the polymorphism in the subject is predictive of the prognostic outcome of the subject.

In such a method, the allelic status of the polymorphism in the subject is predictive of the subject's risk factors for cardiovascular diseases and/or a subject's responsiveness to therapeutic ACE inhibitors.

In one embodiment, the method further includes the step of correlating the allelic status of the polymorphism in the subject with the allelic status of the polymorphism in a reference population to predict the subject's risk factors for cardiovascular diseases and/or a subject's responsiveness to therapeutic ACE inhibitors.

In another embodiment, the method further includes the step of correlating the allelic status of the polymorphism in the subject with the allelic status of the polymorphism in a reference population to predict whether the subject has a more or less severe phenotype for cardiovascular diseases and/or responsiveness to therapeutic ACE inhibitors.

In another aspect, the disclosure provides for a method of screening a subject for a prognostic biomarker for determining a subject's risk factors for cardiovascular diseases and/or a subject's responsiveness to therapeutic ACE inhibitors, comprising detecting the allelic status of one or more polymorphisms in a nucleic acid sample of the subject, wherein the polymorphism is one or more of: (i) ACE-associated SNPs rs4290, rs7214530, rs7213516 or combinations thereof; or, (ii) a SNP in linkage disequilibrium with one or more SNPs listed in (i). In this method, the allelic status of the polymorphism in the subject is predictive of the prognostic outcome of the subject.

Allelic mRNA Expression Imbalance (AEI) is Useful for Finding Functional Polymorphisms.

How genetic processes interact to regulate gene expression can be addressed by measuring allelic expression imbalance (AEI). Measuring allelic mRNA expression compares one allele against the other in a relevant target tissue of the same individual. The relative amounts of mRNA generated from each of two alleles in subjects heterozygous for a marker SNP in the transcribed region of the gene in question are quantitatively measured. AEI indicates the presence of cis-acting factors in gene regulation and/or mRNA processing. AEI results provide a quantitative measure of the allelic differences in each individual, one allele serving as the control for the other, while canceling out any trans-acting factors. The allelic expression ratios are used as the phenotype to scan a gene locus for regions containing functional polymorphisms. If cis-acting polymorphisms contribute to the measured AEI ratios, significant correlations should be detectable. Also, a single locus association test between SNP genotype and allelic expression phenotype can be conducted. The AEI phenotype is represented either as present/absent; or absent/present low/present high. Significant associations indicate that a SNP, or one closely linked, contributes to AEI, by affecting mRNA expression levels.

ACE1 Polymorphisms are Linked to Differences in ACE Expression

FIG. 31 contains the mRNA sequence for the ACE gene [SEQ ID NO: 261]. The ACE gene consists of 25 exons spanning ~25 kb and encoding a soluble or a membrane-bound protein variant with two peptidase domains (FIG. 5). Also, FIG. 9 shows a schematic illustration of ACE gene structure and relevant genetic polymorphism (chromosome 17q.23.3) (not to scale).

ACE harbors a number of polymorphisms; however, frequent nonsynonymous SNPs that affect the protein sequence are lacking, suggesting that yet to be discovered regulatory polymorphisms may contribute to genetic susceptibility in cardiovascular diseases involving ACE. To search for regulatory polymorphisms, we measured allelic mRNA expression of ACE in human cardiac tissues. In contrast to total mRNA levels, allelic mRNA ratios cancel out trans-acting factors, so that any detectable allelic expression imbalance (AEI) is a strong indicator of cis-acting regulatory factors (6-10). We can then exploit the allelic mRNA ratios as the most proximate and accurate phenotype for SNP scanning in search of regulatory polymorphism(s), followed by molecular genetic studies to address underlying mechanisms (6, 7, 10).

Genetic family studies map the heritable contribution to ACE activity and blood pressure to the region of the ACE gene, particularly in subjects of African ancestry (11,12). Moreover, allele frequencies at the ACE locus vary greatly between African-Americans and European-Americans (13).

African-Americans are at higher risk of hypertension (14) and its target organ sequelae (15), and less responsive to ACE inhibitors (16,17) while more likely to experience adverse drug effects (18). To test whether genetic variation in ACE accounts for differences among population groups, we measured allelic ACE mRNA expression in heart tissues from both Caucasians and African-Americans.

Here we report regulatory alleles affecting ACE expression that are common among African-Americans, discovered in a screen of human myocardial tissues. To assess the clinical relevance of these alleles, we conducted a clinical genetic association study in the INternational VErapamil SR Trandolapril STudy GENEtic Substudy (INVEST-GENES) (19).

Results

Allelic mRNA Expression of ACE and Association with Promoter SNPs in Heart Tissues We selected two marker SNPs (rs4309, rs4343) located in exon 8 and exon 16 of ACE FIG. 5) to measure allelic ratios of genomic DNA (gDNA) and mRNA in heart tissues using SNaPshot (Applied Biosciences) (FIG. 6).

Figure 1A:
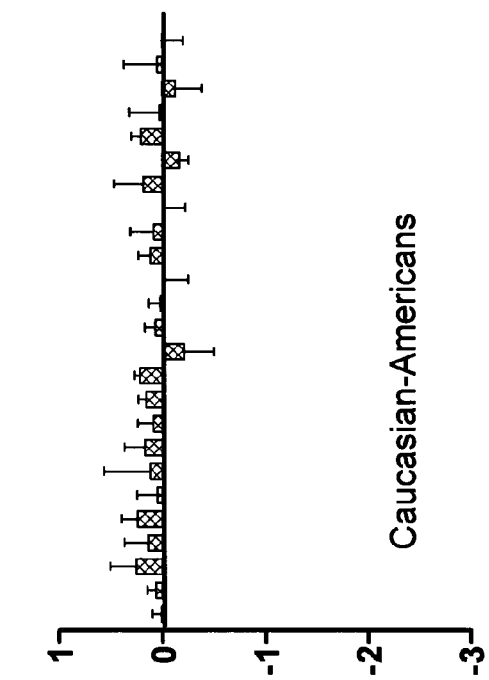
FIGS. 1a and 1b. ACE Allelic mRNA expression in left ventricular heart tissues from African-Americans (FIG. 1a) and Caucasian-Americans (FIG. 1b). Allelic mRNA expression ratios (major/minor allele for marker SNPs rs4309 (C/T), rs4343 (A/G)) are averages of results using both markers. AEI was prevalent in African-American (FIG. 1a) but not Caucasian-American (FIG. 1b) heart tissues. Genotypes for the promoter SNPs are indicated above the African-American samples. Data are mean±SD, ***P<0.001 versus pooled DNA ratios.

Standard curves performed with mixtures of DNA alleles were linear over the observed range ($r^2$=0.996-0.999). Since gDNA ratios varied within a small range (<±2SD), no variable copy number polymorphisms were detectable (although the SNaPshot method used would have missed hemizygous subjects). Therefore, the mean allelic gDNA ratios were normalized to 1. Allelic ACE mRNA expression in heart tissues varied up to four-fold compared to gDNA ratios, indicating the presence of strong cis-acting regulatory factors (see FIG. 1; using a $\log_2$ scale).

Allelic expression ratios obtained with the two marker SNPs in compound heterozygotes (n=20), indicating that the results are reproducible. Allelic mRNA ratios deviated significantly from unity in five of 33 subjects. Strikingly, each of the five tissues showing strong AEI was obtained from African-American subjects even though only eight African-Americans were heterozygous for a marker SNP. In contrast, none of the Caucasian-Americans displayed significant AEI (FIG. 1), showing a significant difference between ethnic groups.

Figure 1B:
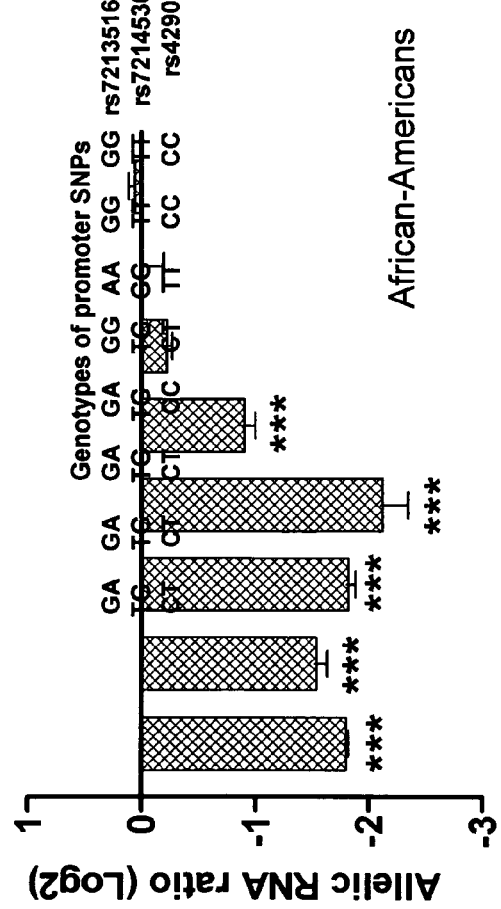

To ascertain the responsible regulatory polymorphisms, we sequenced the ACE locus in genomic DNA from the eight African-American subjects. No polymorphisms within the transcribed mRNA region (UTRs or protein-coding regions) matched the pattern of allelic expression. On the other hand, three polymorphisms (rs7213516, rs7214530, rs4290) (FIG. 11a—Table 2A) in a region 2-3 kb upstream of the ACE transcription start site were strongly associated with allelic mRNA expression imbalance in African-Americans ($P<10^{-7}$). Moreover, these three SNPs were absent in Caucasian-American cardiac tissues that also failed to show detectable AEI (FIG. 1b).

In the cardiac tissues surveyed, rs7213516, rs7214530 and rs4290 were in extensive but incomplete LD, so that we cannot exclude any of the 3 SNPs from contributing to the AEI ratios. In the HapMap data for the Yuruba population in Ibadan, Nigeria, rs4290 was in complete LD with rs7214530 (D'=1.0, $r^2$=1.0) but not with rs7213516 (D'=1.0, $r^2$=0.55) (FIG. 5).

The incomplete LD in HapMap between rs4290 and rs7213516 motivated later selection of these two markers for the clinical association study.

We next genotyped additional ACE (rs4291, rs4292, rs4357, rs4363, rs13447447, rs4366) for all samples with allelic mRNA data (FIG. 11a—Table 2A). The only additional SNP showing significant association with AEI, rs4357 ($P<10^{-7}$) located in intron 21 (FIG. 5), was in partial linkage disequilibrium (LD) with the upstream SNPs (with rs4290: D'=1.0, $r^2$=0.77; with rs7213516: D'=0.71, $r^2$=0.38). Since several subjects with AEI were homozygous for rs4357, this argues against a functional role. The commonly studied I/D variant (rs13447447) had a p-value of 0.09 for association with AEI, again owing to LD with the promoter SNPs, but it can also be ruled out as many I/D heterozygotes failed to show AEI.

Figure 2B:
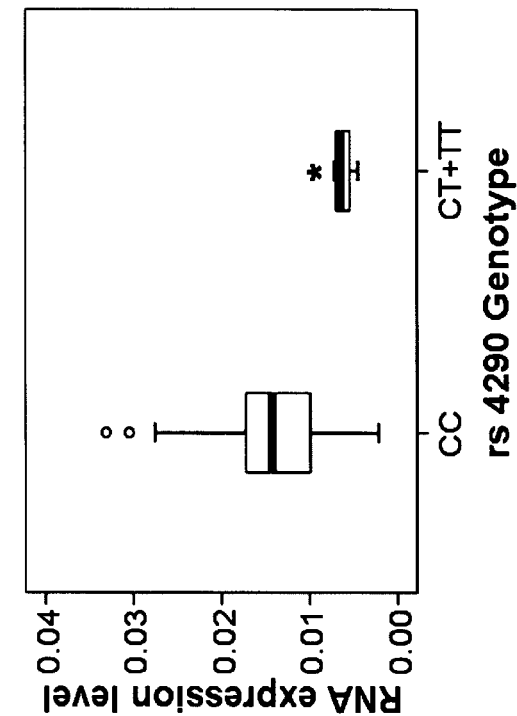
FIGS. 2a and 2b. Total mRNA expression levels of ACE in 65 heart tissues. The boxplots display the median plus or minus one quartile. Results are grouped by genotype of I/D (rs13447447) (P=0.93)(FIG. 2a) and carriers of the promoter rs4290 T allele (FIG. 2b). ACE mRNA levels are relative to β-actin. *P<0.05 versus CC genotype (t-test for mean differences).
Figure 2A:
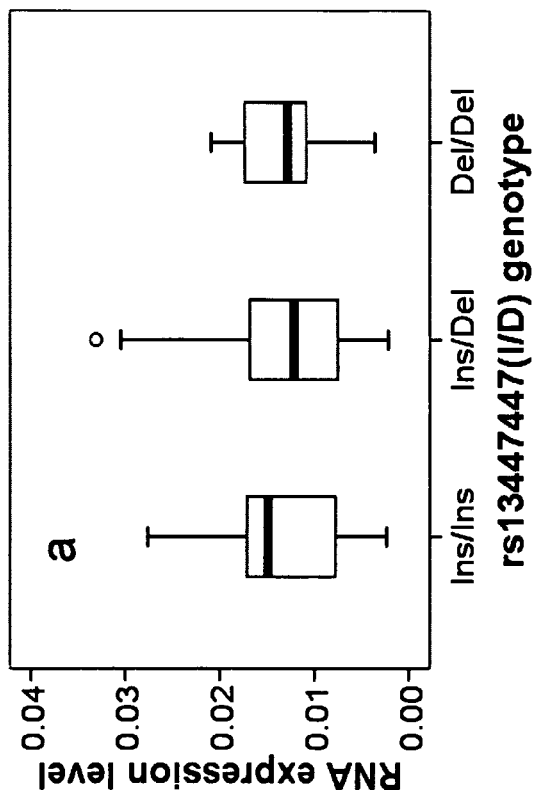

The value of allelic mRNA ratios below 1 in the five African-American subjects showing AEI indicated that the less frequent allele had reduced mRNA expression (considering the inferred phasing between the marker SNP alleles and those of the promoter SNPs). To test this further we measured overall ACE mRNA levels by RT-PCR. Whereas no association with mRNA levels was observed with the I/D variant (FIG. 2a), carrying the minor allele of the promoter SNPs was associated with decreased ACE mRNA expression (rs4290 T; P<0.02 (FIG. 2b), rs7213516 A; P<0.04). This result indicates that the minor alleles of the promoter SNPs reduce expression.

Reporter Gene Analysis of Three ACE Promoter SNPs

To determine whether the promoter SNPs, rs7213516, rs7214530, and rs4290, affect transcription, we compared activities of a 4.3 kb fragment from the ACE promoter region, containing either the reference sequence (G-T-C) or different combinations of the three SNPs, using a reporter gene assay in HEK293 and bovine aortic endothelial cells (BAEC).

Figures 3A, 3B:
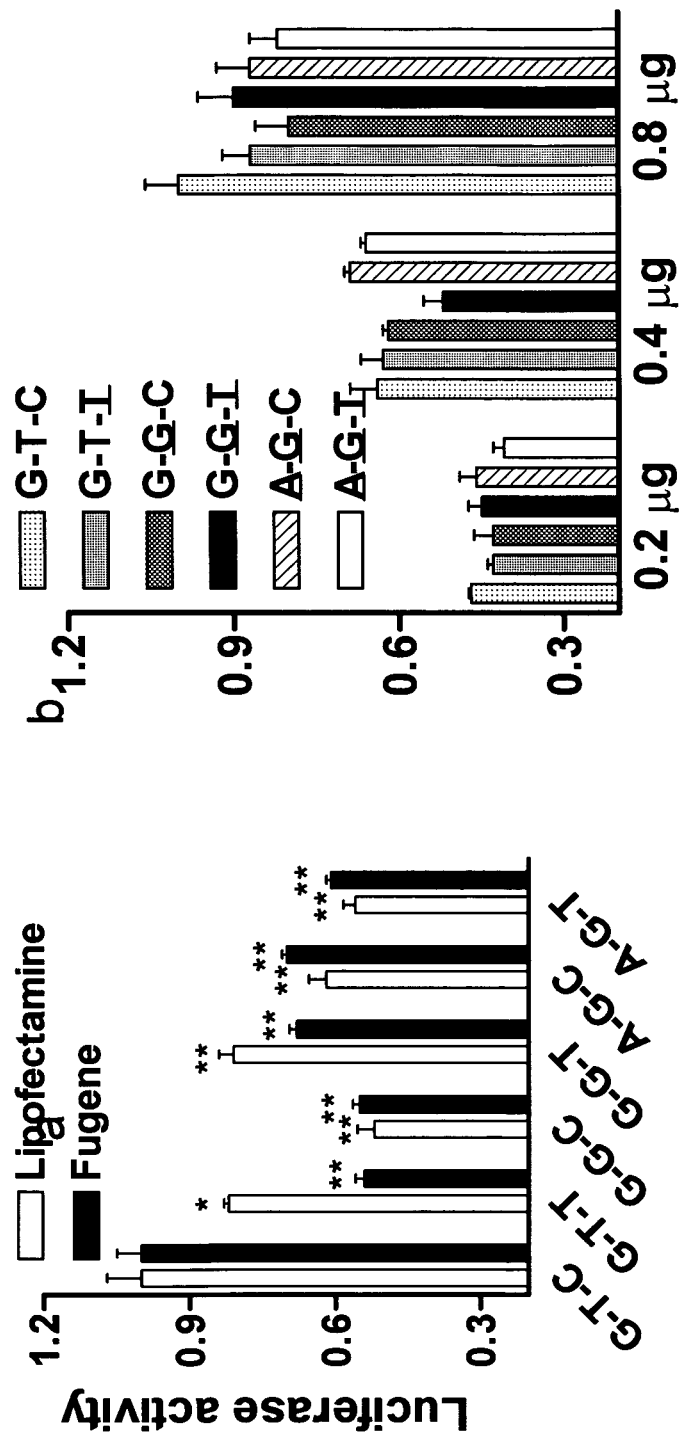
FIGS. 3a and 3b. Luciferase reporter gene assay of the ACE promoter in bovine aortic endothelial cells (BAEC) FIG. 3a) and HEK293 cells (FIG. 3b). An ACE promoter DNA fragment spanning from −4,335 to +1 was cloned into the pGL3-Basic vector, containing various combinations of the promoter SNPs rs7213516 (G/A), rs7214530 (T/G) and rs4290 (C/T).

Shown in FIG. 3a, the expression constructs containing any of the minor alleles of the three promoter SNPs significantly reduced reporter gene expression in BAEC, using two different transfection reagents. While there were differences in the degree of reduction between the various constructs, no single SNP alone could account for all results. To test for cell context-dependent effects, we also measured promoter activity in HEK293 cells. In contrast to the results with BAEC, none of the SNPs had an effect on promoter activity in HEK293 cells regardless of plasmid amounts used for transfection (FIG. 3b).

As the experiments in BAEC and HEK293 cells were done side-by-side with the same plasmid preparations, the negative results in HEK293 cells further indicate that the plasmid preparations had similar transfection efficiencies, which can be a source of error if not controlled for. Taken together with the mRNA analysis in heart tissues (FIGS. 1, 2), we conclude that each of the three promoter SNPs appears to reduce ACE gene expression, although any effects are tissue-dependent.

Genetic Association of ACE with Adverse Cardiovascular Outcomes in INVEST-GENES

We genotyped rs7213516 and rs4290 and three additional polymorphisms (FIG. 11b—Table 2B) in 258 subjects experiencing a primary outcome event (first occurrence of all cause death, nonfatal myocardial infarction (MI), or nonfatal stroke) and 774 hypertensive controls lacking primary outcome events in the genetic substudy (INVEST-GENES) of the randomized controlled clinical trial INVEST. All genotype frequencies were in Hardy-Weinberg equilibrium in all three race/ethnicity groups and displayed substantial differences between ethnic groups.

Linkage disequilibrium is shown in FIG. 7, illustrating the relationships between the genotyped SNPs. For the five polymorphisms tested in the INVEST-GENES, allele frequencies in Hispanics were intermediate between Caucasians and African-Americans. Minor allele frequencies of both rs7213516 and rs4290 differed significantly between African-Americans (16%), Hispanics (4%) and Caucasians (<1%). Genotyping quality control checks showed >99.5% concordance between different assays for the same polymorphisms.

Consistent with our finding that the rs7213516 A allele and rs4290 T allele are associated with ACE expression differences, these alleles were also robustly associated in the INVEST-GENES cohort with increased risk of a primary outcome event (FIG. 4).

The main effect was strongest in African-Americans for both SNPs, with similar trends in Hispanics and Caucasians, despite limited power in these latter groups, because of low allele frequency. In African-Americans, rs7213516 A and rs4290 T carriers had 4 times higher odds of experiencing a primary outcome event (odds ratio (OR): 4.13, 95% confidence interval (CI): 1.52-11.21 (P=0.0054), and OR 3.91, 95% CI: 1.54-9.90 (P=0.0041)), respectively.

In secondary outcomes analysis, rs7213516 conferred highest risk for nonfatal myocardial infarction, OR 6.16, 95% CI: 2.43-15.60 (P=0.0001), whereas there was no significantly higher risk for all-cause mortality (P=0.92) or nonfatal stroke (P=0.19)(FIG. 10—Table 1).

Similarly, the association with rs4290 is also largely driven by nonfatal myocardial infarction (OR 2.34); however, it only reached marginal significance.

The ACE I/D polymorphism (rs13447447) was inconsistently associated with outcomes (FIG. 4). Associations were not directionally similar in the different racial/ethnic groups, nor was there a linear trend between I/D heterozygotes and I/I homozygotes. Finally, the I/D was not associated with any of the individual components of the composite outcome (FIG. 10—Table 1). While not wishing to be bound by theory, the inventors herein now believe that there is no meaningful association with clinical outcomes analyzed here, consistent with a lack of effects on ACE mRNA level in heart tissue (FIG. 2). There was also no evidence for association of the primary outcome with polymorphisms rs4291 and rs4366.

Discussion

This study employed allelic mRNA expression analysis of ACE in human heart tissues, followed by SNP scanning, to identify regulatory polymorphisms in the ACE locus, long suspected of conferring genetic risk for cardiovascular disease. This approach revealed strong effects on ACE mRNA expression attributable to three promoter SNPs, rs7213516, rs7214530, and rs4290, located in conserved regions 2-3 kb upstream of the transcription start site. The excellent congruence between AEI ratios and clearly identifiable polymorphisms, and a significant association between genotypes and total ACE mRNA expression in human heart tissues, support the notion that these promoter SNPs reduce ACE mRNA expression. This conclusion is further buttressed by results from reporter genes assays. The three ACE promoter SNPs are common in individuals of African-American ancestry (FIGS. 11a, 11b—Tables 2A, 2B), but rare in Caucasians, and intermediate in Hispanics. Consistent with our gene expression results, a clinical association study revealed a robust genetic effect on outcomes in hypertensive patients.

Three Promoter SNPs Linked to ACE Expression

Allelic mRNA expression ratios were strongly linked with the three promoter SNPs (P=<0.0001), but because of the extensive linkage disequilibrium among them, did not permit a conclusion on which polymorphism is functional. All three SNPs reside in conserved regions.

FIG. 8 shows the promoter sequence alignments and TF binding sites. The three promoter SNPs rs7213516 (G/A), rs7214530 (T/G) and rs4290 (C/T) are located −2883, −2828 and −2306 bp upstream of the transcription start site (+1). The predicted MEF2A transcription factor binding sites based on the JASPAR database position-weight matrices are shown in detail. Sequence alignments (CLUSTALW) are based on genomic matches identified by BLAST of the human promoter region (* indicates a 1 bp insert in rhesus, dog, elephant, and armadillo sequences; † indicates a 9 bp insert in dog and armadillo sequences). Human [SEQ ID NOS 70, 34 and 278, respectively, in order of appearance], Chimp [SEQ ID NOS 71, 270 and 279, respectively, in order of appearance], Rhesus [SEQ ID NOS 72, 271 and 280, respectively, in order of appearance], Bushbaby [SEQ ID NOS 76, 272 and 281, respectively, in order of appearance], Shrew [SEQ ID NOS 73, 273 and 282, respectively, in order of appearance], Dog [SEQ ID NOS 74, 274 and 283, respectively, in order of appearance], Elephant [SEQ ID NOS 75, 275 and 284, respectively, in order of appearance], Squirrel [SEQ ID NOS 77, 276 and 285, respectively, in order of appearance], Armadillo [SEQ ID NOS 78, 277 and 286, respectively, in order of appearance].

Moreover, rs7214530 is part of a predicted recognition site for MEF2, a cardiac transcription factor previously implicated in cardiovascular disease and myocardial infarction (20-22). It is therefore possible that all three SNPs have co-evolved as part of a haplotype block prevalent in subjects of African origin, each contributing to gene regulation, possibly to different extents in different tissues. Reporter genes assays with an ACE promoter fragment, containing various combinations of the three suspected SNPs demonstrated decreased promoter activity for each combination of variant alleles, compared to the reference sequence in endothelial cells (BAEC), but not in HEK293 cells, indicating that these effects can be tissue specific. It is therefore likely that these ACE promoter polymorphisms have different effects in different target tissues, and therefore, could be associated with different pathophysiologies.

Other Polymorphisms in ACE

We found no evidence for a functional effect of the ACE I/D polymorphism in intron 15 on mRNA expression in human heart tissue, consistent with previous negative in vitro studies (4-5). Additionally, our clinical association data did not support an effect of I/D on outcomes across the various ethnic populations, despite an allele frequency and power that was substantially higher than for the promoter SNPs. Yet, countless genetic association studies are based on the I/D polymorphism even though evidence for a physiological function is lacking, and clinical associations are borderline at best (3).

Association of ACE Promoter SNPs with Clinical Outcomes

We tested several ACE polymorphisms for association with clinical outcomes in hypertensive patients with coronary artery disease (INVEST-GENES). The promoter SNPs identified in our mechanism-based screen (rs7213516 and rs4290; rs7214530 was not genotyped because of strong LD with rs4290) were highly associated with cardiovascular disease outcomes (P<0.001) (FIG. 4), and in particular, with myocardial infarction (FIG. 10—Table 1). The odds ratios ranging from 4-6 suggest an unexpectedly strong genetic effect.

We also assessed relative risk of primary outcome as a function of drug treatment, showing a strong association in individuals receiving ACE inhibitor and/or beta-blocker therapy (data not shown). However, the INVEST-GENES design was not optimal for assessing the effects of genetic factors on drug treatment outcomes. Nevertheless, this association may have a biological basis given that trandolopril and atenolol target overlapping systems of blood pressure control where ACE is a critical component. Results from the Val-HeFT trial raise the possibility that excessive neurohormonal inhibition may contribute to adverse outcomes in heart failure treatment (23). Since the promoter alleles identified here are associated with decreased ACE expression we hypothesize that they may potentiate pharmacological ACE inhibition plus beta-blockade, resulting in higher event rates via excessive neurohormonal inhibition.

Since the promoter alleles are common in African-Americans, they may partially account for phenotypic variation in ACE levels, blood pressure (e.g., 11) and response to ACE inhibitors (16-18) in individuals of African ancestry. Excessive ACE inhibition in African-Americans carrying the minor alleles of these promoter SNPs could have accounted for the increased susceptibility to angioedema as a main adverse effect of ACE inhibitors (18). While these alleles were found at lower frequency in Hispanics and Caucasians, they could be clinically relevant in the population at large, although we had limited statistical power to address this question. While not wishing to be bound by theory, the inventors herein now believe that these alleles have clinical utility as biomarkers in the selection of therapeutic options for individual patients. The use of race in guiding treatment is controversial but does play a role in clinical practice (24). Ultimately, therapy may be best optimized for individual patients with tests for functional biomarkers instead of relying on assumptions related to apparent, or self-identified, race or ethnicity (25).

Physiological roles for ACE include blood pressure regulation, kidney function, processing of kinins and other peptides, and degradation of amyloid-beta protein (26,27), suggesting the new ACE promoter alleles may be relevant in other human pathologies. Among the heart tissues from 12 African-American heart transplant patients only 8 were eligible for AEI analysis. Among the twelve samples the minor allele frequency of rs7213516 and rs4290 (25-27%) were higher than expected (16.0% in INVEST-GENES), with one patient homozygous for the minor alleles, arguing for conducting a larger study of heart failure patients.

Thus, the discovery of regulatory alleles in key genes through allelic mRNA expression analysis, followed by clinical association studies, has broad potential for leading to viable biomarkers guiding an individual's therapy (28).

MATERIALS AND METHODS

Analysis of ACE mRNA Expression in Heart Tissues

Approval for use of human subjects was obtained from the OSU IRB. Left ventricle tissue from 65 heart transplant patients was obtained through The Cooperative Human Tissue Network: Midwestern Division at OSU and stored at −80° C. until extraction. Genomic DNA and RNA were isolated, and cDNA was prepared from 1.0 ug RNA in three independent preparations, using oligo dT and gene-specific primers close to the two marker SNPs to minimize the effects of mRNA decay in post-extract tissues.

Total mRNA Expression Levels

Overall ACE mRNA expression was measured by RT-PCR for each sample. Gene expression results by genotype were analyzed with SPSS 14.

Measurement of Allelic ACE mRNA Expression

We measured allelic mRNA expression, as described previously (6-10), amplifying short regions of gDNA and cDNA around ACE exonic marker SNPs from heart tissues of heterozygous individuals (rs4309, located in exon 8, n=28; rs4343, located in exon 16, n=24). Primer extension with fluorescent dideoxynucleotides by SNaPshot (Applied Biosciences) allowed quantitation of relative amounts of each allele by capillary electrophoresis on an ABI3730 (Applied Biosciences). Corrected allelic mRNA expression ratios for individual cDNAs were calculated by normalizing to the mean ratio of gDNA peaks (SD for gDNA: rs4309±12.4%, rs4343±8.6%).

Examples for assay results are shown in FIG. 6. Each sample was assayed from three independent cDNA syntheses, each performed at least in duplicate.

Scanning the ACE Locus for Functional Polymorphisms

To link SNPs to allelic mRNA expression ratios, we genotyped SNPs selected to represent the major haplotype blocks (FIGS. 11a, 11b—Tables 2A, 2B) in all 65 heart tissues. SNPs were genotyped as described herein. In addition, we sequenced full length cDNAs and the 5'-upstream region over 3 kb in eight African-Americans detecting five SNPs in the upstream region (FIG. 11a—Table 2A).

The presence of AEI was set at allelic mRNA ratios >1.5 or <1/1.5 as cutoff. Association between genotype status (heterozygous or homozygous) with AEI was determined using HelixTree (Golden Helix, Inc.). Linkage disequilibrium between SNPs (expressed as D') and haplotypes were calculated using HelixTree (Golden Helix, Inc.).

ACE Reporter Gene Assay

A promoter fragment ranging from –4,335 to +1 (the major transcription start site) in PGL3 basic vector (Promega) was provided by Dr. Melanie Eyries (29). Various combinations of rs7213516/rs7214530/rs4290 haplotypes were obtained via site-directed mutagenesis or restriction digest of amplified genomic DNA with MscI and BstEII and subsequent cloning. All inserts were fully sequenced to verify the intended sequence. The constructs were transfected into HEK-293 and BAEC, cultured in DMEM/F12 media containing 10% fetal bovine serum, penicillin (0.10 units/ml), and streptomycin (10 µg/ml), at 37° C. with 5% $CO_2$. Twenty four hours before transfection, $1-2 \times 10^5$ cells were plated into 24-well plates and transiently transfected with FuGENE HD Transfection Reagent (Roche Applied Science) or Lipofectamine (Invitrogen) in serum free medium for 5 hours. As a control, Renilla luciferase constructs were cotransfected with PGL3 basic fused constructs at a 1:20 ratio. Cells were harvested after 48 hours and transferred to 96-well plates, and luciferase activity was detected with Dual-Glo luciferase assays (Promega) on a fluorescence plate reader (PerkinElmer). Two independent transfections and triplicate luciferase assays were performed for each construct and cell line. Results were analyzed with Prism (GraphPad).

Clinical Genetic Association Study INVEST and INVEST-GENES

The INternational VErapamil SR Trandolapril STudy (INVEST) evaluated cardiovascular adverse outcomes in patients randomized to atenolol or verapamil SR hypertension treatment strategy in 22,576 patients with documented coronary artery disease (CAD) and hypertension (19). The primary outcome was the first occurrence of death (all cause), nonfatal MI, or nonfatal stroke. These events were taken separately as secondary outcomes. In the genetic substudy (INVEST-GENES), genomic DNA was collected from 5,979 patients using buccal cells from mouthwash samples (30). All patients provided written informed consent, as approved by the UF IRB. The present case-control study focused on the 258 INVEST-GENES patients who experienced a primary outcome event during study follow-up (cases), frequency matched 3:1 to cases for age, sex, and race/ethnicity with 774 individuals who were event-free during study follow-up (controls).

The patients had a mean age of 71 years, half were female, 25% were of Hispanic ethnicity, and 13% were African-Americans. Previous analyses showed that case-control analysis in this group match findings from the entire INVEST cohort, the inclusion of which increases only the number of controls (31).

We genotyped promoter SNPs rs7213516 and rs4290, and the tagging markers (rs4291, rs13447447, rs4366) (genotyping details below), to sample major haplotype blocks. Quality control procedures included blind duplicate genotyping of 5% of samples via the same or an alternative method, assessment of Hardy-Weinberg equilibrium, and assay validation using Coriell samples previously genotyped as part of HapMap. To address potential population stratification, we genotyped 87 autosomal ancestry informative markers (AIMS) interspaced with large interlocus distances across the genome in order to give independent association with the disease and genetic background (see detailed analysis below) (32,33).

Statistical Analysis of Clinical Genetic Associations

Baseline characteristics between case and controls in INVEST-GENES were compared using t-test for continuous and Chi-squared test for categorical variables, respectively. Hardy-Weinberg equilibrium (HWE) of genotype frequencies within each race/ethnic group was tested with Chi-squared test with one degree of freedom. Because of the low minor allele frequency for rs7213516 and rs4290 in the entire INVEST cohort, we decided a priori to combine heterozygous patients with those homozygous for the variant alleles for all analyses. Logistic regression was performed to assess the association of genotypes/haplotypes with the primary and secondary outcomes after adjusting for ancestry and pre-specified confounding factors, namely age (by decades), gender, race/ethnicity, and history of MI and heart failure, and drug treatments.

Detailed Analysis

Tissue Preparation and ACE Allelic Expression Analysis

Sixty-five heart failure tissue explants from left ventricles were isolated and frozen for later research under an OSU IRB approved protocol. The demographic breakdown of these samples was as follows: Caucasian male (n=42), African-American male (n=4), Caucasian female (n=13), African-American female (n=6). DNA was prepared by a standard salting-out method from heart tissue (34). For RNA isolation, ~100 mg tissue was pulverized over dry ice and suspended in Trizol reagent, followed by phenol-chloroform extraction, and filtration through an RNAeasy column (Qiagen) after treatment with DNAse I. RNA quantity and quality was confirmed by UV spectrophotometry and nanodrop analysis (Bioanalyzer, Agilent Biotechnologies). cDNA was synthesized following the manufacturer's protocol (Superscript RTII, Invitrogen) from 1.0 ug RNA in three independent preparations using oligo dT and ACE gene-specific reverse primers to increase specific yield. Negative controls (lacking RTII) and positive expression signals for ACE were confirmed by RT-PCR on an ABI7000 cycler followed by gel electrophoresis to confirm correctly sized products. The primers used for RT-PCR verification were the outer primers for the SNaPshot assay.

Marker SNPs (rs4309, rs4343) were genotyped at the Ohio State University Pharmacogenomics Core Laboratory in 65 heart failure samples by a melting curve dissociation approach on an ABI7000 real-time PCR instrument in order to determine heterozygotes for allelic expression assays (35). Allelic expression assays in genomic DNA and cDNA for each heterozygote were carried out in triplicate, and analyzed as previously described (6-10). For the rs4343 assay, due to the SNP location near an exon border, separate DNA and cDNA forward primers were used. Outside amplification primers for the assay were as follows (see FIG. 13—Table 4):

rs4309 forward primer: TGAGATGGGCCATATACAG-TACTAC [SEQ ID NO: 1];

reverse primer: CCCGACGCAGGGAGAC [SEQ ID NO: 2], and rs4343 DNA forward primer: CCCTTACAAGCAGGT-GAGCTAA [SEQ ID NO: 3];

cDNA forward primer: ACCACCTACAGCGTGGCC [SEQ ID NO: 4];

The extension primers for ACE allelic expression assay were as follows:

for rs4309, CTGCAGTACAAGGATCTGCC [SEQ ID NO: 6];

for rs4343, GACGAATGTGATGGCCAC [SEQ ID NO: 7].

Measurement of Overall mRNA ACE Expression

Total ACE mRNA expression levels were measured in all heart tissues on two cDNA preparations by RT-PCR with cDNA specific primers that span the ACE exon 9/10 border (see FIG. 18—Table 9):

forward-primer: CCCCTTCCCGCTACAACTT [SEQ ID NO: 8];

reverse-primer: TCCCCTGATACTTGGTTCGAA [SEQ ID NO: 9].

RT-PCR was done with SYBR Green on an ABI7000 (30 cycles, 2 steps: 95° C., 60° C.); values were normalized to β-actin expression levels. The correct size products were verified by gel electrophoresis.

Generation of ACE Promoter Region Constructs for Reporter Gene Assays

An ACE upstream region construct (−4335 to the transcription start site) driving expression of a firefly Luciferase reporter gene (pGL3. Basic, Promega) was kindly provided by M. Eyries (29). Sequencing indicated this construct contained the major allele at all polymorphic sites in the region compared to the reference genome sequence, thus it was labeled (G-T-C). Site-directed mutagenesis (Stratagene) was employed to generate altered constructs with SNP combinations; for rs4290 (G-T-T) sense primer: CTCTGCACCCTTC-CTTTGATGAGGTTTTG CCCT [SEQ ID NO: 10];
antisense primer: AGGGCAAAACCTCATCAAAG-GAAGGGTGCAGAG [SEQ ID NO: 11], rs7214530 (G-G-C) sense primer: GAGCATATTTT-TAAGGGCTGGTTTTCT CTCCTGTGGTAACT [SEQ ID NO: 12];

antisense primer: AGTTACCACAGGAGAGAAAAC-CAGCCCTTAAAAATATGCTC) [SEQ ID NO: 13], and rs4290 and rs7214530 (G-G-T).

A fifth construct containing the three minor alleles for rs7213516, rs7214530 and rs4290, (A-G-T), was isolated by PCR of an individual genomic DNA (forward primer, GAGACGGAGTTTTGCTCTTGTTG [SEQ ID NO: 14];

reverse primer, CAGAGACCTGACCCACGTGAG) [SEQ ID NO: 15], restriction digest with MscI and BstEII and ligation with digested plasmid that contained the rs4290 T variant. (See FIG. 17—Table 8). All plasmid insert sequences were fully sequenced confirming the absence of additional genetic differences.

Genotyping

Genomic DNA isolation and genotyping for rs4290, rs4291 and rs7213516 in INVEST-GENES was performed at the University of Florida Center for Pharmacogenomics. Genomic DNA was isolated from buccal genetic samples using commercially available kits (PureGene, Gentra Systems Inc.) and adjusted to 20 ng/μl. Genotyping for rs4290 was performed by polymerase chain reaction (PCR) followed by pyrosequencing using a PSQ HS96A SNP reagent kit according to the manufacturer's protocol (Biotage AB) (36). SNPs rs7213516 and rs4291 were genotyped by Taqman assay. The PCR and sequencing primers used for ACE SNP rs4290 were as follows (see FIG. 15—Table 6):

forward biotinylated PCR primer, 5'-GAGTGTGGGT-CATTTCCTCTTT-3' [SEQ ID NO: 16];

reverse PCR primer, 5'-AGTTTAGCATGGTGC-CTAGCA-3' [SEQ ID NO: 17]; and reverse sequencing primer, 5'-GGGCAAAACCTCATC-3' [SEQ ID NO: 18].

The PCR conditions were as follows: 95° C. for 15 min, 40 cycles consisting of denaturation at 94° C. for 30 s, annealing at 59° C. for 30 s, and extension at 72° C. for 1 min, followed by final extension at 72° C. for 7 min. The Applied Biosystems 7900 HT SNP genotyping platform was used for the Taqman assays. The SNP genotyping probes (Applied Biosystems IDs: C__32160109__10 and C__11942507__10) were used for ACE rs7213516 G>A and rs4291 A>T, respectively. Five μL reactions in 384-well plates were prepared, and the assays were performed and analyzed according to the manufacturer's recommendations.

The 287 bp insertion/deletion polymorphism (rs13447447) was genotyped at the Ohio State University Pharmacogenomics Core Laboratory by PCR with FAM-labeled reverse primer (FAM-GTGGCCATCACAT-TCGTCAG), [SEQ ID NO: 19], and two unlabeled forward primers, one of which was insertion-specific both alleles forward primer, CCCATCCTTTCTCCCATTTCT [SEQ ID NO: 20];

insertion-specific forward primer, GACCTCGTGATC-CGCCC [SEQ ID NO: 21], and run on an ABI3730 capillary electrophoresis instrument to distinguish size products (insert peaks 191 by and 462 bp, deletion 175 bp).

The $CT_{2/3}$ repeat polymorphism (rs4366) was similarly genotyped by PCR with a FAM-labeled forward primer (FAM-TGGCTCCTGCCTGTACCAG) [SEQ ID NO: 22] and reverse primer (CCAAGGCTGTTCACCCGA) [SEQ ID NO: 23], and capillary electrophoresis. (See FIG. 17—Table 8).

The SNPs rs4291 and rs4292 were genotyped by multiplexed SNaPshot primer extension assay within one amplicon. Extension primers were:

rs4291 (TGGCTAGAAAGGGCCTCCTCTCTTT) [SEQ ID NO: 24] and rs4292 (TTCAGGCGCCGCTGAGGACT) [SEQ ID NO: 25]. (see FIG. 14—Table 4)

An intentional mismatch was introduced into the rs4292 primer at the $6^{th}$ position from the 3' terminus to interrupt the poly G strng.

FIG. 13—Table 4 presenting the oligonucleotide sequences used in genotyping and allelic expression imbalance (AEI) assays for ACE that employed primer extension technology, showing [SEQ ID NOs: 1-7, 24, 25, 32-33]. Underlined nucleotides were intentionally mismatched against the reference sequence. The original primer sequences [SEQ ID NOs: 1-7, 24, 25, 32-33] are validated assays. In addition, a multiplex assay was developed using the primers [SEQ ID NOs: 265-269].

The SNPs rs4357 and rs4363 were genotyped by a melting curve dissociation approach as previously described (2) with the following primers:

rs4363 forward primer CTGCCCCGCACCCTTG [SEQ ID NO: 26];

rs4363 reverse primer G allele CCTTCTGAGCGAGCT-GTGC [SEQ ID NO: 27];

rs4363 reverse primer A allele with GC clamp GGCGGC-CGGCCCGCCCCGCCTTCT GAGCGAGCTGCGT [SEQ ID NO: 28];

rs4357 reverse primer TGACTTGAGGGAGGGTCCCT [SEQ ID NO: 29];

rs4357 forward primer C allele GCAGGAGAATGGGGT-TCC [SEQ ID NO: 30];

rs4357 reverse primer T allele with GC clamp CGGGC-CGCCGGGCCGCGGCAG GAGAATGGGGTACT [SEQ ID NO: 31].

INVEST and INVEST-GENE Cohort

The INternational VErapamil SR Trandolapril STudy (INVEST) evaluated blood pressure and cardiovascular adverse outcomes occurring with either an atenolol or verapamil SR hypertension treatment strategy in 22,576 patients with documented coronary artery disease (CAD) and hypertension (19). Race/ethnicity was based on patient self-report and interaction with the site investigator, choosing all that were applicable among: Caucasian, African-American, Asian, Hispanic, and "other". Hispanic patients were defined as those who chose only 'Hispanic'. Patients were seen every six weeks for six months and every six months thereafter until two years after the last patient was enrolled. Addition of trandolapril and hydrochlorothiazide were allowed in both arms, and were added as needed to meet JNC VI BP goals (37,38). The primary outcome was the first occurrence of one of three secondary outcomes: death (all cause), nonfatal MI, or nonfatal stroke. All events were adjudicated by an independent committee. Clinical Trial Registration Identifier: NCT00133692 L: clinicaltrials.gov/ct/gui/showNCT00133692?order=5.

Controlling for Population Stratification in INVEST-GENES

To control for potential population stratification in our racially and ethnically diverse population, we used a panel of 87 autosomal ancestry informative markers (AIMs) that show large allele frequency differences across three parental populations (West. Africans, Indigenous Americans, and Europeans) (32). The AIMs were selected to be distributed across the genome and to be distantly interspaced to give independent association with the disease and genetic background. These 87 AIMs were genotyped using either allele-specific PCR with universal energy transfer labeled primers or competitive allele specific PCR at Prevention Genetics (Marshfield, Wis.) (33). Results from this analysis were used in the adjusted genetic association analysis.

FIG. 12 shows Table 3 presenting the baseline characteristics for the INVEST-GENES case and control patients.

FIG. 14 shows Table 5 presenting the oligonucleotide sequences employed in genotyping ACE SNPs by the GC-clamp method described in Papp et al, showing [SEQ ID NOs: 35-43].

FIG. 15 shows Table 6 presenting the oligonucleotides sequences employed in ACE Pyrosequencing genotyping, showing [SEQ ID NOs: 16-18].

FIG. 16 shows Table 7 presenting the oligonucleotide primers used in the amplification and direct sequencing of the ACE upstream gene region and cDNA, showing [SEQ ID NOs: 45-69].

FIG. 17 shows Table 8 presenting the FAM-labeled oligos and related oligos used in genotyping ACE polymorphisms, \showing [SEQ ID NOs: 15-16, 20-23, 44].

FIG. 18 shows Table 9 presenting the oligonucleotides used in the measurement of ACE expression by RT-PCR, including one that spans cDNA exons, showing [SEQ ID NOs: 8-9].

In summary, described herein are novel insights into the molecular genetics and function of the ACE1 gene, uncovered using the AEI approach described. We have characterized three SNPs that define a subpopulation of samples that exhibit differences in the mRNA expression of ACE1. We further determined that these SNPs are found in high frequency within an African-American demographic. Due to the relatively high frequency of these SNPs are believed to be useful as predictive or diagnostic biomarkers. Lower frequency biomarkers (<5%) may be less likely to reach a threshold in terms of market size that makes them economically feasible to use in clinical testing. Due to the physiological importance of ACE1 and the considerable body of literature supporting ACE1 genetic variability as an influence on medically relevant traits, there is potential for these SNPs to eventually be used as biomarkers to assess disease risks (e.g., heart failure, Alzheimer's disease) or predict adverse responses to current and future therapeutics targeting the renin-angiotensin system (e.g., ACE inhibitors, angiotensin receptor blockers (ARBs)).

EXAMPLE II

SOD2

Genetic, epigenetic, and environmental factors determine phenotypic variability, including susceptibility to disease or treatment outcome. Polymorphisms that change the amino acid sequences in coding regions (cSNPs) are readily detectable. However, regulatory polymorphisms (rSNPs) appear to be more prevalent than functional nonsynonymous cSNPs [1-5]. Genome-wide surveys and SNP association analysis with mRNA expression trait mapping [5,6] indicate regulatory polymorphisms as major factors in human phenotypic evolution and variability [5,7]. A third type of functional polymorphism affects mRNA processing (splicing, maturation, stability, transport) and translation [8]. We refer to this class of polymorphisms as 'structural RNA polymorphisms' (srSNPs). However, the overall role of rSNPs and srSNP still requires systematic evaluation.

Whereas mRNA levels are subject to both cis- and trans-acting factors, measuring the relative allelic mRNA expression selectively detects only cis-acting factors. Allelic expression imbalance (AEI), i.e., a different number or type of mRNAs generated between alleles, is a robust and quantitative phenotype directly linked to cis-acting polymorphisms [3, 5, 8-21] and epigenetic regulation, including X-inactivation, imprinting, and gene silencing [4, 22, 23].

Genome-wide association studies continue to increase the number of candidate genes, while knowledge of the functional genetic variants is lagging. AEI analysis is a powerful tool for finding regulatory polymorphisms, but technical difficulties hamper broad usage.

Earlier AEI methods mostly targeted monoallelic expression, while polymorphisms resulting in relatively small changes, although potentially physiologically relevant, are more difficult to measure. Array- and RT-PCR-based methods with limited precision or sensitivity have been applied to detect partial regulatory changes, but have mostly been applied to small sets of candidate genes in lymphocytes. Results from these studies suggest that 20-50% of genes show detectable AEI [2, 3, 24-26]. Yet, because the impact of rSNPs and srSNPs strongly depends on the tissue context, AEI analysis should be performed in physiologically relevant tissues [27,28]. Systematic and accurate surveys of AEI in many genes applied to a variety of human target tissues are lacking. Yet, autopsy tissues present additional difficulties because of partial mRNA degradation.

Also disclosed herein is a method for the rapid detection of regulatory polymorphisms in multiple genes. The method described herein is a robust and fast methodology that is especially applicable to human autopsy tissues. The method described herein fills an important gap between large-scale candidate gene discovery and resolution of the functional variants.

In the examples described herein, is a study which surveyed AEI for 42 genes in human autopsy tissues, including brain, heart, liver, intestines, and kidney, as well as peripheral mononuclear cells, revealing frequent AEI in a large fraction of genes.

In one embodiment, in cardiovascular genes where regulatory polymorphisms had been reported previously, we tested whether the observed AEI ratios were compatible with any effects of these polymorphisms on allelic expression in relevant tissues. We also addressed the question of how srSNPs affect mRNA folding, and point to a number of genes where frequent srSNPs affect mRNA expression. The results provide insight into the prevalence of rSNPs and srSNPs.

Results

Methodology for AEI Analysis of Multiple Genes in Human Autopsy Tissues

We developed a rapid methodology for measuring allelic ratios in genomic DNA and mRNA (as cDNA) (AEI analysis) in human autopsy target tissues.

The assay relies on PCR/RT-PCR amplification, followed by a primer extension step with fluorescently labeled dideoxynucleotides, and analysis by capillary electrophoresis. Details of the assays applied to single genes have been published previously by us for several genes included in the present survey [9-16].

To facilitate application to multiple genes in human autopsy tissues, the method described herein includes several steps for obtaining reproducible allelic gDNA and mRNA ratios, including use of multiple gene-specific primers to maximize cDNA yields for the target genes. Assay throughput is ~150 samples/hour, or higher with multiplexing, with an error rate in the order of 5% (gDNA) and 10-15% (mRNA).

Application of AEI Analysis to Candidate Genes

AEI analysis was applied to 42 candidate genes in a variety of human tissues (FIG. 26—Table 13), divided into genes for cardiovascular and CNS disorders, and drug metabolism and transport.

This selection provides information on the frequency of cis-acting factors but was not designed to cover the much larger number of possible candidate genes. We first determined (by RT-PCR) all 42 genes were well expressed in the target tissues examined and then determined >4,200 individual genotypes for mRNA marker SNPs in the candidate genes. The 1,008 heterozygous samples suitable for use in AEI assays yielded relative allelic expression for an average of 23 subjects or 46 individual chromosomes per gene (average marker SNP heterozygosity ~24%). Results for four genes (ACE, SOD2, NOS3, CCL2) are shown in FIG. 22.

This example was well-powered to detect frequent functional polymorphisms (>5% minor allele frequency), similar to previous AEI studies [2, 25, 26]. Details on tissue source, number of samples, marker SNPs, and allele frequency are found in FIG. 27—Table 14.

As a conservative detection threshold for the presence of mRNA AEI ratios (major:minor allele), we used ±log 2 0.5 (1:1.4 or 1.4:1) corresponding to 3 SD or more relative to DNA ratios, similar to previous studies [24,25].

FIG. 27—Table 14 contains results for genes meeting the detection threshold in at least one sample, along with information on the marker SNPs, number of replicate analyses, frequency, magnitude and direction of AEI. If a suspected functional polymorphism is in near complete linkage disequilibrium with the marker SNP, most or all AEI ratios are unidirectional (either <1 or >1), as observed with SOD2 in heart tissues (FIG. 26).

In contrast, functional polymorphisms unlinked to the marker SNP are revealed by random distribution of ratios <1 and >1 (FIG. 26, FIG. 27—Table 14), indicating these are located in other haplotype blocks. Lesser AEI ratios may also be of physiological relevance but should be subject to more extensive analytical validation to exclude artifacts. The results reveal AEI above our threshold in 67% of the candidate genes, with AEI in two or more subjects in 55% of genes. Where genes lack significant AEI this argues against the presence of cis-acting factors in the tissues analyzed.

Several well-studied genes, such as ACE and SOD2, displayed substantial AEI that was unexpected from previous genetic analyses (FIG. 27—Table 14).

In some cases, the AEI data confirm previous studies, for example, the modest AEI ratios observed for COMT [17], and a similar frequency and extent of AEI for NQO2 in white blood cells [26] and DTNBP1 in the pons region [29]. We also failed to observe significant AEI in 5HT2A, as reported [30]; however, another study suggests the presence of AEI [31] but lacks rigorous validation of the results.

It is possible that AEI may be detectable only in certain ethnogeographic populations where regulatory alleles are sufficiently frequent (see ACE below), or in specific tissues, environmental conditions, and diseases. For example, AEI was observed for VKORC1 only in the liver but was undetectable in heart tissues and B-lymphoblasts (CEPH samples) (FIG. 27—Table 14).

Relationship Between AEI and mRNA Levels

We tested whether the presence of AEI is correlated with total mRNA levels, measured by RT-PCR, in a subset of genes (SOD2, CCL2, NOS3, FLT1, HIF1A, LPL, PTGDS, and MAOA). Borderline significant correlations between AEI and mRNA levels were observed for HIF1A ($r=-0.45$, $p<0.06$) and PTGDS ($r=0.38$, $p<0.04$). These moderate correlations reflect the greater variability of overall mRNA levels compared to allelic ratios.

Cardiovascular Disease Candidate Genes

AEI analysis was applied to 18 cardiovascular candidate genes that serve as drug targets and have roles in inflammation, coagulation, lipid metabolism, vasomotor tone, and heart contractility (FIG. 26—Table 13).

Target tissues included 65 heart failure explants from transplant recipients, livers, ex vivo monocytes, and peripheral blood monocyte-derived macrophages. AEI was detectable for 15 cardiovascular genes at a 20% imbalance threshold (FIG. 26—Table 13), while 9 genes displayed AEI when we set our more stringent threshold based on the typical error rates (±log 2 0.5). AEI ratios for genes surveyed in heart tissues are shown in FIG. 27—Table 14.

Allelic mRNA expression of ACE, CCL2, SOD2, CACNA1C, and KCNMB1 was validated using a second marker SNP, with cDNA derived from a different primer (FIG. 27—Table 14).

CCL2, PTGDS, and KCNMB1 showed allelic ratios below and above 1, suggesting multiple functional polymorphisms and/or incomplete linkage disequilibrium between the marker SNPs and functional alleles (FIG. 23).

In contrast, ACE displayed large unidirectional AEI ratios only in African-Americans, suggesting the presence of a cis-acting factor enriched in this population. AEI results for ACE were confirmed with use of a second marker SNP (r2=0.98 in compound heterozygotes). Standard curves were linear, obtained with homozygous DNA representing both alleles (r2=0.99).

Both SOD2 and NOS3 showed AEI largely in a single direction—suggestive of a functional polymorphism in a shared haplotype with the marker SNP, or that the marker SNP itself is functional. The results on the frequency and extent of NOS3 AEI are consistent with published AEI results in brain tissues [27].

A number of genes did not show any AEI, for example, the L-type channel CACNA1C—a gene featuring >55 exons across ~250 kB. Subsequent use of several marker SNPs and AEI analysis of splice variants failed to reveal any cis-acting factor that could have caused highly variable splicing observed for CACNA1C in human heart [15].

Relationship Between AEI and Previously Suggested Regulatory Polymorphisms

The frequency and directionality of AEI ratios enables us to investigate whether previously proposed regulatory polymorphisms in NOS3 (rs2070744), CCL2 (rs1024611), SOD2 (rs5746091), PTGDS (rs6926), and ACE (intron 16 I/D) contribute to this phenotype.

We genotyped the proposed regulatory polymorphisms and tested for association between genotype and AEI ratios. We analyzed AEI ratios with two discrete thresholds, and also as a continuous variable.

The results in FIG. 26—Table 13 indicate that the putative regulatory polymorphisms cannot account for or are only marginally associated with AEI. For example, a proposed promoter SNP (rs1024611) [32] in CCL2 was incompatible with AEI observed in two subjects, or for the absence of AEI in many samples where this SNP is heterozygous, in both heart tissues and macrophages (FIG. 26—Table 13).

Similarly, a putative regulatory SNP, T-786C (rs2070744) upstream of NOS3, and rs6296 in PTGDS, were not significantly associated with the AEI observed in human target tissues (FIG. 26—Table 13).

A marginal association between the intensely studied ACE intron 16 I/D was detectable when AEI was analyzed as a continuous variable, but there was no association with the large AEI ratios shown in FIG. 23.

Detailed Analysis of AEI Observed for SOD2

FIG. 32 contains the mRNA sequence for the SOD2 gene [SEQ ID NO: 262]. Allelic mRNA ratios for SOD2 were ~1.5-fold in 83% of heart tissues heterozygous for marker rs4880, indicating that the 'major allele' has ~50% greater expression (however, since allele frequency is close to 50% assignment of the minor allele is arbitrary).

A second marker, rs5746092 in the 5'UTR in modest LD with rs4880, gave similar results (r2=0.73, in 16 compound heterozygotes), supporting the accuracy of the assay. FIG. 19—Table 10 shows the forward PCR primer, the reverse PCR primer and the extension primer for rs4880 and rs5746092, showing [SEQ ID NOs: 79-84].

Neither rs5746092 (37% heterozygosity) nor rs4880 (52% heterozygosity) were completely associated with AEI, as several homozygotes or heterozygotes displayed significant or no AEI, respectively.

The results suggest one or more regulatory factors within a common haplotype block. Testing a proposed functional promoter SNP, rs5746091 [33] in 10 subjects, we found that 3 homozygous carriers had no AEI and 3 heterozygous carriers did show AEI (allelic ratio >1.4), but 4 homozygous carriers displayed significant AEI, indicating that rs5746091 could not have played a sole role in allelic expression.

Because the AEI ratios are substantiated for each individual by multiple replicates, each subject showing discrepancy between AEI and SNP heterozygosity is informative and, thus fails to support a putative functional role for that SNP.

Since epigenetic factors could affect allelic expression, methylation of a CpG island close to rs4880 was measured. Distant CpG islands outside this haplotype block were not expected to preferentially affect alleles marked by rs4880. To test allele-selective methylation, we digested DNA at a Hpa II methylation-sensitive restriction site near rs4880 and measured the DNA allelic ratios, in comparison to a standard curve from mixed ratios of digested and undigested reference DNA. CpG methylation differed detectably between alleles, but allele-specific methylation did not correlate with corresponding allele-specific mRNA expression ratios (Pearson r2=0.03) (FIG. 24), arguing against an effect on allelic mRNA expression.

Effect of srSNPs on Predicted mRNA Folding Structures

To assess the potential of SNP-induced changes in mRNA folding, we estimated changes in folding energies for all possible transitions (C<>U, G<>A) and transversions (C<>G, C<>A, G<>U, A<>U) in the mRNA coding regions of the μ, κ and δ opioid receptors (OPRM1, OPRK1, OPRD1), using Mfold.

We calculated both the minimum free energy structures (MFE) and the ensembles of suboptimal structures in varying sized windows around all nucleotide positions. A majority of SNPs showed the potential to alter mRNA folding, often predicting more profound changes than the known functional A118G SNP in OPRM1 [17] (see arrow in FIG. 25).

Approximately 60% of single nucleotide substitutions affected MFE structures, and ~90% altered the ensemble of suboptimal structures, with the potential to affect mRNA functions [34].

Because SOD2 allelic expression was consistently in a single direction in such a high proportion (>80%) of samples, the inventors now believe that the SOD2 marker SNPs might have a direct, functional effect on expression. Thus, the inventors further analyzed the predicted allelic effects on mRNA folding for the marker SNPs in SOD2 (rs4880, rs5646092).

Both SNPs are in regions that display highly stable structures, with rs5646092 positioned within an 18 bp helix near the transcription and translation initiation sites. These results suggest that one or more of these alleles could affect gene expression through a change in mRNA structure.

Discussion

Robust Assay of Allelic Ratios in Genomic DNA and mRNA

Described herein is a broadly applicable methodology for rapid and robust assays of allelic gene expression (AEI) in human autopsy tissues. Measuring allelic ratios circumvents at least in part problems arising from post-mortem mRNA degradation.

The AEI analysis can be scaled up to address multiple genes at a time, and thus, represents an intermediate tool for discovering functional polymorphisms affecting gene regulation (rSNPs) and RNA processing (srSNPs) in candidate genes. The effect of rSNPs and srSNPs is expected to vary with the cellular environment, so that studies on human genes in physiologically relevant target tissues are of critical importance, for example the pontine brainstem for SERT and TPH2 mRNA [11,13].

Factors other than rSNPs and srSNPs could contribute to AEI, including variable copy number (CNV) in germline DNA or more frequently as somatic mutations in cancer [35]. We observed deviations of the DNA ratios from unity only with TPH2 in two subjects [13], indicating that gene duplications are rare among the 42 genes studied. On the other hand, complete loss of one allele in germline DNA at the marker SNP locus cannot be assessed with the SNaPshot method as presented because hemizygous carriers would appear as homozygotes, unless the gene dosage is quantitated.

Another possible source of AEI, allele-selective epigenetic regulation of gene expression must be considered where SNP scanning fails to reveal regulatory polymorphisms. The relatively high precision by which the AEI ratios can be measured, facilitated the dissection of genetic and epigenetic regulation of the X-linked MAOA, with both processes contributing to AEI [12].

Prevalence of AEI in the Candidate Genes

The method described herein permits an estimation of the prevalence of cis-acting polymorphisms in multiple (in the example herein, 42) candidate genes in human target tissues, a larger, more diverse sampling than previous studies.

FIG. 27—Table 14 provides information on the magnitude, direction, and frequency of AEI, as guides for more detailed studies. Substantial AEI (>log 2 0.5) in more than one subject was observed for 55% of the surveyed genes (FIG. 27—Table 14), similar to previous studies [2, 3, 25]; however, the frequency is higher than estimates from other studies performed with a random selection of genes in cell lines and blood cells [24,26]. These differences may be attributable to the selection of strong candidate genes, or differences in methodology, tissue specificity, number of subjects, and stringency of AEI thresholds. The presence of frequent AEI was unexpected for some of the candidate genes that had already been intensely studied for genetic polymorphisms (e.g., SOD2, ACE, TPH2 [13], DRD2 [16]).

Differential post-mortem decay for alleles could represent a confounding factor that can be overcome by molecular genetic studies of the functional polymorphisms. Polymorphisms affecting alternative splicing may not be detectable if the splice isoforms have similar turnover rates. To address this issue, allelic mRNA expression can be performed after specific amplification of each splice variant, as we have demonstrated for DRD2 (intron 5 and 6 SNPs alter formation of D2S and D2L) [16].

Scanning for Regulatory Polymorphisms Using Allelic mRNA Expression Profiles

AEI patterns provide a means of determining the location of the functional polymorphism by SNP scanning or sequencing the gene locus, followed by molecular genetic analysis of the rSNP or srSNPs, as shown for OPRM1, MDR1, MAOA, SERT, TPH2, and DRD2 [9-13,16].

Reporter gene assays in heterologous tissues are commonly used to characterize regulatory polymorphisms. If these polymorphisms are functional in vivo, one expects corresponding changes in the AEI ratios. However, for the five genes tested (FIG. 26—Table 13) we have failed to detect significant linkage between the observed AEI ratios and the putative regulatory SNPs. Similarly, our genotype scanning with AEI did not support a role for a putative SERT promoter polymorphism (SERT-LPR), although we cannot rule out that this promoter polymorphism might be active in development, or under stress [11]. Previously suggested regulatory polymorphisms in DRD2 also failed to correlate with AEI ratios [16]. A separate study of 4 genes (MAOA, NOS3, PDYN, NPY) using AEI analysis again yielded results incompatible with reporter gene assays [27], corroborating our results for MAOA and NOS3. Similarly, the AEI observed with CCL2 (MCP1) was not associated with the putative promoter SNP rs1024611 [32]. Therefore, reporter gene assays are not always reliable indicators of regulatory polymorphisms. Combined use of AEI analysis and reporter gene assays can yield more definitive results regarding regulatory polymorphisms [16].

Relevance of Structural RNA SNPs (srSNPs)

For OPRM1, MDR1, TPH2, and DRD2, we have linked the AEI ratios to SNPs in the transcribed region of the gene, likely involved in mRNA processing, turnover, and splicing [9, 10, 13, 16]. srSNPs have been shown to affect mRNA stability [9,36] and alternative splicing [16,37]. Our AEI analysis of marker SNPs in SOD2 and NQO2 indicates they (or SNPs in tight LD with them) may also affect RNA structures. Taken together, these results support the notion that srSNPs can be at least as prevalent as rSNPs.

srSNPs could alter mRNA function through changed folding dynamics [15, 16, 34]. Using Mfold to predict mRNA structural changes resulting from systematic nucleotide exchanges in opioid receptor mRNAs (FIG. 25), we find that most SNPs affect the likely ensemble of structural conformations. Consistent with this, SNPs can be detected by a physical method based on 'single-strand conformational polymorphisms', with a 95% discovery rate.

srSNPs can further affect translation, as suggested for the OPRM1 SNP A118G [16], and COMT haplotypes with altered mRNA folding [38]. Measuring AEI ratios at the protein level with use of nonsynonymous marker SNPs can allow for the determination of quantitative effects of polymorphisms on translation and protein turnover.

Cardiovascular Disease Candidate Genes

Half of the 18 cardiovascular genes studied displayed AEI at a conservative cutoff, with ACE and SOD2 conspicuous examples. An intron 16 I/D polymorphism of ACE had been extensively tested in clinical association studies, but its functional role remained unclear [39]. Our results suggest strong cis-acting factors unrelated to the I/D variant in heart tissues, with high frequency in African-Americans.

SOD2 (mitochondrial manganese superoxide dismutase) is a key factor involved in metabolizing superoxide molecules and may have a role in failing human hearts [40]. Previous association studies of two variants in SOD2 with cardiomyopathy [41,42], cancers (e.g., [43], and other disorders have yielded inconsistent results. The nonsynonymous marker SNP used here lies in a leader sequence (rs4880, −9A>V) and was suggested to affect mitochondrial uptake of the mature protein [41], while a promoter region SNP (rs5746091) disrupts binding of AP-2[33].

Common AEI observed here in failed heart tissues (FIG. 23), with allelic mRNA ratios consistently >1, indicates presence of a frequent functional variant(s) in a haplotype block containing the marker SNPs. Limited genotype scanning of the SOD2 locus indicated that the two marker SNPs (rs4880, rs5746092) each taken alone cannot account for the observed AEI, but may interact with each other or merely represent tags for a functional srSNP in this region.

The promoter SNP rs5746091 did not appear to play a main role. Previous studies have implicated structural elements in SOD2 expression, including a GC-rich 5' region upstream of the transcription start site that also extends into the 5' end of the transcript [44] and regions in the 3'UTR of the mRNA [45]. Highly favorable RNA structures exist in the region of rs5746092 and rs4880 suggesting multiple structural states in SOD2 mRNA could affect functions. Alternatively, epigenetic regulation of SOD2 expression by CpG methylation [46] could have contributed to AEI, but our initial results argue against this possibility.

The measured AEI ratios clearly demonstrate functional variation of SOD2 mRNA expression.

FLT1, HIF1A, HMOX1, and LPL did not display common and large AEI. However, because the studied candidate genes all have important physiological roles, even relatively small AEI ratios, as observed for CCL2, NOS3, FLT1, HIF1A, HMOX1, HMGCR, and LPL, may be of clinical importance [35]. Even a small activity change of a critical gene such as HMGCR could affect cholesterol production over an individual's lifetime. Moreover, pravastatin response was associated with two intronic SNPs in HMGCR, with frequency >5% in the population [47], and a genome-wide association study for LDL cholesterol also revealed an association with an intronic HMGCR SNP [48].

Thus, as described herein, the inventors have applied mRNA AEI analysis to the detection of cis-acting variation for many candidate genes, revealing many instances of yet unrecognized functional polymorphisms or other cis-acting factors. The AEI methodology can be applied on a fairly large scale while maintaining high accuracy.

Materials and Methods

Human Tissue Selection and Sources

We obtained autopsy or biopsy tissue samples from liver, kidney, intestines, peripheral white blood cells, and various brain regions (prefrontal cortex, hippocampus, ventral tegmental area (VTA), amygdala, and nucleus accumbens, and pontine nuclei of the brain stem (for SERT and TPH2)). Specimens from up to ~100 subjects for each cell or tissue were obtained from various sources and tissue banks (OSU tissue procurement division, NIH Cooperative Human Tissue Network, 105 brain sections from the Stanley Foundation, Red Cross blood samples, and tissue banks at the University of Maryland and the National Disease Research Interchange). Left ventricular pieces were collected from the failed hearts of transplant recipients under an IRB-approved protocol at The Ohio State University. Ninety EBV-transformed B-lymphoblast cell lines were obtained from the Coriell cell repository, consisting of 30 Caucasian family trios. A majority of the tissues are from normal subjects, while some tissues included subjects diagnosed with schizophrenia, bipolar disorder, Alzheimer's disease, and cancer. Ethnic distributions varied between tissues repositories; no attempt was made to cover ethnic groups evenly. The objective of this study was to detect functional polymorphisms with allele frequencies of 5% or more.

Sample Preparation

Genomic DNA and RNA were prepared from peripheral lymphocytes, or B-lymphocyte pellets, and frozen tissue samples (brain, liver, etc) as described previously [9-16]. Monocytes and monocyte-derived macrophages were cultured as described [49]. For whole blood extractions, the buffy coat was harvested, then red cells were either lysed using ammonium chloride to yield a leukocyte pellet for RNA extraction, or red and white cells were lysed with a sucrose Triton solution, providing a nuclear pellet for DNA purification. Frozen tissue samples were pulverized under liquid nitrogen and portioned into aliquots for DNA and RNA extractions. DNA was prepared by digestion of the pellet or frozen powder with SDS and proteinase K followed by NaCl salting out of proteins. DNA was recovered by ethanol precipitation, and RNA was extracted in Trizol™, chloroform extracted, and recovered by precipitation with isopropanol. RNA precipitates were dissolved in RNase-free water or Qiagen buffer, and then extracted using Qiagen RNeasy columns.

Analysis of Allelic mRNA Expression Ratios for Detection of Allelic Expression Imbalance (AEI)

Assay Design

Allelic ratios of genomic DNA and mRNA were measured with SNaPshot as reported [9-16]. Briefly, DNA or mRNA (after conversion to cDNA) regions containing a marker SNP (FIG. 29—Table 16) were PCR amplified, followed by SNaPshot primer extension analysis of each allele (FIG. 29—Table 16).

The procedure differs from earlier studies (e.g., [2]) by combining multiple gene-specific primers close to the marker SNP region for cDNA synthesis to compensate for mRNA degradation. Accurate AEI analysis requires robust expression (RT-PCR cycle threshold 27 or less). Selection criteria for a marker SNP were as follows: 1) location in the transcribed region, coding or non-coding, 2) high minor allele frequency (0.15-0.50), 3) position of marker SNPs preferably more than 20 bp from exon boundaries so that the same set of primers for PCR amplification can be used in both DNA and RNA.

Complementary DNA Synthesis cDNA was generated from total RNA (1 ug) by Superscript II reverse transcriptase (Invitrogen). Because oligo-dT priming often fails in autopsy tissues, we used both oligo-dT and gene-specific oligonucleotide primers targeting a region immediately 3' of the marker SNP (same oligonucleotide used for PCR). We have multiplexed up to 30 primers to permit 30 different AEI assays per cDNA preparation. Comparisons between single and multiple primers showed no significant differences where tested. cDNA was successfully extracted from autopsy tissues to yield reproducible results between independent cDNA preparations [9-16].

Quantitative PCR-Based mRNA Analysis

We determined the mRNA levels for each candidate gene in each tissue or cell line, using RT-PCR, to assure that expression is sufficient for accurate AEI analysis (cycle thresholds equal to or below 27 cycles). Primers used for RT-PCR were the same as those selected for the AEI analysis, with PCR conditions optimized for each primer pair on an ABI7000 cycler with SYBR-Green. Results were normalized to an internal standard ($\beta$-actin or GAPDH).

Computational Analysis of mRNA Folding

We used Mfold version 3.0 to estimate the effect of SNPs on mRNA folding [50]. Wild-type Refseq mRNA sequences of OPRM1, OPRD1 and OPRK1 were obtained without untranslated regions. A custom Unix program created every possible variant at each base position and fed sequences to Mfold for structure prediction, and subsequent automated analysis. Changes in minimum free energy, as well as pairwise comparisons in structural interactions (paired vs. unpaired) were calculated relative to the wild-type structure using sliding windows around the induced variants, and across the complete mRNA structure.

EXAMPLE III

SLC6A3

Polymorphisms in Genes Affecting Biogenic Amines as Biomarkers in CNS Disorders

SLC6A3 (encoding the dopamine transporter) (newly added gene) is associated with multiple mental disorders such as drug abuse, attention deficit disorder (ADHD/ADD), Parkinson disease, Tourette syndrome and Schizophrenia. FIG. 33 contains the mRNA sequence for the SLC6A3 gene [SEQ ID NO: 263]. Stimulant medications, such as those used to treat ADHD, and drugs of abuse such as amphetamine bind to SLC6A3 and inhibit reuptake of dopamine. Genetic variants of SLC6A3 may influence levels of gene expression and/or ability of drugs to bind to SLC6A3 protein.

Described herein is the determination that a synonymous SNP in Exon (rs6347) is associated with higher mRNA expression in both brain tissue and in a heterologous cell culture system. This is the first functional SNP occurring at high frequency in this key gene.

Polymorphisms in SLC6A3 are now believed by the inventors herein to be useful as biomarkers in numerous diseases and treatment outcomes including but not restricted to mental disorders and specifically drug addiction.

Role of SLC6A3 in Mental Disorders

Dopamine transporter is associated with multiple mental disorders such as drug abuse, attention deficit disorder (ADHD/ADD), Parkinson disease, Tourette syndrome and Schizophrenia (for review: see Bannon, 2005 and Sotnikova et al, 2006). Stimulant medications, such as those used to treat ADHD, and drugs of abuse such as amphetamine bind to SLC6A3 and inhibit reuptake of dopamine. Genetic variants of SLC6A3 may influence levels of gene expression and/or ability of drugs to bind to SLC6A3 protein. One SNP (rs27072) has been found to be significantly associated with inattention and hyperactivity/impulsivity in children with ADHD.

Polymorphisms Linked to AEI:

SLC6A3: SNP rs27072 located in the 3'UTR is associated with AEI in brain tissue. An additional synonymous SNP in Exon 9 rs6347 (not linked to rs27072) is associated with AEI in both brain tissue and cell culture. See FIG. 20 Table 11 which shows the sequences for rs27072 and rs6347, showing [SEQ ID NOs: 85-85].

FIG. 30—Table 17 shows the forward primer, the reverse primer and the extension primer for rs6437 [SEQ ID NOs: 87-89].

The rs6347 biomarker is based on molecular genetics and function. Also the frequency and penetrance are measurable by AEI. In addition, the combined use of two frequent functional polymorphisms can be used to assess disease risk and response to therapy (e.g., SSRIs).

EXAMPLE IV

CYP2C9

CYP2C9 (encoding cytochrome P450 2C9) is a liver drug metabolizing enzyme, involved in metabolism of ~20% of pharmaceuticals. FIG. 34 contains the mRNA sequence for the CYP2C9 gene [SEQ ID NO: 264].

The most common functional SNPs are CYP2C9*2 (430 C>T) and *3 (1075 A>C). These are non-synonymous SNPs with reduced enzyme activity (*2 50% and *3 25% of wild-type allele).

Described herein is a novel functional SNP, 1425 A>T, which is associated with 20-50% increased in mRNA level in human liver tissues, suggesting a "gain of function". The frequency of SNP 1425 A>T is ~4% but may vary significantly in different populations. Because it represents a gain of function (dominant effect), a 4% frequency is pharmacologically relevant. SNP 1425 A>T is in partial linkage disequilibrium with *3 (and hence may affect 8# activity), but is never to link to *2 in >liver tissues.

Polymorphisms in CYP2C9 can be useful as biomarkers in optimizing drug treatment for personalized medicine. It is noted that CYP2C9*2 and *3 already comprise a drug biomarker test, FDA approved and commercialized. See FIG. 21 Table 12 which shows the sequence for sr1057911 [SEQ ID NO: 90].

FIG. 30—Table 17 shows the forward primer, the reverse primer and the extension primer for rs9332242 and rs2017319 [SEQ ID NOs: 91-96].

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

The citation of any reference herein is not an admission that such reference is available as prior art to the instant invention. Any publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES FOR EXAMPLE I

1. Cambien F et al. (1988) Familial resemblance of plasma angiotensin-converting enzyme level: the Nancy study. *Am J Hum Genet.* 43:774-780.
2. Arnett D K et al. (2005) Pharmacogenetic association of the angiotensin-converting enzyme insertion/deletion polymorphism on blood pressure and cardiovascular risk in relation to antihypertensive treatment: the Genetics of Hypertension-Associated Treatment (GenHAT) study. *Circulation* 111:3374-3383.
3. Sayed-Tabatabaei F A, Oostra B A, Isaacs A, van Duijn C M, Witteman J C M (2006) ACE polymorphism. *Circ Res* 98:1123-1133.
4. Rosatto N, Pontremoli R, de Ferrari G, Ravazzolo R (1999) Intron 16 insertion of the angiotensin converting enzyme gene and transcriptional regulation. *Nephrol Dial Transplant* 14:868-871.
5. Lei H, Day I N M, Vorechocsky I (2005) Exonization of AluYa5 in the human ACE gene requires mutations in both 3' and 5' splice sites and is facilitated by a conserved splicing enhancer. *Nucl Acids Res* 33:3897-3906.
6. Wang D et al. (2005) Multidrug resistance polypeptide 1 (MDR1, ABCB1) variant 3435C>T affects mRNA stability. *Pharmacogen Gen* 15:693-704.
7. Zhang Y, Wang D, Johnson A D, Papp A C, Sadee W (2005) Allelic expression imbalance of human mu opioid receptor (OPRM1) caused by variant A118G. *J Biol Chem* 280: 32618-32624.
8. Lim J E, Pinsonneault J, Sadee W, Saffen D (2007) Tryptophan hydroxylase 2 (TPH2) haplotypes predict levels of TPH2 mRNA expression in human pons. *Mol Psychiatry* 12:491-501.
9. Pinsonneault J K, Papp A C, Sadee W (2006) Allelic mRNA expression of X-linked monoamine oxidase A (MAOA) in human brain: Dissection of epigenetic and genetic factors. *Hum Mol Genet.* 15:2636-2649.

10. Zhang Y et al. (2007) Novel polymorphisms in the human dopamine D2 receptor gene affect gene expression, splicing, and neuronal activity. *PNAS* in press.
11. Zhu X et al. (2001) Linkage and association analysis of angiotensin I-converting enzyme (ACE)-gene polymorphisms with ACE concentration and blood pressure. *Am J Hum Genet.* 68:1139-1148.
12. Bouzekri N et al. (2004) Angiotensin I-converting enzyme polymorphisms, ACE level and blood pressure among Nigerians, Jamaicans and African-Americans. *Eur J Hum Gen* 12:460-468.
13. Rieder M J, Taylor S L, Clark A G, Nickerson D A (1999) Sequence variation in the human angiotensin converting enzyme. *Nat Gen* 22:59-62.
14. Hajjar I, Kotchen T A (2003) Trends in prevalence, awareness, treatment, and control of hypertension in the United States, 1998-2000. *JAMA* 290:199-206.
15. Rosamond W et al. (2007) Heart disease and stroke statistics—2007 update: a report from the American Heart Association statistics committee and stroke statistics subcommittee. *Circulation* 115:e69-e171.
16. Exner D V, Dries D L, Domanski M J, Cohn J N (2001) Lesser response to angiotensin-converting-enzyme inhibitor therapy in black as compared with white patients with left ventricular dysfunction. *N Engl J Med* 344:1351-1357.
17. Sehgal A R (2004) Overlap between whites and blacks in response to antihypertensive drugs. *Hypertension* 43:566-572.
18. McDowell S E, Coleman J J, Ferner R E (2006) Systematic review and meta-analysis of ethnic differences in risks of adverse reactions to drugs used in cardiovascular medicine. *Br Med J* 332:1177-1181.
19. Pepine C J et al. (2003) A calcium antagonist versus a non-calcium antagonist hypertension treatment strategy for patients with coronary heart disease—The International Verapamil-Trandolopril Study (INVEST): a randomized control trial. *JAMA* 290:2805-2816.
20. Naya F J et al. (2002) Mitochrondrial deficiency and cardiac sudden death in mice lacking the MEF2A transcription factor. *Nat Med* 8(11):1303-1309.
21. Wang L, Fan C, Topol S E, Topol E J, Wang Q (2003) Mutation of MEF2A in an inherited disorder with features of coronary artery disease. *Science* 302(5650):1578-1581.
22. van Oort R J et al. (2006) MEF2 activates a genetic program promoting chamber dilation and contractile dysfunction in calcineurin-induced heart failure. *Circulation* 114(4):298-308.
23. Cohn J N, Tognoni G for the Valsartan Heart Failure Trial Investigators (2001) A randomized trial of the angiotensin-receptor blocker valsartan in chronic heart failure. *N Engl J Med* 345:1667-1675.
24. Taylor A L et al. (2004) Combination of isosorbide dinitrate and hydralazine in blacks with heart failure. *N Engl J Med* 351:2049-2057. [Erratum, *N Engl J Med* (2005) 352: 1276-b].
25. Bamshed M (2005) Genetic influences on health. Does race matter? *JAMA* 294:937-946. [Erratum, *JAMA* (2005) 294:1620].
26. Hemming M L, Selkoe D J (2005) Amyloid beta-protein is degraded by cellular angiotensin-converting enzyme (ACE) and elevated by an ACE inhibitor. *J Biol Chem* 280(45):37644-37650.
27. Meng Y et al. (2006) Association of polymorphisms in the angiotensin-converting enzyme gene with Alzheimer disease in an Israeli Arab community. *Am J Hum Gen* 78:871-877.
28. Johnson A D, Wang D, Sadee W (2005) Polymorphisms affecting gene regulation and mRNA processing: broad implications for pharmacogenetics. *Pharm Ther* 106:19-38.
29. Eyries M, Agrapart M, Alonso A, Soubrier F (2002) Phorbol ester induction of angiotensin-converting enzyme transcription is mediated by Egr-1 and AP-1 in human endothelial cells via ERK1/2 pathway. *Circ Res* 91:899-906.
30. Andrisin T E, Humma L M, Johnson J A (2002) Collection of genomic DNA by the noninvasive mouthwash method for use in pharmacogenetic studies. *Pharmacotherapy* 22:954-960.
31. Beitelshees A L et al. (2007) KCNMB1 genotype influences response to verapamil and adverse outcomes in the INternational VErapamil SR/Trandolapril STudy (INVEST). *Pharmacogen Gen* 17:719-729.
32. Shriver M D et al. (2005) Large-scale SNP analysis reveals clustered and continuous patterns of human genetic variation. *Hum Genomics* 2(2):81-89.
33. Myakishev M V, Khripin Y, Hu S, Hamer D H (2001) High-throughput SNP genotyping by allele-specific PCR with universal energy-transfer-labeled primers. *Genome Res* 11(1):163-169.
34. Miller S A, Dykes D D, Polesky H F (1988) A simple salting out procedure for extracting DNA from human nucleated cells. *Nucl Acids Res* 16:1215.
35. Papp A C, Pinsonneault J K, Cooke G, Sadee W (2003) Single nucleotide polymorphism genotyping using allele-specific PCR and fluorescence melting curves. *Biotechniques* 34(5):1068-1072.
36. Langaee T, Ronaghi M. (2005) Genetic variation analyses by Pyrosequencing. *Mutat Res* 573(1-2):96-102.
37. Beitelshees A L et al. (2005) Variable blood pressure response to verapamil by KCNMB1 genotype. *Clin Pharmacol Ther* 77:P97.
38. The sixth report of the Joint National Committee on prevention, detection, evaluation, and treatment of high blood pressure. (1997) *Arch Intern Med* 157:2413-2446.
39. Lehmann, D. J., Cortina-Borja, M., Warden, D. R., Smith, A. D., Sleegers, K., et al. (2005). Large meta-analysis establishes the ACE insertion-deletion polymorphism as a marker of Alzheimer's disease. *Am J Epidem* 162(4), 305-317.
40. Okabe, T., Fujisawa, M., Yotsumoto, H., Takaku, F., Lanzillo, J. J., et al. (1985). Familial elevation of serum angiotensin converting enzyme: *Q J Med* 55(216), 55-61.
41. Morimoto, T., Gandhi, T. K., Fiskio, J. M., Seger, A. C., So, J. W., et al. (2004). An evaluation of risk factors for adverse drug events associated with angiotensin-converting enzyme inhibitors. *J Eval Clin Pract* 10(4), 499-509.
42. Brown, N. J., Ray, W. A., Snowden, M. and Griffin, M. R. (1996). Black Americans have an increased rate of angiotensin converting enzyme inhibitor-associated angioedema. *Clin Pharmacol Ther* 60(1), 8-13.
43. Brown, N. J., Snowden, M. and Griffin, M. R. (1997). Recurrent angiotensin-converting enzyme inhibitor—associated angioedema. *Jama* 278(3), 232-3.
44. Kostis, J. B., Kim, H. J., Rusnak, J., Casale, T., Kaplan, A., et al. (2005). Incidence and characteristics of angioedema associated with enalapril. *Arch Intern Med* 165(14), 1637-42.
45. Morimoto, T., Gandhi, T. K., Fiskio, J. M., Seger, A. C., So, J. W., et al. (2004). An evaluation of risk factors for adverse drug events associated with angiotensin-converting enzyme inhibitors. *J Eval Clin Pract* 10(4), 499-509.

REFERENCE FOR EXAMPLES II-IV

1. Rockman, M. V. and Wray, G. A. (2002) Abundant raw material for cis-regulatory evolution in humans. Mol Biol Evol, 19, 1991-2004.
2. Bray, N. J., Buckland, P. R., Owen, M. J. and O'Donovan, M. C. (2003) Cis-acting variation in the expression of a high proportion of genes in human brain. Hum Genet, 113, 149-53.
3. Yan, H., Yuan, W., Velculescu, V. E., Vogelstein, B. and Kinzler, K. W. (2002) Allelic variation in human gene expression. Science, 297, 1143.
4. Yan, H. and Zhou, W. (2004) Allelic variations in gene expression. Curr Opin Oncol, 16, 39-43.
5. Pastinen, T., Ge, B. and Hudson, T. J. (2006) Influence of human genome polymorphism on gene expression. *Hum Mol Genet*, 15 Spec No 1, R9-16.
6. Cheung, V. G., Conlin, L. K., Weber, T. M., Arcaro, M., Jen, K. Y., Morley, M. and Spielman, R. S. (2003) Natural variation in human gene expression assessed in lymphoblastoid cells. Nat Genet, 33, 422-5.
7. Rockman, M. V., Hahn, M. W., Soranzo, N., Zimprich, F., Goldstein, D. B. and Wray, G. A. (2005) Ancient and recent positive selection transformed opioid cis-regulation in humans. PLoS Biol, 3, e387.
8. Johnson, A. D., Wang, D. and Sadee, W. (2005) Polymorphisms affecting gene regulation and mRNA processing: broad implications for pharmacogenetics. Pharmacol Ther, 106, 19-38.
9. Wang, D., Johnson, A. D., Papp, A. C., Kroetz, D. L. and Sadee, W. (2005) Multidrug resistance polypeptide 1 (MDR1, ABCB1) variant 3435C>T affects mRNA stability. Pharmacogenet Genomics, 15, 693-704.
10. Zhang, Y., Wang, D., Johnson, A. D., Papp, A. C. and Sadee, W. (2005) Allelic expression imbalance of human mu opioid receptor (OPRM1) caused by variant A118G. J Biol Chem, 280, 32618-24.
11. Lim, J. E., Papp, A., Pinsonneault, J., Sadee, W. and Saffen, D. (2006) Allelic expression of serotonin transporter (SERT) mRNA in human pons: lack of correlation with the polymorphism SERTLPR. Mol Psychiatry, 11, 649-62.
12. Pinsonneault, J. K., Papp, A. C. and Sadee, W. (2006) Allelic mRNA expression of X-linked monoamine oxidase a (MAOA) in human brain: dissection of epigenetic and genetic factors. Hum Mol Genet, 15, 2636-49.
13. Lim, J. E., Pinsonneault, J., Sadee, W. and Saffen, D. (2007) Tryptophan hydroxylase 2 (TPH2) haplotypes predict levels of TPH2 mRNA expression in human pons. Mol Psychiatry, 12, 491501.
14. Pinsonneault, J., Nielsen, C. U. and Sadee, W. (2004) Genetic Variants of the Human H+/Dipeptide Transporter PEPT2: Analysis of Haplotype Functions. J Pharmacol Exp Ther, 311, 1088-96.
15. Wang, D., Papp, A. C., Binkley, P. F., Johnson, J. A. and Sadee, W. (2006) Highly variable mRNA expression and splicing of L-type voltage-dependent calcium channel alpha subunit 1C in human heart tissues. Pharmacogenet Genomics, 16, 735-45.
16. Zhang, Y., Bertolino, A., Fazio, L., Blasi, G., Rampino, A., Romano, R., Lee, M. L. T., Xiao, T., Papp, A., Wang, D. et al. (2007) Novel polymorphisms in the human dopamine D2 receptor gene affect gene expression, splicing, and neuronal activity. PNAS, 104, 20552-57.
17. Bray, N. J., Buckland, P. R., Williams, N. M., Williams, H. J., Norton, N., Owen, M. J. and O'Donovan, M. C. (2003) A haplotype implicated in schizophrenia susceptibility is associated with reduced COMT expression in human brain. Am J Hum Genet, 73, 152-61.
18. Knight, J. C., Keating, B. J., Rockett, K. A. and Kwiatkowski, D. P. (2003) In vivo characterization of regulatory polymorphisms by allele-specific quantification of RNA polymerase loading. Nat Genet, 33, 469-75.
19. Ge, B., Gurd, S., Gaudin, T., Dore, C., Lepage, P., Harmsen, E., Hudson, T. J. and Pastinen, T. (2005) Survey of allelic expression using EST mining. Genome Res, 15, 1584-91.
20. Lin, W., Yang, H. H. and Lee, M. P. (2005) Allelic variation in gene expression identified through computational analysis of the dbEST database. Genomics, 86, 518-27.
21. Cowles, C. R., Hirschhorn, J. N., Altshuler, D. and Lander, E. S. (2002) Detection of regulatory variation in mouse genes. Nat Genet, 32, 432-7.
22. Liu, J., Chen, M., Deng, C., Bourchis, D., Nealon, J. G., Erlichman, B., Bestor, T. H. and Weinstein, L. S. (2005) Identification of the control region for tissue-specific imprinting of the stimulatory G protein alpha-subunit. Proc Natl Acad Sci USA, 102, 5513-8.
23. Singer-Sam, J., Chapman, V., LeBon, J. M. and Riggs, A. D. (1992) Parental imprinting studied by allele-specific primer extension after PCR: paternal X chromosome-linked genes are transcribed prior to preferential paternal X chromosome inactivation. Proc Natl Acad Sci USA, 89, 10469-73.
24. Pastinen, T., Sladek, R., Gurd, S., Sammak, A., Ge, B., Lepage, P., Layergne, K., Villeneuve, A., Gaudin, T., Brandstrom, H. et al. (2004) A survey of genetic and epigenetic variation affecting human gene expression. Physiol Genomics, 16, 184-93.
25. He, H., Olesnanik, K., Nagy, R., Liyanarachchi, S., Prasad, M. L., Stratakis, C. A., Kloos, R. T. and de la Chapelle, A. (2005) Allelic variation in gene expression in thyroid tissue. Thyroid, 15, 660-7.
26. Pant, P. V., Tao, H., Beilharz, E. J., Ballinger, D. G., Cox, D. R. and Frazer, K. A. (2006) Analysis of allelic differential expression in human white blood cells. Genome Res, 16, 331-9.
27. Cirulli, E. T. and Goldstein, D. B. (2007) In vitro assays fail to predict in vivo effects of regulatory polymorphisms. Hum Mol Genet, 16, 1931-9.
28. Wilkins, J. M., Southam, L., Price, A. J., Mustafa, Z., Carr, A. and Loughlin, J. (2007) Extreme context specificity in differential allelic expression. Hum Mol Genet, 16, 537-46.
29. Bray, N. J., Preece, A., Williams, N. M., Moskvina, V., Buckland, P. R., Owen, M. J. and O'Donovan, M. C. (2005) Haplotypes at the dystrobrevin binding protein 1 (DTNBP1) gene locus mediates risk for schizophrenia through reduced DTNBP1 expression. Hum Mol Genet, 14, 1947-54.
30. Bray, N. J., Buckland, P. R., Hall, H., Owen, M. J. and O'Donovan, M. C. (2004) The serotonin-2A receptor gene locus does not contain common polymorphism affecting mRNA levels in adult brain. Mol Psychiatry, 9, 109-14.
31. Fukuda, Y., Koga, M., Arai, M., Noguchi, E., Ohtsuki, T., Horiuchi, Y., Ishiguro, H., Niizato, K., Iritani, S., Itokawa, M. et al. (2006) Monoallelic and unequal allelic expression of the HTR2A gene in human brain and peripheral lymphocytes. Biol Psychiatry, 60, 1331-5.

32. Rovin, B. H., Lu, L. and Saxena, R. (1999) A novel polymorphism in the MCP-1 gene regulatory region that influences MCP-1 expression. Biochem Biophys Res Commun, 259, 344-8.
33. Xu, Y., Porntadavity, S, and St Clair, D. K. (2002) Transcriptional regulation of the human manganese superoxide dismutase gene: the role of specificity protein 1 (Sp1) and activating protein-2 (AP-2). Biochem J, 362, 401-12.
34. Miklos, I., Meyer, I. M. and Nagy, B. (2005) Moments of the Boltzmann distribution for RNA secondary structures. Bull Math Biol, 67, 1031-47.
35. Lengauer, C., Kinzler, K. W. and Vogelstein, B. (1998) Genetic instabilities in human cancers. Nature, 396, 643-9.
36. Duan, J., Wainwright, M. S., Comeron, J. M., Saitou, N., Sanders, A. R., Gelernter, J. and Gejman, P. V. (2003) Synonymous mutations in the human dopamine receptor D2 (DRD2) affect mRNA stability and synthesis of the receptor. Hum Mol Genet, 12, 205-16.
37. Howe, D. and Lynas, C. (2001) The cyclin D1 alternative transcripts [a] and [b] are expressed in normal and malignant lymphocytes and their relative levels are influenced by the polymorphism at codon 241. Haematologica, 86, 563-9.
38. Nackley, A. G., Shabalina, S. A., Tchivileva, I. E., Satterfield, K., Korchynskyi, O., Makarov, S. S., Maixner, W. and Diatchenko, L. (2006) Human catechol-O-methyltransferase haplotypes modulate protein expression by altering mRNA secondary structure. Science, 314, 1930-3.
39. Sayed-Tabatabaei, F. A., Oostra, B. A., Isaacs, A., van Duijn, C. M. and Witteman, J. C. (2006) ACE polymorphisms. Circ Res, 98, 1123-33.
40. Sam, F., Kerstetter, D. L., Pimental, D. R., Mulukutla, S., Tabaee, A., Bristow, M. R., Colucci, W. S, and Sawyer, D. B. (2005) Increased reactive oxygen species production and functional alterations in antioxidant enzymes in human failing myocardium. J Card Fail, 11, 473-80.
41. Hiroi, S., Harada, H., Nishi, H., Satoh, M., Nagai, R. and Kimura, A. (1999) Polymorphisms in the SOD2 and HLA-DRB1 genes are associated with nonfamilial idiopathic dilated cardiomyopathy in Japanese. Biochem Biophys Res Commun, 261, 332-9.
42. Valenti, L., Conte, D., Piperno, A., Dongiovanni, P., Fracanzani, A. L., Fraquelli, M., Vergani, A., Gianni, C., Carmagnola, L. and Fargion, S. (2004) The mitochondrial superoxide dismutase A16V polymorphism in the cardiomyopathy associated with hereditary haemochromatosis. J Med Genet, 41, 946-50.
43. Hung, R. J., Boffetta, P., Brennan, P., Malaveille, C., Gelatti, U., Placidi, D., Carta, A., Hautefeuille, A. and Porru, S. (2004) Genetic polymorphisms of MPO, COMT, MnSOD, NQO1, interactions with environmental exposures and bladder cancer risk. Carcinogenesis, 25, 973-8.
44. Xu, Y., Fang, F., Dhar, S. K., St Clair, W. H., Kasarskis, E. J. and St Clair, D. K. (2007) The role of a single-stranded nucleotide loop in transcriptional regulation of the human sod2 gene. J Biol Chem, 282, 15981-94.
45. Ginsberg, M. D., Feliciello, A., Jones, J. K., Avvedimento, E. V. and Gottesman, M. E. (2003) PKA-dependent binding of mRNA to the mitochondria AKAP121 protein. J Mol Biol, 327, 885-97.
46. Huang, Y., He, T. and Domann, F. E. (1999) Decreased expression of manganese superoxide dismutase in transformed cells is associated with increased cytosine methylation of the SOD2 gene. DNA Cell Biol, 18, 643-52.
47. Chasman, D. I., Posada, D., Subrahmanyan, L., Cook, N. R., Stanton, V. P., Jr. and Ridker, P. M. (2004) Pharmacogenetic study of statin therapy and cholesterol reduction. Jama, 291, 2821-7.
48. Kathiresan, S., Melander, O., Guiducci, C., Surti, A., Burtt, N. P., Rieder, M. J., Cooper, G. M., Roos, C., Voight, B. F., Havulinna, A. S. et al. (2008) Six new loci associated with blood low-density lipoprotein cholesterol, high-density lipoprotein cholesterol or triglycerides in humans. Nat Gen, 40, 189-97.
49. Eubank, T. D., Galloway, M., Montague, C. M., Waldman, W. J. and Marsh, C. B. (2003) M-CSF induces vascular endothelial growth factor production and angiogenic activity from human monocytes. J Immunol, 171, 2637-43.
50. Zuker, M. (2003) Mfold web server for nucleic acid folding and hybridization prediction. Nucleic Acids Res, 31, 3406-15.
51. Nakayama, M., Yasue, H., Yoshimura, M., Shimasaki, Y., Kugiyama, K., Ogawa, H., Motoyama, T., Saito, Y., Ogawa, Y., Miyamoto, Y. et al. (1999) T-786→C mutation in the 5'-flanking region of the endothelial nitric oxide synthase gene is associated with coronary spasm. Circulation, 99, 2864-70.

What is claimed is:

1. A method for determining whether or not a hypertensive human has increased risk of myocardial infarction, comprising:
   a.) obtaining a nucleic acid-containing sample from a hypertensive human;
   b.) conducting laboratory analysis of the sample so as to obtain genotype data of the human at rs4290 or at rs7213516, wherein the laboratory analysis is polymerase chain reaction with subsequent pyrosequencing or Taqman assay; and
   c.) determining that the human has increased risk of myocardial infarction if the genotype data indicate that the sample comprises either of (i) the minor allele of rs4290 or (ii) the minor allele of rs7213516; or
   d.) determining that the human has no increased risk of myocardial infarction if the genotype data indicate that the sample does not comprise either of (i) the minor allele of rs4290 or (ii) the minor allele of rs7213516.

2. The method of claim 1, further comprising the step of correlating the data with similar data from a reference population.

3. The method of claim 1, wherein the minor allele of rs4290 is present and the minor allele of rs7213516 is present.

4. A method to determine whether or not a hypertensive human has increased susceptibility for reduced ACE mRNA expression, comprising:
   a.) obtaining a nucleic acid-containing sample from a hypertensive human;
   b.) conducting laboratory analysis of the sample so as to obtain genotype data of the human at rs4290 or at rs7213516, wherein the laboratory analysis is polymerase chain reaction with subsequent pyrosequencing or Taqman assay; and
   c.) determining the human as having increased risk of a susceptibility for reduced ACE mRNA expression if the genotype data indicate that the sample comprises either of (i) the minor allele of rs4290 or (ii) the minor allele of rs7213516; or
   d.) determining the human as having no increased susceptibility for reduced ACE mRNA expression if the physical data indicate that the sample does not comprise either of (i) the minor allele of rs4290 or (ii) the minor allele of rs7213516.

* * * * *

SEQUENCE LISTING

```
<160> NUMBER OF SEQ ID NOS: 290

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgagatgggc catatacagt actac                                         25

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
cccgacgcag ggagac                                                    16

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cccttacaag cagaggtgag ctaa                                           24

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accacctaca gcgtggcc                                                  18

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
catgcccata acaggtcttc atatt                                          25

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgcagtaca aggatctgcc                                                20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacgaatgtg atggccac                                                  18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```
ccccttcccg ctacaactt                                                  19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcccctgata cttggttcga a                                               21

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctctgcaccc ttcctttgat gaggttttgc cct                                  33

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agggcaaaac ctcatcaaag gaagggtgca gag                                  33

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gagcatattt ttaagggctg gttttctctc ctgtggtaac t                         41

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agttaccaca ggagagaaaa ccagccctta aaaatatgct c                         41

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
gagacggagt tttgctcttg ttg                                            23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagagacctg acccacgtga g                                              21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gagtgtgggt catttcctct tt                                             22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agtttagcat ggtgcctagc a                                              21

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggcaaaacc tcatc                                                     15

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtggccatca cattcgtcag                                                20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cccatccttt ctcccatttc t                                              21
```

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gacctcgtga tccgccc                                                       17

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggctcctgc ctgtaccag                                                     19

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccaaggctgt tcacccga                                                      18

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tggctagaaa gggcctcctc tcttt                                              25

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttgaggcgcc gctgaggact                                                    20

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctgccccgca cccttg                                                        16

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccttctgagc gagctgtgc                                                    19

<210> SEQ ID NO 28
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggcggccggc ccgccccgcc ttctgagcga gctgcgt                                37

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgacttgagg gagggtccct                                                   20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcaggagaat ggggttcc                                                     18

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgggccgccg ggccgcggca ggagaatggg gtact                                  35

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aggcgctcca aagctcc                                                      17

-continued

```
<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgatgttgg tgtcgtgcgc cc                                          22

<210> SEQ ID NO 34
<211> LENGTH: 30
<212> TYPE: DNA
<213> ORGANISM: Homo sapiens

<400> SEQUENCE: 34
ttgagcatat ttttaagggc tgttttctc                                   30

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cacagggcaa aacctcaacg                                             20

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ggcgcgccgc gggcccacag ggcaaaacct cacca                            35

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtcatttcct ctttcctctg cac                                         23

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gacgaatgtg atggcctcg                                              19

<210> SEQ ID NO 39
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 39
gggccggccg cgcgacgaat gtgatggccg ca                                      32

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
catgcccata acaggtcttc atatt                                              25

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgcagtacaa ggatctgacc                                                    20

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgccgggccg gccggtgcag tacaaggatc tggct                                   35

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tccccaatgg cctcatg                                                       17

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gccccagcac catttgttaa                                                    20

<210> SEQ ID NO 45
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 45
cagccccaaa ttttgtatat gg                                              22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gttactggag ggcagggatg                                                 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ttctcctttg ttgtgacggc                                                 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tctgtgtgca aatgagctgc                                                 20

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgtcctctgg tatccactgg ct                                              22

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gaccttaggt gtcttgcagg c                                               21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 51
tcctgtgaga tgcacctcca g                                             21

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aggcgctcca aagctcc                                                  17

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtgatgttgg tgtcgtgcg                                                19

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctgcagcccg gcaactt                                                  17

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtatctgtct ccgtatcggc g                                             21

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aaccgctgta cgaggatttc ac                                            22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgattttgtg cagatgttca gg                                            22

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgagatgggc catatacagt actac                                         25

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ccctccgggt agttgtcagg                                               20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctgaaggaca tggtcggctt ag                                            22

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccacgagtcc cctgcatcta c                                             21

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tggaaaccac ctacagcgtg                                               20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ccctcaaggc cacaggtaag t                                             21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cttacctgtg gccttgaggg                                               20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cttctgagcg agcggagttc                                               20

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aagcatcacc aaggagaact ataacc                                        26

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgtattcaca gagagacttg gagaggt                                       27

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gaacacttgc cattttgagc c                                             21

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
aggatggagg aacaaaccta gtaac                                    25

<210> SEQ ID NO 70
<211> LENGTH: 17
<212> TYPE: DNA
<213> ORGANISM: Homo sapiens

<400> SEQUENCE: 70
tgtatgggtt catttct                                             17

<210> SEQ ID NO 71
<211> LENGTH: 17
<212> TYPE: DNA
<213> ORGANISM: Pan sp.

<400> SEQUENCE: 71
tgtacgggtt catttct                                             17

<210> SEQ ID NO 72
<211> LENGTH: 17
<212> TYPE: DNA
<213> ORGANISM: Macaca sp.

<400> SEQUENCE: 72
tgtacaggtt catttct                                             17

<210> SEQ ID NO 73
<211> LENGTH: 16
<212> TYPE: DNA
<213> ORGANISM: Unknown Organism
<220> FEATURE:
<223> OTHER INFORMATION: Description of Unknown Organism: Shrew
      oligonucleotide

<400> SEQUENCE: 73
gtaagggttt gtttct                                              16

<210> SEQ ID NO 74
<211> LENGTH: 17
<212> TYPE: DNA
<213> ORGANISM: Canis sp.

<400> SEQUENCE: 74
tataagagtt tatttat                                             17

<210> SEQ ID NO 75
<211> LENGTH: 17
<212> TYPE: DNA
<213> ORGANISM: Unknown Organism
<220> FEATURE:
<223> OTHER INFORMATION: Description of Unknown Organism: Elephant
      oligonucleotide

<400> SEQUENCE: 75
tgtaagggtt tatttgt                                             17

<210> SEQ ID NO 76
<211> LENGTH: 16
<212> TYPE: DNA
<213> ORGANISM: Galago sp.

<400> SEQUENCE: 76
tggcgcctta gccgct                                              16

```
<210> SEQ ID NO 77
<211> LENGTH: 17
<212> TYPE: DNA
<213> ORGANISM: Unknown Organism
<220> FEATURE:
<223> OTHER INFORMATION: Description of Unknown Organism: Squirrel
      oligonucleotide

<400> SEQUENCE: 77
tgtaagggtt taattct                                                       17

<210> SEQ ID NO 78
<211> LENGTH: 17
<212> TYPE: DNA
<213> ORGANISM: Unknown Organism
<220> FEATURE:
<223> OTHER INFORMATION: Description of Unknown Organism: Armadillo
      oligonucleotide

<400> SEQUENCE: 78
tgtaagggtt tatttct                                                       17

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggttgttcac gtaggccg                                                      18

<210> SEQ ID NO 80
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cagcaggcag ctggct                                                        16

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gagcccagat accccaaa                                                      18

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ttgcggcgca gctgg                                                         15
```

<210> SEQ ID NO 83
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctgaagccgc tgccgaa                                                        17

<210> SEQ ID NO 84
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gggccttaag aaagcgc                                                        17

<210> SEQ ID NO 85
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
agtgcccctg gggcagcctc agagcyggga gcagggagca gggagg                        46

<210> SEQ ID NO 86
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ccatcgccac gctccctctg tcctcrgcct gggccgtggt cttctt                        46

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ttcatcatct acccggaagc c                                                   21

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gaagaagacc acggcccag                                                      19

<210> SEQ ID NO 89

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acgctccctc tgtcctc                                                    17

<210> SEQ ID NO 90
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cttgacacca ctccagttgt caatggwttt gcctctgtgc cgcccttcta cc            52

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggatttgtgt gggagaagcc                                                 20

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tagtgaaaga tggataatgc ccca                                            24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
aatgcctttt ctcacctgtc atct                                            24

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggatttgtgt gggagaagcc                                                 20

<210> SEQ ID NO 95
<211> LENGTH: 24

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tagtgaaaga tggataatgc ccca                                              24

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
aggaataaaa acagctccat gcc                                               23

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
atgcaatcaa tgccccagtc                                                   20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gcgagcctct gcactgagat                                                   20

<210> SEQ ID NO 99
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
agatcttcct attggtgaag ttata                                             25

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
caacccaaga atctgcagct aa                                                22

<210> SEQ ID NO 101
<211> LENGTH: 25
<212> TYPE: DNA
```

<213> ORGANISM: Artificial Sequence
<220> FEATURE:
<223> OTHER INFORMATION: Description of Artificial Sequence: Synthetic
primer

<400> SEQUENCE: 101
ggcataatgt tcacatcaa caaac                                    25

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
tagctttccc cagacacc                                           18

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 103
gtcctgtctc tctgaacttt ggg                                     23

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 104
gagctgtatg caatgcttgc c                                       21

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 105
attgtagacc agagggagca ct                                      22

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 106
taaagcagca catagcactg g                                       21

<210> SEQ ID NO 107
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 107
gcagatagcc acaatgacct t                                              21

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cctttccaat atgtacaagc tcc                                            23

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gcaaatataa gctgggaaaa aagttt                                         26

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aattaactac aaaatcagga gtttcatcag                                     30

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aaatccattt tcaactggca gg                                             22

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ttcctctcag catcttctcc ac                                             22

<210> SEQ ID NO 113
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 113
gggcagatgg atggtctgtc                                            20

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gccggcagat gtaactggta c                                          21

<210> SEQ ID NO 115
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gggctgaagc tgggatc                                               17

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ctgacttgct tccggagttt                                            20

<210> SEQ ID NO 117
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ctccccgcca aagca                                                 15

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
cattcctttt tttggacact ggt                                        23

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 119
caagtttgtg cagtattgta gcca                                          24

<210> SEQ ID NO 120
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
atgtagaaaa tataaataga ctgctttagg ta                                 32

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gaaacggtcg cttcgacgt                                                19

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ggcagaagga agagttctgg g                                             21

<210> SEQ ID NO 123
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
agtaaccttg gaaccttggt gcaggcccca gatga                              35

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
aatactccgt aagaccacac gtc                                           23

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 125
actcgacttc ctctgaaatg ga                                              22

<210> SEQ ID NO 126
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gctgtagatt ttgtcaaaga tagattc                                         27

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gaacgagtgg aatatctctt tctcataa                                        28

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gcggaggtag gcattggg                                                   18

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cataattttt acggtggaag c                                               21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ccagagctgc ctgttcaaaa t                                               21

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 131
atgagcttca ggatcatctc cac                                          23

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tgctcttcac tggcctctt                                               19

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ttccaggagc ttctgtgcct                                              20

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gccgttgctg gagtagcc                                                18

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tcttctttga aggcctatgg                                              20

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
caggaatcca agtgccacc                                               19

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137

```
ccacaggcat ggtactgg                                                  18

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ccaacatcag ggaccaggag                                                20

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
aagtagagcc atccatccat gc                                             22

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gattggactg gaagagtggg                                                20

<210> SEQ ID NO 141
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ctgctcccca cttgcag                                                   17

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ttttcctaac tcgcccgct                                                 19

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
```
tgggtgtaaa aaagagcgag c                                                    21

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cctcctcctg ccataccc                                                        18

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gagtggcctc ggaagctg                                                        18

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ggaaacactg ggctgaggg                                                       19

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ggtgtcctac tgccccc                                                         17

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tcaccatggg catttgatt                                                       19

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ccacagcggt gatcattgac                                                      20

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
tgagagcagc tccgagtcc                                                  19

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ggaggtttga gacagctgcc                                                 20

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ctgcagcaga gcctggaag                                                  19

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ctgcagcaga gcctggaag                                                  19

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
cctatggaga caacagccgg                                                 20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ggcatgtatg ttggcctcct                                                 20

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
ctcctttgct gccctcac                                                   18

<210> SEQ ID NO 157
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
tttctcactc gtcctggtag atctt                                           25

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
actgtttcca accagggcc                                                  19

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
ctctgcacct tcaggttcag                                                 20

<210> SEQ ID NO 160
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
ttgttgaaat gaaaatgttg tctgg                                           25

<210> SEQ ID NO 161
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
caatcatatt tagtttgact caccttcc                                        28

```
<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
tgaaagataa gaaagaacta gaaggt                                         26

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
aagtagagcc atccatccat gc                                             22

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gattggactg gaagagtggg                                                20

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gcaggtggag aaggcattg                                                 19

<210> SEQ ID NO 166
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tgtgtccaga ggagcccat                                                 19

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ggctcaccag gaaagcaaa                                                 19

<210> SEQ ID NO 168
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
accgcccgcc tgtgcccatc a                                              21

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tgtgtccaga ggagcccat                                                 19

<210> SEQ ID NO 170
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ggctcaccag gaaagcaaa                                                 19

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
cgagcagagg cgcttctccg t                                              21

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tgtgtccaga ggagcccat                                                 19

<210> SEQ ID NO 173
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ggctcaccag gaaagcaaa                                                 19

<210> SEQ ID NO 174
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
agcttcaatg atgagaacct g                                              21

<210> SEQ ID NO 175
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggcccagcca ccatg                                                     15

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gcacagcaca aagctcatag gg                                             22

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gtgtctttgc tttcctggtg a                                              21

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
acatttcttc tcctggatca cca                                            23

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
acactagaag cgtgtggcgt t                                              21

<210> SEQ ID NO 180
<211> LENGTH: 19
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 180
ctggatcacc agtcactgc                                                    19

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ctgcttgaag tcgtcagtta c                                                 21

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
aggaaaatgg ctgttggtat gatc                                              24

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cgcaactgca aatgccag                                                     18

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gctgttggta tgatcctagc                                                   20

<210> SEQ ID NO 185
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gaaatggccc cagccc                                                       16

<210> SEQ ID NO 186
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
catctgccag attcaagact tgtag                                          25

<210> SEQ ID NO 187
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
aacctcctgg ggacctg                                                   17

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ccagctgact ctccccgac                                                 19

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gcatgcccat tcttctctgg                                                20

<210> SEQ ID NO 190
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
cgatcacatg tcgtgaactg actgactggt ttggcggggc tgtc                     44

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ccagctgact ctccccgac                                                 19

<210> SEQ ID NO 192
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 192
gcatgcccat tcttctctgg                                                 20

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
ggagtgctgt ggagacc                                                    17

<210> SEQ ID NO 194
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
agcctgagtc agggccc                                                    17

<210> SEQ ID NO 195
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
accgcctgct ccacg                                                      15

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
cccagaggct gagttttct                                                  19

<210> SEQ ID NO 197
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tgaacatgca cagccgc                                                    17

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 198
cgaaggcata ggtgatgtcc                                               20

<210> SEQ ID NO 199
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
ttgtaggtgc ccacggc                                                  17

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
cacatgcaag aaggagccct                                               20

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ggtggtctgc aatgtactgg a                                             21

<210> SEQ ID NO 202
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ccgcagcacc aaagc                                                    15

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
ccctctccta gcgaagcaga t                                             21

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 204
ggtccttgag cctctcggg                                                19

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
ctagcgaagc agattggagc                                               20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ccgtcagtac catggacagc                                               20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
gagtacgcca aggcatcagt                                               20

<210> SEQ ID NO 208
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
actgatcgac ttgtcccact tagatggc                                      28

<210> SEQ ID NO 209
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
actgactgac tgaccatggg tcggacaggt                                    30

<210> SEQ ID NO 210
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 210
gacaccaggc tctacagtaa tgacttt                                        27

<210> SEQ ID NO 211
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
tgtccagtta aatgcatcag aagtg                                          25

<210> SEQ ID NO 212
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
actgactgac tggaaccttg actcatcaga agtgttagct tctcc                    45

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
gcttgacatc attggctgac a                                              21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
ctggtcctca tccaacagct c                                              21

<210> SEQ ID NO 215
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
aaccttggaa ccttggggct gacact                                         26

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tatctgtttg cttctaaagg tttc                                    24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tggacacact atttttcatt ttag                                    24

<210> SEQ ID NO 218
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ggttctagta gattccagca ataaaatt                                28

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
acgagacttt ctggcaggac tg                                      22

<210> SEQ ID NO 220
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ttaattctcc aatggaggaa agga                                    24

<210> SEQ ID NO 221
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gatcccctct acacccc                                            17

<210> SEQ ID NO 222
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acgagacttt ctggcaggac tg                                              22

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
ttaattctcc aatggaggaa agga                                            24

<210> SEQ ID NO 224
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
aaaggagtcc tgctccata                                                  19

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
atgggaggca tggaggctgt c                                               21

<210> SEQ ID NO 226
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
cgagaaggaa agtgctgaag gtgac                                           25

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
ggcatggagg ctgtcatcac                                                 20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
atccagtttt ggctgtatgc                                                 20

<210> SEQ ID NO 229
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ctgttcttta agtttctcac acatt                                           25

<210> SEQ ID NO 230
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
tgttttatag aggttcttga tttttac                                         27

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
ctgctgccac tactgctgct gct                                             23

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
cacctttccc tcgatcacca                                                 20

<210> SEQ ID NO 233
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
tagcacaccg aggccc                                                     16

<210> SEQ ID NO 234
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ccacgtcctc ggtcacctct attaac                                          26

<210> SEQ ID NO 235
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 235
cacaataaag gctcccaaaa tgatcc                                          26

<210> SEQ ID NO 236
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 236
tcgaaatccg gatctcctgt gtatgt                                          26

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 237
aaatggtctc gggaaggtga                                                 20

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 238
tttgattcag gttcttgtac ccag                                            24

<210> SEQ ID NO 239
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 239
ggaaggtgac cgagaaaga                                                  19

<210> SEQ ID NO 240
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
acttcagacc agagcttcca gc                                              22

```
<210> SEQ ID NO 241
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
atgcacttaa tgacagctcc ca                                              22

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
gagaaaccag ttaattcagc g                                               21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
tctgccccac aggtgtagtt c                                               21

<210> SEQ ID NO 244
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
ggcatctctg agccagctg                                                  19

<210> SEQ ID NO 245
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
atctctgagc cagctgagt                                                  19

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
tggtgttgca tttagccctg g                                               21

<210> SEQ ID NO 247
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
agccacaaca atcctgcaca                                                  20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
ggcatggagc tgaacagtac                                                  20

<210> SEQ ID NO 249
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
gtgacaccaa ggagcagcg                                                   19

<210> SEQ ID NO 250
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
tgtcaatggc ctccagcac                                                   19

<210> SEQ ID NO 251
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
agcgcatcct gaacca                                                      16

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gacgggactg ataacagcag c                                                21

<210> SEQ ID NO 253
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
cacaagcatc cattcatcca a                                            21

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
catccaagtc tcccaacact                                              20

<210> SEQ ID NO 255
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
ggcagtcact tttgatgaaa caga                                         24

<210> SEQ ID NO 256
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
gagtattgaa ttccccgaga tgttag                                       26

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
caatcagata ccaaaatatt caaa                                         24

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
gctgcaccgt cacagtgtct                                              20

<210> SEQ ID NO 259
<211> LENGTH: 23
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 259
tgatatcttt gtctgtggcc ctc                                            23

<210> SEQ ID NO 260
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
gtctgatttg tatgccatga ac                                             22

<210> SEQ ID NO 261
<211> LENGTH: 4020
<212> TYPE: DNA
<213> ORGANISM: Homo sapiens

<400> SEQUENCE: 261
gccgagcacc gcgcaccgcg tcatgggggc cgcctcgggc cgccggggc cggggctgct      60 gctgccgctg ccgctgctgt tgctgctgcc gccgcagccc gccctggcgt tggaccccgg    120
gctgcagccc ggcaactttt ctgctgacga ggccggggcg cagctcttcg cgcagagcta    180
caactccagc gccgaacagg tgctgttcca gagcgtggcc gccagctggg cgcacgacac    240
caacatcacc gcggagaatg caaggcgcca ggaggaagca gccctgctca gccaggagtt    300
tgcggaggcc tggggccaga aggccaagga gctgtatgaa ccgatctggc agaacttcac    360
ggacccgcag ctgcgcagga tcatcggagc tgtgcgaacc ctgggctctg ccaacctgcc    420
cctggctaag cggcagcagt acaacgcccct gctaagcaac atgagcagga tctactccac    480
cgccaaggtc tgcctcccca caagactgc cacctgctgg tccctggacc cagatctcac    540
caacatcctg gcttcctcgc gaagctacgc catgctcctg tttgcctggg agggctggca    600
caacgctgcg ggcatcccgc tgaaaccgct gtacgaggat ttcactgccc tcagcaatga    660
agcctacaag caggacggct tcacagacac gggggcctac tggcgctcct ggtacaactc    720
ccccaccttc gaggacgatc tggaacacct ctaccaacag ctagagcccc tctacctgaa    780
cctccatgcc ttcgtccgcc gcgcactgca tcgccgatac ggagacagat acatcaacct    840
caggggaccc atccctgctc atctgctggg agacatgtgg gcccagagct gggaaaacat    900
ctacgacatg gtggtgcctt cccagacaa gcccaacctc gatgtcacca gtactatgct    960
gcagcagggc tggaacgcca cgcacatgtt ccggtggca gaggagttct tcacctccct   1020
ggagctctcc cccatgcctc ccgagttctg ggaaggtcg atgctggaga agccggccga   1080
cgggcgggaa gtggtgtgcc acgcctcggc ttggacttc tacaacagga aagacttcag   1140
gatcaagcag tgcacacggg tcacgatgga ccagctctcc acagtgcacc atgagatggg   1200
ccatatacag tactacctgc agtacaagga tctgcccgtc tccctgcgtc gggggccaa   1260 ccccggcttc catgaggcca ttgggacgt gctggcgctc tcggtctcca ctcctgaaca   1320
tctgcacaaa atcggcctgc tggaccgtgt caccaatgac acggaaagtg acatcaatta   1380
cttgctaaaa atggcactgg aaaaaattgc cttcctgccc tttggctact ggtggacca   1440 gtggcgctgg ggggtcttta gtgggcgtac ccccccttcc cgctacaact cgactggtg   1500

```
gtatcttcga accaagtatc aggggatctg tcctcctgtt acccgaaacg aaacccactt    1560
tgatgctgga gctaagtttc atgttccaaa tgtgacacca tacatcaggt actttgtgag    1620
ttttgtcctg cagttccagt tccatgaagc cctgtgcaag gaggcaggct atgagggccc    1680
actgcaccag tgtgacatct accggtccac caaggcaggg gccaagctcc ggaaggtgct    1740
gcaggctggc tcctccaggc cctggcagga ggtgctgaag acatggtcg gcttagatgc     1800
cctggatgcc cagccgctgc tcaagtactt ccagccagtc acccagtggc tgcaggagca    1860
gaaccagcag aacggcgagg tcctgggctg gcccgagtac cagtggcacc gccgttgcc     1920
tgacaactac ccggagggca tagacctggt gactgatgag gctgaggcca gcaagtttgt    1980
ggaggaatat gaccggacat cccaggtggt gtggaacgag tatgccgagg ccaactggaa    2040
ctacaacacc aacatcacca cagagaccag caagattctg ctgcagaaga acatgcaaat    2100
agccaaccac accctgaagt acggcaccca ggccaggaag tttgatgtga accagttgca    2160
gaacaccact atcaagcgga tcataaagaa ggttcaggac ctagaacggg cagcgctgcc    2220
tgcccaggag ctggaggagt acaacaagat cctgttggat atggaaacca cctacagcgt    2280
ggccactgtg tgccacccga atggcagctg cctgcagctc gagccagatc tgacgaatgt    2340
gatggccaca tcccggaaat atgaagacct gttatgggca tgggagggct ggcgagacaa    2400
ggcggggaga gccatcctcc agttttaccc gaaatacgtg gaactcatca accaggctgc    2460
ccggctcaat ggctatgtag atgcagggga ctcgtggagg tctatgtacg agacaccatc    2520
cctggagcaa gacctggagc ggctcttcca ggagctgcag ccactctacc tcaacctgca    2580
tgcctacgtg cgccgggccc tgcaccgtca ctacggggcc cagcacatca acctggaggg    2640
gcccattcct gctcacctgc tgggaacat gtgggcgcag acctggtcca acatctatga     2700
cttggtggtg cccttcccett cagcccccte gatggacacc acagaggcta tgctaaagca   2760
gggctggacg cccaggagga tgtttaagga ggctgatgat ttcttcacct ccctgggcct    2820
gctgccgtg cctcctgagt tctggaacaa gtcgatgctg gagaagccaa ccgacgggcg     2880
ggaggtggtc tgccacgcct cggcctggga cttctacaac ggcaaggact ccggatcaa     2940
gcagtgcacc accgtgaact tggaggacct ggtggtggcc caccacgaaa tgggccacat    3000
ccagtatttc atgcagtaca aagacttacc tgtggccttg agggagggtg ccaaccccgg    3060
cttccatgag gccattgggg acgtgctagc cctctcagtg tctacgccca agcacctgca    3120
cagtctcaac ctgctgagca gtgagggtgg cagcgacgag catgacatca actttctgat    3180
gaagatggcc cttgacaaga tcgcctttat ccccttcagc tacctcgtcg atcagtggcg    3240
ctggagggta tttgatggaa gcatcaccaa ggagaactat aaccaggagt ggtggagcct    3300
caggctgaag taccagggcc tctgcccccc agtgcccagg actcaaggtg actttgaccc    3360
aggggccaag ttccacattc cttctagcgt gccttacatc aggtactttg tcagcttcat    3420
catccagttc cagttccacg aggcactgtg ccaggcagct ggccacacgg ccccctgca    3480
caagtgtgac atctaccagt ccaaggaggc cgggcagcgc ctggcgaccg ccatgaagct    3540
gggcttcagt aggccgtggc cggaagccat gcagctgatc acgggccagc caacatgag    3600
cgcctcggcc atgttgagct acttcaagcc gctgctggac tggctccgca cggagaacga    3660
gctgcatggg gagaagctgg gctggccgca gtacaactgg acgccgaact ccgctcgctc    3720
agaagggccc ctcccagaca gcggccgcgt cagcttcctg ggcctggacc tggatgcgca    3780
gcaggcccgc gtgggccagt ggctgctgct cttcctgggc atcgccctgc tggtagccac    3840
```

| | |
|---|---|
| cctgggcctc agccagcggc tcttcagcat ccgccaccgc agcctccacc ggcactccca | 3900 |
| cgggccccag ttcggctccg aggtggagct gagacactcc tgaggtgacc cggctgggtc | 3960 |
| ggccctgccc aagggcctcc caccagagac tgggatggga acactggtgg gcagctgagg | 4020 |

<210> SEQ ID NO 262
<211> LENGTH: 1593
<212> TYPE: DNA
<213> ORGANISM: Homo sapiens
<400> SEQUENCE: 262

| | |
|---|---|
| gcggtgccct tgcggcgcag ctggggtcgc ggccctgctc cccgcgcttt cttaaggccc | 60 |
| gcgggcggcg caggagcggc actcgtggct gtggtggctt cggcagcggc ttcagcagat | 120 |
| cggcggcatc agcggtagca ccagcactag cagcatgttg agccgggcag tgtgcggcac | 180 |
| cagcaggcag ctggctccgg ttttggggta tctgggctcc aggcagaagc acagcctccc | 240 |
| cgacctgccc tacgactacg cgccctgga acctcacatc aacgcgcaga tcatgcagct | 300 |
| gcaccacagc aagcaccacg cggcctacgt gaacaacctg aacgtcaccg aggagaagta | 360 |
| ccaggaggcg ttggccaagg agatgttac agcccagata gctcttcagc ctgcactgaa | 420 |
| gttcaatggt ggtggtcata tcaatcatag cattttctgg acaaacctca gccctaacgg | 480 |
| tggtggagaa cccaaagggg agttgctgga agccatcaaa cgtgactttg gttcctttga | 540 |
| caagtttaag gagaagctga cggctgcatc tgttggtgtc caaggctcag gttggggttg | 600 |
| gcttggtttc aataaggaac ggggacactt acaaattgct gcttgtccaa atcaggatcc | 660 |
| actgcaagga caacaggcc ttattccact gctggggatt gatgtgtggg agcacgctta | 720 |
| ctaccttcag tataaaaatg tcaggcctga ttatctaaaa gctatttgga atgtaatcaa | 780 |
| ctgggagaat gtaactgaaa gatacatggc ttgcaaaaag taaaccacga tcgttatgct | 840 |
| gagtatgtta agctctttat gactgttttt gtagtggtat agagtactgc agaatacagt | 900 |
| aagctgctct attgtagcat ttcttgatgt tgcttagtca cttatttcat aaacaactta | 960 |
| atgttctgaa taatttctta ctaaacattt tgttattggg caagtgattg aaaatagtaa | 1020 |
| atgctttgtg tgattgaatc tgattggaca ttttcttcag agagctaaat tacaattgtc | 1080 |
| atttataaaa ccatcaaaaa tattccatcc atatactttg gggacttgta gggatgcctt | 1140 |
| tctagtccta ttctattgca gttatagaaa atctagtctt ttgccccagt tacttaaaaa | 1200 |
| taaaatatta acactttccc aagggaaaca ctcggctttc tatagaaaat tgcacttttt | 1260 |
| gtcgagtaat cctctgcagt gatacttctg gtagatgtca cccagtggtt tttgttaggt | 1320 |
| caaatgttcc tgtatagttt ttgcaaatag agctgtatac tgtttaaatg tagcaggtga | 1380 |
| actgaactgg ggtttgctca cctgcacagt aaaggcaaac ttcaacagca aaactgcaaa | 1440 |
| aaggtggttt ttgcagtagg agaaaggagg atgtttattt gcagggcgcc aagcaaggag | 1500 |
| aattgggcag ctcatgcttg agacccaatc tccatgatga cctacaagct agagtattta | 1560 |
| aaggcagtgg taaatttcag gaaagcagaa gtt | 1593 |

<210> SEQ ID NO 263
<211> LENGTH: 3925
<212> TYPE: DNA
<213> ORGANISM: Homo sapiens
<400> SEQUENCE: 263

| | |
|---|---|
| cggagcggga gggaggctt cgcggaacgc tctcggcgcc aggactcgcg tgcaaagccc | 60 |
| aggcccgggc ggccagacca agagggaaga agcacagaat tcctcaactc ccagtgtgcc | 120 |

```
catgagtaag agcaaatgct ccgtgggact catgtcttcc gtggtggccc cggctaagga      180
gcccaatgcc gtgggcccga aggaggtgga gctcatcctt gtcaaggagc agaacggagt      240
gcagctcacc agctccaccc tcaccaaccc gcggcagagc cccgtggagg cccaggatcg      300
ggagacctgg ggcaagaaga tcgactttct cctgtccgtc attggctttg ctgtggacct      360
ggccaacgtc tggcggttcc cctacctgtg ctacaaaaat ggtggcggtg ccttcctggt      420
cccctacctg ctcttcatgg tcattgctgg gatgccactt ttctacatgg agctggccct      480
cggccagttc aacagggaag gggccgctgg tgtctggaag atctgcccca tactgaaagg      540
tgtgggcttc acgtcatcc tcatctcact gtatgtcggc ttcttctaca acgtcatcat      600
cgcctgggcg ctgcactatc tcttctcctc cttcaccacg gagctcccct ggatccactg      660
caacaactcc tggaacagcc ccaactgctc ggatgcccat cctggtgact ccagtggaga      720
cagctcgggc ctcaacgaca cttttgggac cacacctgct gccgagtact ttgaacgtgg      780
cgtgctgcac ctccaccaga gccatggcat cgacgacctg gggcctccgc ggtggcagct      840
cacagcctgc ctggtgctgg tcatcgtgct gctctacttc agcctctgga agggcgtgaa      900
gacctcaggg aaggtggtat ggatcacagc caccatgcca tacgtggtcc tcactgccct      960
gctcctgcgt ggggtcaccc tccctggagc catagacggc atcagagcat acctgagcgt     1020
tgacttctac cggctctgcg aggcgtctgt ttggattgac gcggccaccc aggtgtgctt     1080
ctccctgggc gtggggttcg gggtgctgat cgccttctcc agctacaaca agttcaccaa     1140
caactgctac agggacgcga ttgtcaccac ctccatcaac tccctgacga gcttctcctc     1200
cggcttcgtc gtcttctcct tcctggggta catggcacag aagcacagtg tgcccatcgg     1260
ggacgtggcc aaggacgggc cagggctgat cttcatcatc tacccggaag ccatcgccac     1320
gctccctctg tcctcagcct gggccgtggt cttcttcatc atgctgctca ccctgggtat     1380
cgacagcgcc atgggtggta tggagtcagt gatcaccggg ctcatcgatg agttccagct     1440
gctgcacaga caccgtgagc tcttcacgct cttcatcgtc ctggcgacct tcctcctgtc     1500
cctgttctgc gtcaccaacg gtggcatcta cgtcttcacg ctcctggacc attttgcagc     1560
cggcacgtcc atcctctttg gagtgctcat cgaagccatc ggagtggcct ggttctatgg     1620
tgttgggcag ttcagcgacg acatccagca gatgaccggg cagcggccca gcctgtactg     1680
gcggctgtgc tggaagctgg tcagcccctg cttctctcct gttcgtggtcg tggtcagcat     1740 tgtgaccttc agacccccc actacggagc ctacatcttc cccgactggg ccaacgcgct     1800
gggctgggtc atcgccacat cctccatggc catggtgccc atctatgcgg cctacaagtt     1860
ctgcagcctg cctgggtcct ttcgagagaa actggcctac gccattgcac ccgagaagga     1920
ccgtgagctg gtgacagag gggaggtgcg ccagttcacg ctccgccact ggctcaaggt     1980
gtagagggag cagagacgaa gaccccagga agtcatcctg caatgggaga gacacgaaca     2040
aaccaaggaa atctaagttt cgagagaaag gagggcaact tctactcttc aacctctact     2100
gaaaacacaa acaacaaagc agaagactcc tctcttctga ctgtttacac ctttccgtgc     2160
cgggagcgca cctcgccgtg tcttgtgttg ctgtaataac gacgtagatc tgtgcagcga     2220
ggtccacccc gttgttgtcc ctgcaggca gaaaaacgtc taacttcatg ctgtctgtgt     2280
gaggctccct ccctccctgc tccctgctcc cggctctgag gctgcccag gggcactgtg     2340 ttctcaggcg gggatcacga tccttgtaga cgcacctgct gagaatcccc gtgctcacag     2400
tagcttccta gaccatttac tttgcccata ttaaaaagcc aagtgtcctg cttggtttag     2460
```

```
ctgtgcagaa ggtgaaatgg aggaaaccac aaattcatgc aaagtccttt cccgatgcgt    2520
ggctcccagc agaggccgta aattgagcgt tcagttgaca cattgcacac acagtctgtt    2580
cagaggcatt ggaggatggg ggtcctggta tgtctcacca ggaaattctg tttatgttct    2640
tgcagcagag agaaataaaa ctccttgaaa ccagctcagg ctactgccac tcaggcagcc    2700
tgtgggtcct tgcggtgtag ggaacggcct gagaggagcg tgtcctatcc ccggacgcat    2760
gcagggcccc cacaggagcg tgtcctatcc ccggacgcat gcagggcccc cacaggagca    2820
tgtcctatcc ctggacgcat gcagggcccc cacaggagcg tgtactaccc cagaacgcat    2880
gcagggcccc cacaggagcg tgtactaccc caggacgcat gcagggcccc cactggagcg    2940
tgtactaccc caggacgcat gcagggcccc cacaggagcg tgtcctatcc ccggaccgga    3000
cgcatgcagg gccccacag gagcgtgtac taccccagga cgcatgcagg gccccacag    3060 gagcgtgtac taccccagga tgcatgcagg gccccacag gagcgtgtac taccccagga    3120
cgcatgcagg gccccatgc aggcagcctg cagaccacac tctgcctggc cttgagccgt    3180
gacctccagg aagggacccc actggaattt tatttctctc aggtgcgtgc cacatcaata    3240
acaacagttt ttatgtttgc gaatggcttt ttaaaatcat atttacctgt gaatcaaaac    3300
aaattcaaga atgcagtatc cgcgagcctg cttgctgata ttgcagtttt tgtttacaag    3360
aataattagc aatactgagt gaaggatgtt ggccaaaagc tgctttccat ggcacactgc    3420
cctctgccac tgacaggaaa gtggatgcca tagtttgaat tcatgcctca agtcggtggg    3480
cctgcctacg tgctgcccga gggcaggggc cgtgcagggc cagtcatggc tgtcccctgc    3540
aagtggacgt gggctccagg gactggagtg taatgctcgg tggagccgt cagcctgtga    3600 actgccaggc agctgcagtt agcacagagg atggcttccc cattgccttc tggggaggga    3660
cacagaggac ggcttcccca tcgccttctg gccgctgcag tcagcacaga gagcggcttc    3720
cccattgcct tctggggagg gacacagagg acagcttccc catcgccttc tggctgctgc    3780
agtcagcaca gagagcggct tccccatcgc cttctgggga gggctccgt gtagcaaccc    3840 aggtgttgtc cgtgtctgtt gaccaatctc tattcagcat cgtgtgggtc cctaagcaca    3900
ataaaagaca tccacaatgg aaaaa                                          3925
```

<210> SEQ ID NO 264
<211> LENGTH: 1835
<212> TYPE: DNA
<213> ORGANISM: Homo sapiens

<400> SEQUENCE: 264

```
atggattctc ttgtggtcct tgtgctctgt ctctcatgtt tgcttctcct ttcactctgg     60
agacagagct ctgggagagg aaaactccct cctggcccca ctcctctccc agtgattgga    120
aatatcctac agataggtat taaggacatc agcaaatcct taaccaatct ctcaaaggtc    180
tatgccccgg tgttcactct gtattttggc ctgaaaccca tagtggtgct gcatggatat    240
gaagcagtga aggaagccct gattgatctt ggagaggagt tttctggaag aggcattttc    300
ccactggctg aaagagctaa cagaggattt ggaattgttt tcagcaatgg aaagaaatgg    360
aaggagatcc ggcgtttctc cctcatgacg ctgcggaatt tgggatggg aagaggagc    420 attgaggacc gtgttcaaga ggaagcccgc tgccttgtgg aggagttgag aaaaaccaag    480
gcctcaccct gtgatccac tttcatcctg gctgtgctc cctgcaatgt gatctgctcc    540 attatttttcc ataaacgttt tgattataaa gatcagcaat tcttaacctt aatgaaaag    600 ttgaatgaaa acatcaagat tttgagcagc ccctggatcc agatctgcaa taattttct    660
```

-continued

| | |
|---|---|
| cctatcattg attacttccc gggaactcac aacaaattac ttaaaaacgt tgcttttatg | 720 |
| aaaagttata ttttggaaaa agtaaaagaa caccaagaat caatggacat gaacaaccct | 780 |
| caggacttta ttgattgctt cctgatgaaa atggagaagg aaaagcacaa ccaaccatct | 840 |
| gaatttacta ttgaaagctt ggaaaacact gcagttgact tgtttggagc tgggacagag | 900 |
| acgacaagca caaccctgag atatgctctc cttctcctgc tgaagcaccc agaggtcaca | 960 |
| gctaaagtcc aggaagagat tgaacgtgtg attggcagaa accggagccc ctgcatgcaa | 1020 |
| gacaggagcc acatgcccta cacagatgct gtggtgcacg aggtccagag atacattgac | 1080 |
| cttctcccca ccagcctgcc ccatgcagtg acctgtgaca ttaaattcag aaactatctc | 1140 |
| attcccaagg gcacaaccat attaatttcc ctgacttctg tgctacatga caacaaagaa | 1200 |
| tttcccaacc cagagatgtt tgaccctcat cactttctgg atgaaggtgg caattttaag | 1260 |
| aaaagtaaat acttcatgcc tttctcagca ggaaaacgga tttgtgtggg agaagccctg | 1320 |
| gccggcatgg agctgttttt attcctgacc tccattttac agaactttaa cctgaaatct | 1380 |
| ctggttgacc caaagaacct tgacaccact ccagttgtca atggatttgc ctctgtgccg | 1440 |
| cccttctacc agctgtgctt cattcctgtc tgaagaagag cagatggcct ggctgctgct | 1500 |
| gtgcagtccc tgcagctctc tttcctctgg ggcattatcc atctttgcac tatctgtaat | 1560 |
| gcctttctc acctgtcatc tcacattttc ccttccctga agatctagtg aacattcgac | 1620 |
| ctccattacg gagagtttcc tatgtttcac tgtgcaaata tatctgctat tctccatact | 1680 |
| ctgtaacagt tgcattgact gtcacataat gctcatactt atctaatgta gagtattaat | 1740 |
| atgttattat taaatagaga aatatgattt gtgtattata attcaaaggc atttcttttc | 1800 |
| tgcatgatct aaataaaaag cattattatt tgctg | 1835 |

<210> SEQ ID NO 265
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
ttgccccagc accatttgtt aaaaa                                    25

<210> SEQ ID NO 266
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
ttgtatgtta ctggagggca gggatg                                   26

<210> SEQ ID NO 267
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
cctagcacag ggcaaaacct catc                                     24

<210> SEQ ID NO 268
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 268
aggtcaccag ttaccacagg agagaaaa                                    28

<210> SEQ ID NO 269
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 269
acaatggaat agaattgaga gtccagaaat gaa                              33

<210> SEQ ID NO 270
<211> LENGTH: 30
<212> TYPE: DNA
<213> ORGANISM: Pan sp.

<400> SEQUENCE: 270
ttgagcatat ttttaagggc tgttttttctc                                 30

<210> SEQ ID NO 271
<211> LENGTH: 30
<212> TYPE: DNA
<213> ORGANISM: Macaca sp.

<400> SEQUENCE: 271
ttgagcatat ttttaagggc tgttttttctc                                 30

<210> SEQ ID NO 272
<211> LENGTH: 29
<212> TYPE: DNA
<213> ORGANISM: Galago sp.

<400> SEQUENCE: 272
ttggcatatt cttgagggct gttttttctt                                  29

<210> SEQ ID NO 273
<211> LENGTH: 30
<212> TYPE: DNA
<213> ORGANISM: Unknown Organism
<220> FEATURE:
<223> OTHER INFORMATION: Description of Unknown Organism: Shrew oligonucleotide

<400> SEQUENCE: 273
ttgggcatat atttaaaggc tgatttcctc                                  30

<210> SEQ ID NO 274
<211> LENGTH: 30
<212> TYPE: DNA
<213> ORGANISM: Canis sp.

<400> SEQUENCE: 274
tggggcatat tttcaaggtt ttttttcctc                                  30

<210> SEQ ID NO 275
<211> LENGTH: 30
<212> TYPE: DNA
<213> ORGANISM: Unknown Organism
<220> FEATURE:
<223> OTHER INFORMATION: Description of Unknown Organism: Elephant
      oligonucleotide

<400> SEQUENCE: 275
ctggtcatat atttaagggc tatttctctc                                         30

<210> SEQ ID NO 276
<211> LENGTH: 30
<212> TYPE: DNA
<213> ORGANISM: Unknown Organism
<220> FEATURE:
<223> OTHER INFORMATION: Description of Unknown Organism: Squirrel
      oligonucleotide

<400> SEQUENCE: 276
ttggccatat ttttaaggac tgttttttctc                                        30

<210> SEQ ID NO 277
<211> LENGTH: 30
<212> TYPE: DNA
<213> ORGANISM: Unknown Organism
<220> FEATURE:
<223> OTHER INFORMATION: Description of Unknown Organism: Armadillo
      oligonucleotide

<400> SEQUENCE: 277
ttgggtattt ttttaactg aattactttc                                          30

<210> SEQ ID NO 278
<211> LENGTH: 12
<212> TYPE: DNA
<213> ORGANISM: Homo sapiens

<400> SEQUENCE: 278
ccttcgatga gg                                                            12

<210> SEQ ID NO 279
<211> LENGTH: 12
<212> TYPE: DNA
<213> ORGANISM: Pan sp.

<400> SEQUENCE: 279
ccttcgatga gg                                                            12

<210> SEQ ID NO 280
<211> LENGTH: 12
<212> TYPE: DNA
<213> ORGANISM: Macaca sp.

<400> SEQUENCE: 280
ccttggatga gg                                                            12

<210> SEQ ID NO 281
<211> LENGTH: 12
<212> TYPE: DNA
<213> ORGANISM: Galago sp.

<400> SEQUENCE: 281
ctttgaatga ag                                                            12

-continued

<210> SEQ ID NO 282
<211> LENGTH: 12
<212> TYPE: DNA
<213> ORGANISM: Unknown Organism
<220> FEATURE:
<223> OTHER INFORMATION: Description of Unknown Organism: Shrew
      oligonucleotide

<400> SEQUENCE: 282
ccttaaatga gg                                                            12

<210> SEQ ID NO 283
<211> LENGTH: 12
<212> TYPE: DNA
<213> ORGANISM: Canis sp.

<400> SEQUENCE: 283
ccttaaatga gg                                                            12

<210> SEQ ID NO 284
<211> LENGTH: 12
<212> TYPE: DNA
<213> ORGANISM: Unknown Organism
<220> FEATURE:
<223> OTHER INFORMATION: Description of Unknown Organism: Elephant
      oligonucleotide

<400> SEQUENCE: 284
catgaatcag gg                                                            12

<210> SEQ ID NO 285
<211> LENGTH: 12
<212> TYPE: DNA
<213> ORGANISM: Unknown Organism
<220> FEATURE:
<223> OTHER INFORMATION: Description of Unknown Organism: Squirrel
      oligonucleotide

<400> SEQUENCE: 285
ccttgaatga gg                                                            12

<210> SEQ ID NO 286
<211> LENGTH: 11
<212> TYPE: DNA
<213> ORGANISM: Unknown Organism
<220> FEATURE:
<223> OTHER INFORMATION: Description of Unknown Organism: Armadillo
      oligonucleotide

<400> SEQUENCE: 286
tcgtgaagat g                                                             11

<210> SEQ ID NO 287
<211> LENGTH: 1306
<212> TYPE: PRT
<213> ORGANISM: Homo sapiens

<400> SEQUENCE: 287

Met Gly Ala Ala Ser Gly Arg Arg Gly Pro Gly Leu Leu Pro Leu
1               5                   10                  15

Pro Leu Leu Leu Leu Leu Pro Pro Gln Pro Ala Leu Ala Leu Asp Pro
                20                  25                  30

Gly Leu Gln Pro Gly Asn Phe Ser Ala Asp Glu Ala Gly Ala Gln Leu
            35                  40                  45

```
Phe Ala Gln Ser Tyr Asn Ser Ala Glu Gln Val Leu Phe Gln Ser
 50                  55                  60

Val Ala Ala Ser Trp Ala His Asp Thr Asn Ile Thr Ala Glu Asn Ala
 65                  70                  75                  80

Arg Arg Gln Glu Glu Ala Ala Leu Leu Ser Gln Glu Phe Ala Glu Ala
                 85                  90                  95

Trp Gly Gln Lys Ala Lys Glu Leu Tyr Glu Pro Ile Trp Gln Asn Phe
            100                 105                 110

Thr Asp Pro Gln Leu Arg Arg Ile Ile Gly Ala Val Arg Thr Leu Gly
            115                 120                 125

Ser Ala Asn Leu Pro Leu Ala Lys Arg Gln Gln Tyr Asn Ala Leu Leu
            130                 135                 140

Ser Asn Met Ser Arg Ile Tyr Ser Thr Ala Lys Val Cys Leu Pro Asn
145                 150                 155                 160

Lys Thr Ala Thr Cys Trp Ser Leu Asp Pro Asp Leu Thr Asn Ile Leu
                165                 170                 175

Ala Ser Ser Arg Ser Tyr Ala Met Leu Leu Phe Ala Trp Glu Gly Trp
            180                 185                 190

His Asn Ala Ala Gly Ile Pro Leu Lys Pro Leu Tyr Glu Asp Phe Thr
            195                 200                 205

Ala Leu Ser Asn Glu Ala Tyr Lys Gln Asp Gly Phe Thr Asp Thr Gly
            210                 215                 220

Ala Tyr Trp Arg Ser Trp Tyr Asn Ser Pro Thr Phe Glu Asp Asp Leu
225                 230                 235                 240

Glu His Leu Tyr Gln Gln Leu Glu Pro Leu Tyr Leu Asn Leu His Ala
                245                 250                 255

Phe Val Arg Arg Ala Leu His Arg Arg Tyr Gly Asp Arg Tyr Ile Asn
            260                 265                 270

Leu Arg Gly Pro Ile Pro Ala His Leu Leu Gly Asp Met Trp Ala Gln
            275                 280                 285

Ser Trp Glu Asn Ile Tyr Asp Met Val Val Pro Phe Pro Asp Lys Pro
            290                 295                 300

Asn Leu Asp Val Thr Ser Thr Met Leu Gln Gln Gly Trp Asn Ala Thr
305                 310                 315                 320

His Met Phe Arg Val Ala Glu Glu Phe Phe Thr Ser Leu Glu Leu Ser
                325                 330                 335

Pro Met Pro Pro Glu Phe Trp Glu Gly Ser Met Leu Glu Lys Pro Ala
            340                 345                 350

Asp Gly Arg Glu Val Val Cys His Ala Ser Ala Trp Asp Phe Tyr Asn
            355                 360                 365

Arg Lys Asp Phe Arg Ile Lys Gln Cys Thr Arg Val Thr Met Asp Gln
            370                 375                 380

Leu Ser Thr Val His His Glu Met Gly His Ile Gln Tyr Tyr Leu Gln
385                 390                 395                 400

Tyr Lys Asp Leu Pro Val Ser Leu Arg Arg Gly Ala Asn Pro Gly Phe
                405                 410                 415

His Glu Ala Ile Gly Asp Val Leu Ala Leu Ser Val Ser Thr Pro Glu
            420                 425                 430

His Leu His Lys Ile Gly Leu Leu Asp Arg Val Thr Asn Asp Thr Glu
            435                 440                 445

Ser Asp Ile Asn Tyr Leu Leu Lys Met Ala Leu Glu Lys Ile Ala Phe
450                 455                 460
```

-continued

```
Leu Pro Phe Gly Tyr Leu Val Asp Gln Trp Arg Trp Gly Val Phe Ser
465                 470                 475                 480

Gly Arg Thr Pro Pro Ser Arg Tyr Asn Phe Asp Trp Trp Tyr Leu Arg
                485                 490                 495

Thr Lys Tyr Gln Gly Ile Cys Pro Pro Val Thr Arg Asn Glu Thr His
            500                 505                 510

Phe Asp Ala Gly Ala Lys Phe His Val Pro Asn Val Thr Pro Tyr Ile
        515                 520                 525

Arg Tyr Phe Val Ser Phe Val Leu Gln Phe Gln Phe His Glu Ala Leu
    530                 535                 540

Cys Lys Glu Ala Gly Tyr Glu Gly Pro Leu His Gln Cys Asp Ile Tyr
545                 550                 555                 560

Arg Ser Thr Lys Ala Gly Ala Lys Leu Arg Lys Val Leu Gln Ala Gly
                565                 570                 575

Ser Ser Arg Pro Trp Gln Glu Val Leu Lys Asp Met Val Gly Leu Asp
            580                 585                 590

Ala Leu Asp Ala Gln Pro Leu Leu Lys Tyr Phe Gln Pro Val Thr Gln
        595                 600                 605

Trp Leu Gln Glu Gln Asn Gln Gln Asn Gly Glu Val Leu Gly Trp Pro
    610                 615                 620

Glu Tyr Gln Trp His Pro Pro Leu Pro Asp Asn Tyr Pro Glu Gly Ile
625                 630                 635                 640

Asp Leu Val Thr Asp Glu Ala Glu Ala Ser Lys Phe Val Glu Glu Tyr
                645                 650                 655

Asp Arg Thr Ser Gln Val Val Trp Asn Glu Tyr Ala Glu Ala Asn Trp
            660                 665                 670

Asn Tyr Asn Thr Asn Ile Thr Thr Glu Thr Ser Lys Ile Leu Leu Gln
        675                 680                 685

Lys Asn Met Gln Ile Ala Asn His Thr Leu Lys Tyr Gly Thr Gln Ala
    690                 695                 700

Arg Lys Phe Asp Val Asn Gln Leu Gln Asn Thr Thr Ile Lys Arg Ile
705                 710                 715                 720

Ile Lys Lys Val Gln Asp Leu Glu Arg Ala Ala Leu Pro Ala Gln Glu
                725                 730                 735

Leu Glu Glu Tyr Asn Lys Ile Leu Leu Asp Met Glu Thr Thr Tyr Ser
            740                 745                 750

Val Ala Thr Val Cys His Pro Asn Gly Ser Cys Leu Gln Leu Glu Pro
        755                 760                 765

Asp Leu Thr Asn Val Met Ala Thr Ser Arg Lys Tyr Glu Asp Leu Leu
    770                 775                 780

Trp Ala Trp Glu Gly Trp Arg Asp Lys Ala Gly Arg Ala Ile Leu Gln
785                 790                 795                 800

Phe Tyr Pro Lys Tyr Val Glu Leu Ile Asn Gln Ala Ala Arg Leu Asn
                805                 810                 815

Gly Tyr Val Asp Ala Gly Asp Ser Trp Arg Ser Met Tyr Glu Thr Pro
            820                 825                 830

Ser Leu Glu Gln Asp Leu Glu Arg Leu Phe Gln Glu Leu Gln Pro Leu
        835                 840                 845

Tyr Leu Asn Leu His Ala Tyr Val Arg Arg Ala Leu His Arg His Tyr
    850                 855                 860

Gly Ala Gln His Ile Asn Leu Glu Gly Pro Ile Pro Ala His Leu Leu
865                 870                 875                 880

Gly Asn Met Trp Ala Gln Thr Trp Ser Asn Ile Tyr Asp Leu Val Val
```

```
                    885                 890                 895
Pro Phe Pro Ser Ala Pro Ser Met Asp Thr Thr Glu Ala Met Leu Lys
                900                 905                 910

Gln Gly Trp Thr Pro Arg Arg Met Phe Lys Glu Ala Asp Asp Phe Phe
                915                 920                 925

Thr Ser Leu Gly Leu Leu Pro Val Pro Pro Glu Phe Trp Asn Lys Ser
                930                 935                 940

Met Leu Glu Lys Pro Thr Asp Gly Arg Glu Val Val Cys His Ala Ser
945                 950                 955                 960

Ala Trp Asp Phe Tyr Asn Gly Lys Asp Phe Arg Ile Lys Gln Cys Thr
                965                 970                 975

Thr Val Asn Leu Glu Asp Leu Val Val Ala His His Glu Met Gly His
                980                 985                 990

Ile Gln Tyr Phe Met Gln Tyr Lys Asp Leu Pro Val Ala Leu Arg Glu
                995                1000                1005

Gly Ala Asn Pro Gly Phe His Glu Ala Ile Gly Asp Val Leu Ala
            1010                1015                1020

Leu Ser Val Ser Thr Pro Lys His Leu His Ser Leu Asn Leu Leu
            1025                1030                1035

Ser Ser Glu Gly Gly Ser Asp Glu His Asp Ile Asn Phe Leu Met
            1040                1045                1050

Lys Met Ala Leu Asp Lys Ile Ala Phe Ile Pro Phe Ser Tyr Leu
            1055                1060                1065

Val Asp Gln Trp Arg Trp Arg Val Phe Asp Gly Ser Ile Thr Lys
            1070                1075                1080

Glu Asn Tyr Asn Gln Glu Trp Trp Ser Leu Arg Leu Lys Tyr Gln
            1085                1090                1095

Gly Leu Cys Pro Pro Val Pro Arg Thr Gln Gly Asp Phe Asp Pro
            1100                1105                1110

Gly Ala Lys Phe His Ile Pro Ser Ser Val Pro Tyr Ile Arg Tyr
            1115                1120                1125

Phe Val Ser Phe Ile Ile Gln Phe Gln Phe His Glu Ala Leu Cys
            1130                1135                1140

Gln Ala Ala Gly His Thr Gly Pro Leu His Lys Cys Asp Ile Tyr
            1145                1150                1155

Gln Ser Lys Glu Ala Gly Gln Arg Leu Ala Thr Ala Met Lys Leu
            1160                1165                1170

Gly Phe Ser Arg Pro Trp Pro Glu Ala Met Gln Leu Ile Thr Gly
            1175                1180                1185

Gln Pro Asn Met Ser Ala Ser Ala Met Leu Ser Tyr Phe Lys Pro
            1190                1195                1200

Leu Leu Asp Trp Leu Arg Thr Glu Asn Glu Leu His Gly Glu Lys
            1205                1210                1215

Leu Gly Trp Pro Gln Tyr Asn Trp Thr Pro Asn Ser Ala Arg Ser
            1220                1225                1230

Glu Gly Pro Leu Pro Asp Ser Gly Arg Val Ser Phe Leu Gly Leu
            1235                1240                1245

Asp Leu Asp Ala Gln Gln Ala Arg Val Gly Gln Trp Leu Leu Leu
            1250                1255                1260

Phe Leu Gly Ile Ala Leu Leu Val Ala Thr Leu Gly Leu Ser Gln
            1265                1270                1275

Arg Leu Phe Ser Ile Arg His Arg Ser Leu His Arg His Ser His
            1280                1285                1290
```

Gly Pro Gln Phe Gly Ser Glu Val Glu Leu Arg His Ser
          1295                1300              1305

<210> SEQ ID NO 288
<211> LENGTH: 222
<212> TYPE: PRT
<213> ORGANISM: Homo sapiens

<400> SEQUENCE: 288

Met Leu Ser Arg Ala Val Cys Gly Thr Ser Arg Gln Leu Ala Pro Val
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220

<210> SEQ ID NO 289
<211> LENGTH: 620
<212> TYPE: PRT
<213> ORGANISM: Homo sapiens

<400> SEQUENCE: 289

Met Ser Lys Ser Lys Cys Ser Val Gly Leu Met Ser Ser Val Val Ala
1               5                   10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
        35                  40                  45

Asn Pro Arg Gln Ser Pro Val Gly Ala Gln Asp Arg Glu Thr Trp Gly
    50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

```
Ala Phe Leu Val Pro Tyr Leu Leu Phe Met Val Ile Ala Gly Met Pro
            100                 105                 110

Leu Phe Tyr Met Glu Leu Ala Leu Gly Gln Phe Asn Arg Glu Gly Ala
            115                 120                 125

Ala Gly Val Trp Lys Ile Cys Pro Ile Leu Lys Gly Val Gly Phe Thr
            130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
                180                 185                 190

His Pro Gly Asp Ser Ser Gly Asp Ser Ser Gly Leu Asn Asp Thr Phe
                195                 200                 205

Gly Thr Thr Pro Ala Ala Glu Tyr Phe Glu Arg Gly Val Leu His Leu
                210                 215                 220

His Gln Ser His Gly Ile Asp Asp Leu Gly Pro Pro Arg Trp Gln Leu
225                 230                 235                 240

Thr Ala Cys Leu Val Leu Val Ile Val Leu Leu Tyr Phe Ser Leu Trp
                245                 250                 255

Lys Gly Val Lys Thr Ser Gly Lys Val Val Trp Ile Thr Ala Thr Met
                260                 265                 270

Pro Tyr Val Val Leu Thr Ala Leu Leu Leu Arg Gly Val Thr Leu Pro
                275                 280                 285

Gly Ala Ile Asp Gly Ile Arg Ala Tyr Leu Ser Val Asp Phe Tyr Arg
                290                 295                 300

Leu Cys Glu Ala Ser Val Trp Ile Asp Ala Ala Thr Gln Val Cys Phe
305                 310                 315                 320

Ser Leu Gly Val Gly Phe Gly Val Leu Ile Ala Phe Ser Ser Tyr Asn
                325                 330                 335

Lys Phe Thr Asn Asn Cys Tyr Arg Asp Ala Ile Val Thr Thr Ser Ile
                340                 345                 350

Asn Ser Leu Thr Ser Phe Ser Ser Gly Phe Val Val Phe Ser Phe Leu
                355                 360                 365

Gly Tyr Met Ala Gln Lys His Ser Val Pro Ile Gly Asp Val Ala Lys
                370                 375                 380

Asp Gly Pro Gly Leu Ile Phe Ile Ile Tyr Pro Glu Ala Ile Ala Thr
385                 390                 395                 400

Leu Pro Leu Ser Ser Ala Trp Ala Val Val Phe Phe Ile Met Leu Leu
                405                 410                 415

Thr Leu Gly Ile Asp Ser Ala Met Gly Gly Met Glu Ser Val Ile Thr
                420                 425                 430

Gly Leu Ile Asp Glu Phe Gln Leu Leu His Arg His Arg Glu Leu Phe
                435                 440                 445

Thr Leu Phe Ile Val Leu Ala Thr Phe Leu Leu Ser Leu Phe Cys Val
                450                 455                 460

Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
                485                 490                 495

Trp Phe Tyr Gly Val Gly Gln Phe Ser Asp Asp Ile Gln Gln Met Thr
                500                 505                 510
```

```
Gly Gln Arg Pro Ser Leu Tyr Trp Arg Leu Cys Trp Lys Leu Val Ser
            515                 520                 525

Pro Cys Phe Leu Leu Phe Val Val Val Ser Ile Val Thr Phe Arg
    530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
        595                 600                 605

Val Arg Gln Phe Thr Leu Arg His Trp Leu Lys Val
    610                 615                 620

<210> SEQ ID NO 290
<211> LENGTH: 490
<212> TYPE: PRT
<213> ORGANISM: Homo sapiens

<400> SEQUENCE: 290

Met Asp Ser Leu Val Leu Val Leu Cys Leu Ser Cys Leu Leu Leu
1               5                   10                  15

Leu Ser Leu Trp Arg Gln Ser Ser Gly Arg Gly Lys Leu Pro Pro Gly
            20                  25                  30

Pro Thr Pro Leu Pro Val Ile Gly Asn Ile Leu Gln Ile Gly Ile Lys
        35                  40                  45

Asp Ile Ser Lys Ser Leu Thr Asn Leu Ser Lys Val Tyr Gly Pro Val
    50                  55                  60

Phe Thr Leu Tyr Phe Gly Leu Lys Pro Ile Val Val Leu His Gly Tyr
65                  70                  75                  80

Glu Ala Val Lys Glu Ala Leu Ile Asp Leu Gly Glu Glu Phe Ser Gly
                85                  90                  95

Arg Gly Ile Phe Pro Leu Ala Glu Arg Ala Asn Arg Gly Phe Gly Ile
            100                 105                 110

Val Phe Ser Asn Gly Lys Lys Trp Lys Glu Ile Arg Arg Phe Ser Leu
        115                 120                 125

Met Thr Leu Arg Asn Phe Gly Met Gly Lys Arg Ser Ile Glu Asp Arg
    130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe His Lys Arg Phe Asp Tyr Lys Asp Gln
            180                 185                 190

Gln Phe Leu Asn Leu Met Glu Lys Leu Asn Glu Asn Ile Lys Ile Leu
        195                 200                 205

Ser Ser Pro Trp Ile Gln Ile Cys Asn Asn Phe Ser Pro Ile Ile Asp
    210                 215                 220

Tyr Phe Pro Gly Thr His Asn Lys Leu Leu Lys Asn Val Ala Phe Met
225                 230                 235                 240

Lys Ser Tyr Ile Leu Glu Lys Val Lys Glu His Gln Glu Ser Met Asp
                245                 250                 255

Met Asn Asn Pro Gln Asp Phe Ile Asp Cys Phe Leu Met Lys Met Glu
            260                 265                 270
```

-continued

```
Lys Glu Lys His Asn Gln Pro Ser Glu Phe Thr Ile Glu Ser Leu Glu
        275                 280                 285

Asn Thr Ala Val Asp Leu Phe Gly Ala Gly Thr Glu Thr Thr Ser Thr
    290                 295                 300

Thr Leu Arg Tyr Ala Leu Leu Leu Leu Leu Lys His Pro Glu Val Thr
305                 310                 315                 320

Ala Lys Val Gln Glu Glu Ile Glu Arg Val Ile Gly Arg Asn Arg Ser
                325                 330                 335

Pro Cys Met Gln Asp Arg Ser His Met Pro Tyr Thr Asp Ala Val Val
            340                 345                 350

His Glu Val Gln Arg Tyr Ile Asp Leu Leu Pro Thr Ser Leu Pro His
        355                 360                 365

Ala Val Thr Cys Asp Ile Lys Phe Arg Asn Tyr Leu Ile Pro Lys Gly
    370                 375                 380

Thr Thr Ile Leu Ile Ser Leu Thr Ser Val Leu His Asp Asn Lys Glu
385                 390                 395                 400

Phe Pro Asn Pro Glu Met Phe Asp Pro His His Phe Leu Asp Glu Gly
                405                 410                 415

Gly Asn Phe Lys Lys Ser Lys Tyr Phe Met Pro Phe Ser Ala Gly Lys
            420                 425                 430

Arg Ile Cys Val Gly Glu Ala Leu Ala Gly Met Glu Leu Phe Leu Phe
        435                 440                 445

Leu Thr Ser Ile Leu Gln Asn Phe Asn Leu Lys Ser Leu Val Asp Pro
    450                 455                 460

Lys Asn Leu Asp Thr Thr Pro Val Val Asn Gly Phe Ala Ser Val Pro
465                 470                 475                 480

Pro Phe Tyr Gln Leu Cys Phe Ile Pro Val
                485                 490
```